United States Patent
Ono et al.

(10) Patent No.: US 9,550,835 B2
(45) Date of Patent: Jan. 24, 2017

(54) ANTI-DDR1 ANTIBODY HAVING ANTI-TUMOR ACTIVITY

(75) Inventors: Mei Ono, Kanagawa (JP); Yuji Sano, Kanagawa (JP); Tsukasa Suzuki, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 340 days.

(21) Appl. No.: 14/240,057

(22) PCT Filed: Aug. 23, 2012

(86) PCT No.: PCT/JP2012/071332
§ 371 (c)(1),
(2), (4) Date: May 19, 2014

(87) PCT Pub. No.: WO2013/027802
PCT Pub. Date: Feb. 28, 2013

(65) Prior Publication Data
US 2014/0248282 A1 Sep. 4, 2014

(30) Foreign Application Priority Data
Aug. 23, 2011 (JP) ................................ 2011-181683

(51) Int. Cl.
| | | |
|---|---|---|
| C07K 16/40 | (2006.01) | |
| C07K 16/28 | (2006.01) | |
| C07K 16/30 | (2006.01) | |
| A61K 39/395 | (2006.01) | |
| A61K 47/48 | (2006.01) | |
| A61K 39/00 | (2006.01) | |

(52) U.S. Cl.
CPC .......... C07K 16/40 (2013.01); A61K 39/3955 (2013.01); A61K 47/48646 (2013.01); C07K 16/2851 (2013.01); C07K 16/3023 (2013.01); A61K 2039/505 (2013.01); C07K 2317/34 (2013.01); C07K 2317/76 (2013.01); C07K 2317/77 (2013.01)

(58) Field of Classification Search
None
See application file for complete search history.

(56) References Cited

FOREIGN PATENT DOCUMENTS

| EP | 1 876 186 | 1/2008 |
| JP | 2005-521420 | 7/2005 |
| WO | WO 95/02187 | 1/1995 |
| WO | WO 03/085125 | 10/2003 |
| WO | WO 2006/098465 | 9/2006 |
| WO | WO 2010/019702 | 2/2010 |

OTHER PUBLICATIONS

International Preliminary Report on Patentability App. Ser. No. PCT/JP2012/071332, dated Feb. 25, 2014, 9 pages.

Abdulhussein et al., "Identification of disulfide-linked dimers of the receptor tyrosine kinase DDR1," *J Biol Chem.*, 283(18):12026-12033 (2008).

Carafoli et al., "Structure of the discoidin domain receptor 1 extracellular region bound to an inhibitory Fab fragment reveals features important for signaling," *Structure*, 20(4):688-697 (2012).

Colas et al., "Molecular markers of endometrial carcinoma detected in uterine aspirates," *Int J Cancer*, 129(10):2435-2444 (2011).

Curat et al., "Mapping of epitopes in discoidin domain receptor 1 critical for collagen binding," *J Biol Chem.*, 276(49):45952-45958 (2001).

Franco et al., "Discoidin domain receptor 1 on bone marrow-derived cells promotes macrophage accumulation during atherogenesis," *Circ Res.*, 105(11):1141-1148 (2009).

Gu et al., "Survey of tyrosine kinase signaling reveals ROS kinase fusions in human cholangiocarcinoma," *PLoS One*, 6(1):e15640 (2011).

Guerrot et al., "Discoidin domain receptor 1 is a major mediator of inflammation and fibrosis in obstructive nephropathy," *Am J Pathol.*, 179(1):83-91 (2011).

Heinzelmann-Schwarz et al., "Overexpression of the cell adhesion molecules DDR1, Claudin 3, and Ep-CAM in metaplastic ovarian epithelium and ovarian cancer," *Clin Cancer Res.*, 10(13):4427-4436 (2004).

Hidalgo-Carcedo et al., "Collective cell migration requires suppression of actomyosin at cell-cell contacts mediated by DDR1 and the cell polarity regulators Par3 and Par6," *Nat Cell Biol.*, 13(1):49-58 (2011).

Johnson et al., "A receptor tyrosine kinase found in breast carcinoma cells has an extracellular discoidin I-like domain," *Proc Natl Acad Sci USA.*, 90(12):5677-81 (1993).

Kim et al., "DDR1 receptor tyrosine kinase promotes prosurvival pathway through Notch1 activation," *J Biol Chem.*, 286(20):17672-17681 (2011).

Kimman et al., "Improving the quality and efficiency of follow-up after curative treatment for breast cancer—rationale and study design of the MaCare trial," *BMC Cancer*, 7:1 (2007).

Ram et al., "Discoidin domain receptor-1a (DDR1a) promotes glioma cell invasion and adhesion in association with matrix metalloproteinase-2," *J Neurooncol.*, 76(3):239-248 (2006).

Rikova et al., "Global survey of phosphotyrosine signaling identifies oncogenic kinases in lung cancer," *Cell.*, 131(6):1190-1203 (2007).

(Continued)

*Primary Examiner* — Ruixiang Li
(74) *Attorney, Agent, or Firm* — Fish & Richardson P.C.

(57) ABSTRACT

As a result of producing anti-DDR1 antibodies and conducting extensive studies on the antitumor activity thereof, antibodies that bind to the stalk domain in the amino acid sequence of human DDR1 were found to have a potent activity even when used alone compared to antibodies that bind to other domains. It was also found that the antibodies have one or more activities selected from the group consisting of: (i) an activity to suppress cell proliferation, (ii) an activity to inhibit cell migration, (iii) an activity to inhibit phosphorylation of DDR1 in cells, (iv) an activity to be taken up into cells, (v) an activity to decrease the expression level of DDR1 in cells, and (vi) an activity to decrease the expression level of TGF-β in cells.

11 Claims, 8 Drawing Sheets

(56) References Cited

OTHER PUBLICATIONS

Shimada et al., "Prostate cancer antigen-1 contributes to cell survival and invasion though discoidin receptor 1 in human prostate cancer," *Cancer Sci.*, 99(1):39-45 (2008).

Shintani et al., "Collagen I-mediated up-regulation of N-cadherin requires cooperative signals from integrins and discoidin domain receptor 1," *J Cell Biol.*, 180(6):1277-1289 (2008).

Yamanaka et al., "Identification of expressed genes characterizing long-term survival in malignant glioma patients," *Oncogene.*, 25(44):5994-6002 (2006).

Yang et al., "Discoidin domain receptor 1 is associated with poor prognosis of non-small cell lung carcinomas," *Oncol Rep.*, 24(2):311-319 (2010).

International Search Report for App. Ser. No. PCT/JP2012/071332, mailed Oct. 2, 2012, 3 pages.

| Clone No. | Subclass | human-DDR1-ECD-Fc | | human-DDR2-ECD-His | |
|---|---|---|---|---|---|
| | | OD450 | Δab OD450 | OD450 | Δab OD450 |
| #115 | IgG1 | 1.531 | 1.455 | 0.064 | 0.006 |
| #27 | IgG2a | 1.528 | 1.452 | 0.064 | 0.006 |
| #24 | IgG1 | 0.793 | 0.717 | 0.073 | 0.015 |
| Control IgG | IgG2a | 0.078 | 0.002 | 0.066 | 0.008 |
| IgG(-) | - | 0.076 | 0.000 | 0.058 | 0.000 |

SEQUENCE LISTING

<160> NUMBER OF SEQ ID NOS: 15

<210> SEQ ID NO 1
<211> LENGTH: 2742
<212> TYPE: DNA
<213> ORGANISM: Homo sapiens

<400> SEQUENCE: 1

| | | | | | | |
|---|---|---|---|---|---|---|
| atgggaccag | aggccctgtc | atctttactg | ctgctgctct | tggtggcaag | tggagatgct | 60 |
| gacatgaagg | acatttttga | tcctgccaag | tgccgctatg | ccctgggcat | gcaggaccgg | 120 |
| accatcccag | acagtgacat | ctctgcttcc | agctcctggt | cagattccac | tgccgcccgc | 180 |
| cacagcaggt | tggagagcag | tgacggggat | ggggcctggt | gccccgcagg | gtcggtgttt | 240 |
| cccaaggagg | aggagtactt | gcaggtggat | ctacaacgac | tgcacctggt | ggctctggtg | 300 |
| ggcacccagg | gacggcatgc | cgggggcctg | gcaaggagt | tctcccggag | ctaccggctg | 360 |
| cgttactccc | gggatggtcg | ccgctggatg | ggctggaagg | accgctgggg | tcaggaggtg | 420 |
| atctcaggca | atgaggaccc | tgagggagtg | gtgctgaagg | accttgggcc | ccccatggtt | 480 |
| gcccgactgg | ttcgcttcta | cccccgggct | gaccgggtca | tgagcgtctg | tctgcgggta | 540 |
| gagctctatg | gctgcctctg | gagggatgga | ctcctgtctt | acaccgcccc | tgtggggcag | 600 |
| acaatgtatt | tatctgaggc | cgtgtacctc | aacgactcca | cctatgacgg | acataccgtg | 660 |
| ggcggactgc | agtatggggg | tctgggccag | ctggcagatg | gtgtggtggg | gctggatgac | 720 |
| tttaggaaga | gtcaggagct | gcgggtctgg | ccaggctatg | actatgtggg | atggagcaac | 780 |
| cacagcttct | ccagtggcta | tgtggagatg | gagtttgagt | ttgaccggct | gagggccttc | 840 |
| caggctatgc | aggtccactg | taacaacatg | cacacgctgg | agcccgtct | gcctggcggg | 900 |
| gtggaatgtc | gcttccggcg | tggccctgcc | atggctggg | aggggagcc | catgcgccac | 960 |
| aacctagggg | gcaacctggg | ggaccccaga | gcccggctg | tctcagtgcc | ccttggcggc | 1020 |
| cgtgtggctc | gctttctgca | gtccgcttc | ctctttgcgg | ggccctggtt | actcttcagc | 1080 |
| gaaatctcct | tcatctctga | tgtggtgaac | aattcctctc | cggcactggg | aggcaccttc | 1140 |
| ccgccagccc | cctggtggcc | gcctggccca | cctcccacca | acttcagcag | cttggagctg | 1200 |
| gagcccagag | ccagcagcc | cgtggccaag | gccgagggga | gcccgaccgc | catcctcatc | 1260 |
| ggctgcctgg | tggccatcat | cctgctcctg | ctgctcatca | ttgccctcat | gctctggcgg | 1320 |
| ctgcactggc | gcaggctcct | cagcaaggct | gaacggaggg | tgttggaaga | ggagctgacg | 1380 |
| gttcacctct | ctgtccctgg | ggacactatc | ctcatcaaca | accgcccagg | tcctagagag | 1440 |
| ccaccccgt | accaggagcc | ccggcctcgt | gggaatccgc | cccactccgc | tccctgtgtc | 1500 |
| cccaatggct | ctgcgttgct | gctctccaat | ccagcctacc | gcctccttct | ggccacttac | 1560 |
| gcccgtcccc | ctcgaggccc | gggccccccc | acacccgcct | gggccaaacc | caccaacacc | 1620 |
| caggcctaca | gtgggactac | atggagcct | gagaagccag | cgccccgct | tctgccccca | 1680 |
| cctcccagca | acagcgtccc | ccattatgcc | gaggctgaca | ttgttaccct | gcagggcgtc | 1740 |
| accgggggca | acacctatgc | tgtgcctgca | ctgcccccag | gggcagtcgg | ggatgggccc | 1800 |
| cccagagtgg | atttccctcg | atctcgactc | cgcttcaagg | agaagcttgg | cgagggccag | 1860 |
| tttgggggag | tgcacctgtg | tgaggtcgac | agccctcaag | atctggttag | tcttgatttc | 1920 |
| ccccttaatg | tgcgtaaggg | acacccttg | ctggtagctg | tcaagatctt | acggccagat | 1980 |
| gccaccaaga | atgccaggaa | tgatttcctg | aaagaggtga | agatcatgtc | gaggctcaag | 2040 |
| gacccaaaca | tcattcggct | gctgggcgtg | tgtgtgcagg | acgacccct | ctgcatgatt | 2100 |

```
actgactaca tggagaacgg cgacctcaac cagttcctca gtgcccacca gctggaggac    2160
aaggcagccg aggggccccc tggggacggg caggctgcgc aggggcccac catcagctac    2220
ccaatgctgc tgcatgtggc agcccagatc gcctccggca tgcgctatct ggccacactc    2280
aactttgtac atcgggacct ggccacgcgg aactgcctag ttggggaaaa tttcaccatc    2340
aaaatcgcag actttggcat gagccggaac ctctatgctg ggactatta ccgtgtgcag    2400 ggccgggcag tgctgcccat ccgctggatg gcctgggagt gcatcctcat ggggaagttc    2460
acgactgcga gtgacgtgtg gcctttggt gtgaccctgt gggaggtgct gatgctctgt    2520
agggcccagc cctttgggca gctcaccgac gagcaggtca tcgagaacgc gggggagttc    2580
ttccgggacc agggccggca ggtgtacctg tcccggccgc ctgcctgccc gcagggccta    2640
tatgagctga tgcttcggtg ctggagccgg gagtctgagc agcgaccacc cttttcccag    2700
ctgcatcggt tcctggcaga ggatgcactc aacacggtgt ga                      2742
```

<210> SEQ ID NO 2
<211> LENGTH: 913
<212> TYPE: PRT
<213> ORGANISM: Homo sapiens

<400> SEQUENCE: 2

```
Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255
```

```
Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
            500                 505                 510

Tyr Arg Leu Leu Leu Ala Thr Tyr Ala Arg Pro Pro Arg Gly Pro Gly
        515                 520                 525

Pro Pro Thr Pro Ala Trp Ala Lys Pro Thr Asn Thr Gln Ala Tyr Ser
    530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575

Leu Gln Gly Val Thr Gly Gly Asn Thr Tyr Ala Val Pro Ala Leu Pro
            580                 585                 590

Pro Gly Ala Val Gly Asp Gly Pro Pro Arg Val Asp Phe Pro Arg Ser
        595                 600                 605

Arg Leu Arg Phe Lys Glu Lys Leu Gly Glu Gly Gln Phe Gly Glu Val
    610                 615                 620

His Leu Cys Glu Val Asp Ser Pro Gln Asp Leu Val Ser Leu Asp Phe
625                 630                 635                 640

Pro Leu Asn Val Arg Lys Gly His Pro Leu Leu Val Ala Val Lys Ile
                645                 650                 655

Leu Arg Pro Asp Ala Thr Lys Asn Ala Arg Asn Asp Phe Leu Lys Glu
            660                 665                 670

Val Lys Ile Met Ser Arg Leu Lys Asp Pro Asn Ile Ile Arg Leu Leu
```

```
              675                 680                 685
Gly Val Cys Val Gln Asp Asp Pro Leu Cys Met Ile Thr Asp Tyr Met
        690                 695                 700

Glu Asn Gly Asp Leu Asn Gln Phe Leu Ser Ala His Gln Leu Glu Asp
705                 710                 715                 720

Lys Ala Ala Glu Gly Ala Pro Gly Asp Gly Gln Ala Ala Gln Gly Pro
                725                 730                 735

Thr Ile Ser Tyr Pro Met Leu Leu His Val Ala Ala Gln Ile Ala Ser
            740                 745                 750

Gly Met Arg Tyr Leu Ala Thr Leu Asn Phe Val His Arg Asp Leu Ala
        755                 760                 765

Thr Arg Asn Cys Leu Val Gly Glu Asn Phe Thr Ile Lys Ile Ala Asp
    770                 775                 780

Phe Gly Met Ser Arg Asn Leu Tyr Ala Gly Asp Tyr Tyr Arg Val Gln
785                 790                 795                 800

Gly Arg Ala Val Leu Pro Ile Arg Trp Met Ala Trp Glu Cys Ile Leu
                805                 810                 815

Met Gly Lys Phe Thr Thr Ala Ser Asp Val Trp Ala Phe Gly Val Thr
            820                 825                 830

Leu Trp Glu Val Leu Met Leu Cys Arg Ala Gln Pro Phe Gly Gln Leu
        835                 840                 845

Thr Asp Glu Gln Val Ile Glu Asn Ala Gly Glu Phe Phe Arg Asp Gln
    850                 855                 860

Gly Arg Gln Val Tyr Leu Ser Arg Pro Pro Ala Cys Pro Gln Gly Leu
865                 870                 875                 880

Tyr Glu Leu Met Leu Arg Cys Trp Ser Arg Glu Ser Glu Gln Arg Pro
                885                 890                 895

Pro Phe Ser Gln Leu His Arg Phe Leu Ala Glu Asp Ala Leu Asn Thr
            900                 905                 910

Val

<210> SEQ ID NO 3
<211> LENGTH: 154
<212> TYPE: PRT
<213> ORGANISM: Homo sapiens

<400> SEQUENCE: 3

Arg Tyr Ala Leu Gly Met Gln Asp Arg Thr Ile Pro Asp Ser Asp Ile
1               5                   10                  15

Ser Ala Ser Ser Ser Trp Ser Asp Ser Thr Ala Ala Arg His Ser Arg
            20                  25                  30

Leu Glu Ser Ser Asp Gly Asp Gly Ala Trp Cys Pro Ala Gly Ser Val
        35                  40                  45

Phe Pro Lys Glu Glu Glu Tyr Leu Gln Val Asp Leu Gln Arg Leu His
50                  55                  60

Leu Val Ala Leu Val Gly Thr Gln Gly Arg His Ala Gly Gly Leu Gly
65                  70                  75                  80

Lys Glu Phe Ser Arg Ser Tyr Arg Leu Arg Tyr Ser Arg Asp Gly Arg
                85                  90                  95

Arg Trp Met Gly Trp Lys Asp Arg Trp Gly Gln Glu Val Ile Ser Gly
            100                 105                 110

Asn Glu Asp Pro Glu Gly Val Val Leu Lys Asp Leu Gly Pro Pro Met
        115                 120                 125

Val Ala Arg Leu Val Arg Phe Tyr Pro Arg Ala Asp Arg Val Met Ser
```

-continued

```
                        130                 135                 140
Val Cys Leu Arg Val Glu Leu Tyr Gly Cys
145                 150

<210> SEQ ID NO 4
<211> LENGTH: 213
<212> TYPE: PRT
<213> ORGANISM: Homo sapiens

<400> SEQUENCE: 4

Gln Thr Met Tyr Leu Ser Glu Ala Val Tyr Leu Asn Asp Ser Thr Tyr
1               5                   10                  15

Asp Gly His Thr Val Gly Gly Leu Gln Tyr Gly Gly Leu Gly Gln Leu
                20                  25                  30

Ala Asp Gly Val Val Gly Leu Asp Asp Phe Arg Lys Ser Gln Glu Leu
            35                  40                  45

Arg Val Trp Pro Gly Tyr Asp Tyr Val Gly Trp Ser Asn His Ser Phe
        50                  55                  60

Ser Ser Gly Tyr Val Glu Met Glu Phe Glu Phe Asp Arg Leu Arg Ala
65                  70                  75                  80

Phe Gln Ala Met Gln Val His Cys Asn Asn Met His Thr Leu Gly Ala
                85                  90                  95

Arg Leu Pro Gly Gly Val Glu Cys Arg Phe Arg Arg Gly Pro Ala Met
                100                 105                 110

Ala Trp Glu Gly Glu Pro Met Arg His Asn Leu Gly Gly Asn Leu Gly
            115                 120                 125

Asp Pro Arg Ala Arg Ala Val Ser Val Pro Leu Gly Arg Gly Val Ala
        130                 135                 140

Arg Phe Leu Gln Cys Arg Phe Leu Phe Ala Gly Pro Trp Leu Leu Phe
145                 150                 155                 160

Ser Glu Ile Ser Phe Ile Ser Asp Val Asn Asn Ser Ser Pro Ala
                165                 170                 175

Leu Gly Gly Thr Phe Pro Pro Ala Pro Trp Trp Pro Gly Pro Pro
            180                 185                 190

Pro Thr Asn Phe Ser Ser Leu Glu Leu Glu Pro Arg Gly Gln Gln Pro
        195                 200                 205

Val Ala Lys Ala Glu
    210

<210> SEQ ID NO 5
<211> LENGTH: 1950
<212> TYPE: DNA
<213> ORGANISM: Artificial Sequence
<220> FEATURE:
<223> OTHER INFORMATION: an artificially synthesized sequence

<400> SEQUENCE: 5
atgggaccag aggccctgtc atctttactg ctgctgctct tggtggcaag tggagatgct        60
gacatgaagg acatttttga tcctgccaag tgccgctatg ccctgggcat gcaggaccgg       120
accatcccag acagtgacat ctctgcttcc agctcctggt cagattccac tgccgcccgc       180
cacagcaggt tggagagcag tgacggggat ggggcctggt gccccgcagg gtcggtgttt       240
cccaaggagg aggagtactt gcaggtggat ctacaacgac tgcacctggt ggctctggtg       300
ggcacccagg acggcatgc cggggggcctg gcaaggagt tctcccggag ctaccggctg       360
cgttactccc gggatggtcg ccgctggatg ggctggaagg accgctgggg tcaggaggtg       420
```

| | |
|---|---|
| atctcaggca atgaggaccc tgagggagtg gtgctgaagg accttgggcc ccccatggtt | 480 |
| gcccgactgg ttcgcttcta ccccccgggct gaccgggtca tgagcgtctg tctgcgggta | 540 |
| gagctctatg gctgcctctg gagggatgga ctcctgtctt acaccgcccc tgtggggcag | 600 |
| acaatgtatt tatctgaggc cgtgtacctc aacgactcca cctatgacgg acataccgtg | 660 |
| ggcggactgc agtatggggg tctgggccag ctggcagatg gtgtggtggg gctggatgac | 720 |
| tttaggaaga gtcaggagct gcgggtctgg ccaggctatg actatgtggg atggagcaac | 780 |
| cacagcttct ccagtggcta tgtggagatg gagtttgagt ttgaccggct gagggccttc | 840 |
| caggctatgc aggtccactg taacaacatg cacacgctgg gagcccgtct gcctggcggg | 900 |
| gtggaatgtc gcttccggcg tggccctgcc atggcctggg aggggagcc catgcgccac | 960 |
| aacctagggg gcaacctggg ggaccccaga gccgggctg tctcagtgcc ccttggcggc | 1020 |
| cgtgtggctc gctttctgca gtgccgcttc ctctttgcgg ggccctggtt actcttcagc | 1080 |
| gaaatctcct tcatctctga tgtggtgaac aattcctctc cggcactggg aggcaccttc | 1140 |
| ccgccagccc cctggtggcc gcctggccca cctcccacca acttcagcag cttggagctg | 1200 |
| gagcccagag ccagcagcc cgtggccaag gccgagggga gcccgaccga acctcgcgga | 1260 |
| ccgacaatca agccctgtcc tccatgcaaa tgcccagcac ctaacctctt gggtggacca | 1320 |
| tccgtcttca tcttccctcc aaagatcaag gatgtactca tgatctccct gagccccata | 1380 |
| gtcacatgtg tggtggtgga tgtgagcgag gatgacccag atgtccagat cagctggttt | 1440 |
| gtgaacaacg tggaagtaca cacagctcag acacaaaccc atagagagga ttacaacagt | 1500 |
| actctccggg tggtcagtgc cctccccatc cagcaccagg actggatgag tggcaaggag | 1560 |
| ttcaaatgca aggtcaacaa caaagacctg ccagcgccca tcgagagaac catctcaaaa | 1620 |
| cccaaagggt cagtaagagc tccacaggta tatgtcttgc ctccaccaga agaagagatg | 1680 |
| actaagaaac aggtcactct gacctgcatg gtcacagact tcatgcctga agacatttac | 1740 |
| gtggagtgga ccaacaacgg gaaaacagag ctaaactaca gaacactga ccagtcctg | 1800 |
| gactctgatg gttcttactt catgtacagc aagctgagag tggaaaagaa gaactgggtg | 1860 |
| gaaagaaata gctactcctg ttcagtggtc cacgagggtc tgcacaatca ccacacgact | 1920 |
| aagagcttct cccggactcc gggtaaatga | 1950 |

<210> SEQ ID NO 6
<211> LENGTH: 649
<212> TYPE: PRT
<213> ORGANISM: Artificial Sequence
<220> FEATURE:
<223> OTHER INFORMATION: an artificially synthesized sequence

<400> SEQUENCE: 6

```
Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95
```

-continued

```
Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
            115                 120                 125

Trp Met Gly Trp Lys Asp Arg Trp Gly Gln Glu Val Ile Ser Gly Asn
            130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
                180                 185                 190

Ser Tyr Thr Ala Pro Val Gly Gln Thr Met Tyr Leu Ser Glu Ala Val
            195                 200                 205

Tyr Leu Asn Asp Ser Thr Tyr Asp Gly His Thr Val Gly Gly Leu Gln
            210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Gly Tyr Val Glu Met Glu Phe
            260                 265                 270

Glu Phe Asp Arg Leu Arg Ala Phe Gln Ala Met Gln Val His Cys Asn
            275                 280                 285

Asn Met His Thr Leu Gly Ala Arg Leu Pro Gly Gly Val Glu Cys Arg
            290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
                340                 345                 350

Ala Gly Pro Trp Leu Leu Phe Ser Glu Ile Ser Phe Ile Ser Asp Val
            355                 360                 365

Val Asn Asn Ser Ser Pro Ala Leu Gly Gly Thr Phe Pro Pro Ala Pro
370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
            405                 410                 415

Glu Pro Arg Gly Pro Thr Ile Lys Pro Cys Pro Pro Cys Lys Cys Pro
            420                 425                 430

Ala Pro Asn Leu Leu Gly Gly Pro Ser Val Phe Ile Phe Pro Pro Lys
            435                 440                 445

Ile Lys Asp Val Leu Met Ile Ser Leu Ser Pro Ile Val Thr Cys Val
            450                 455                 460

Val Val Asp Val Ser Glu Asp Asp Pro Asp Val Gln Ile Ser Trp Phe
465                 470                 475                 480

Val Asn Asn Val Glu Val His Thr Ala Gln Thr Gln Thr His Arg Glu
                485                 490                 495

Asp Tyr Asn Ser Thr Leu Arg Val Val Ser Ala Leu Pro Ile Gln His
            500                 505                 510
```

```
Gln Asp Trp Met Ser Gly Lys Glu Phe Lys Cys Lys Val Asn Asn Lys
        515                 520                 525

Asp Leu Pro Ala Pro Ile Glu Arg Thr Ile Ser Lys Pro Lys Gly Ser
    530                 535                 540

Val Arg Ala Pro Gln Val Tyr Val Leu Pro Pro Glu Glu Glu Met
545                 550                 555                 560

Thr Lys Lys Gln Val Thr Leu Thr Cys Met Val Thr Asp Phe Met Pro
                565                 570                 575

Glu Asp Ile Tyr Val Glu Trp Thr Asn Asn Gly Lys Thr Glu Leu Asn
            580                 585                 590

Tyr Lys Asn Thr Glu Pro Val Leu Asp Ser Asp Gly Ser Tyr Phe Met
        595                 600                 605

Tyr Ser Lys Leu Arg Val Glu Lys Lys Asn Trp Val Glu Arg Asn Ser
    610                 615                 620

Tyr Ser Cys Ser Val Val His Glu Gly Leu His Asn His His Thr Thr
625                 630                 635                 640

Lys Ser Phe Ser Arg Thr Pro Gly Lys
                645
```

<210> SEQ ID NO 7
<211> LENGTH: 2193
<212> TYPE: DNA
<213> ORGANISM: Artificial Sequence
<220> FEATURE:
<223> OTHER INFORMATION: an artificially synthesized sequence

<400> SEQUENCE: 7

```
atgggaccag aggccctgtc atctttactg ctgctgctct tggtggcaag tggagatgct    60
gacatgaagg acatttttga tcctgccaag tgcctctgga gggatggact cctgtcttac   120
accgcccctg tggggcagac aatgtattta tctgaggccg tgtacctcaa cgactccacc   180
tatgacggac ataccgtggg cggactgcag tatgggggtc tgggccagct ggcagatggt   240
gtggtggggc tggatgactt taggaagagt caggagctgc gggtctggcc aggctatgac   300
tatgtgggat ggagcaacca cagcttctcc agtggctatg tggagatgga gtttgagttt   360
gaccggctga gggccttcca ggctatgcag gtccactgta caacatgca cacgctggga   420 gcccgtctgc ctggcggggt ggaatgtcgc ttccggcgtg ccctgccat ggcctgggag   480 ggggagccca tgcgccacaa cctagggggc aacctggggg accccagagc ccgggctgtc   540
tcagtgcccc ttggcggccg tgtggctcgc tttctgcagt gccgcttcct ctttgcgggg   600
ccctggttac tcttcagcga aatctccttc atctctgatg tggtgaacaa ttcctctccg   660
gcactgggag gcaccttccc gccagccccc tggtggccgc ctggcccacc tcccaccaac   720
ttcagcagct ggagctgga gcccagaggc agcagcccg tggccaaggc cgaggggagc   780
ccgaccgcca tcctcatcgg ctgcctggtg ccatcatcc tgctcctgct gctcatcatt   840
gccctcatgc tctggcggct gcactggcgc aggctcctca gcaaggctga acggagggtg   900
ttggaagagg agctgacggt tcacctctct gtccctgggg acactatcct catcaacaac   960
cgcccaggtc ctagagagcc accccgtac caggagcccc ggcctcgtgg aatccgccc   1020 cactccgctc cctgtgtccc caatggctct gcctacagtg ggactatat ggagcctgag   1080 aagccaggcg cccgcttct gccccacct cccagaaca gcgtccccca ttatgccgag   1140
gctgacattg ttaccctgca gggcgtcacc gggggcaaca cctatgctgt gcctgcactg   1200
cccccagggg cagtcgggga tgggcccccc agagtggatt ccctcgatc tcgactccgc   1260
```

```
ttcaaggaga agcttggcga gggccagttt ggggaggtgc acctgtgtga ggtcgacagc    1320
cctcaagatc tggttagtct tgatttcccc cttaatgtgc gtaagggaca ccctttgctg    1380
gtagctgtca agatcttacg gccagatgcc accaagaatg ccaggaatga tttcctgaaa    1440
gaggtgaaga tcatgtcgag gctcaaggac ccaaacatca ttcggctgct gggcgtgtgt    1500
gtgcaggacg accccctctg catgattact gactacatgg agaacggcga cctcaaccag    1560
ttcctcagtg cccaccagct ggaggacaag gcagccgagg gggcccctgg gacgggcag    1620 gctgcgcagg ggcccaccat cagctaccca atgctgctgc atgtggcagc ccagatcgcc    1680
tccggcatgc gctatctggc cacactcaac tttgtacatc gggacctggc cacgcggaac    1740
tgcctagttg gggaaaattt caccatcaaa atcgcagact ttggcatgag ccggaacctc    1800
tatgctgggg actattaccg tgtgcagggc cgggcagtgc tgcccatccg ctggatggcc    1860
tgggagtgca tcctcatggg gaagttcacg actgcgagtg acgtgtgggc ctttggtgtg    1920
accctgtggg aggtgctgat gctctgtagg gcccagcccct ttgggcagct caccgacgag    1980
caggtcatcg agaacgcggg ggagttcttc cggaccagg gccggcaggt gtacctgtcc    2040
cggccgcctg cctgcccgca gggcctatat gagctgatgc ttcggtgctg agccgggag    2100 tctgagcagc gaccacccctt ttcccagctg catcggttcc tggcagagga tgcactcaac    2160
acggtggatt acaaggatga cgacgataag tga    2193
```

<210> SEQ ID NO 8
<211> LENGTH: 730
<212> TYPE: PRT
<213> ORGANISM: Artificial Sequence
<220> FEATURE:
<223> OTHER INFORMATION: an artificially synthesized sequence

<400> SEQUENCE: 8

```
Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Leu
                20                  25                  30

Trp Arg Asp Gly Leu Leu Ser Tyr Thr Ala Pro Val Gly Gln Thr Met
            35                  40                  45

Tyr Leu Ser Glu Ala Val Tyr Leu Asn Asp Ser Thr Tyr Asp Gly His
        50                  55                  60

Thr Val Gly Gly Leu Gln Tyr Gly Gly Leu Gly Gln Leu Ala Asp Gly
65                  70                  75                  80

Val Val Gly Leu Asp Asp Phe Arg Lys Ser Gln Glu Leu Arg Val Trp
                85                  90                  95

Pro Gly Tyr Asp Tyr Val Gly Trp Ser Asn His Ser Phe Ser Ser Gly
            100                 105                 110

Tyr Val Glu Met Glu Phe Glu Phe Asp Arg Leu Arg Ala Phe Gln Ala
        115                 120                 125

Met Gln Val His Cys Asn Asn Met His Thr Leu Gly Ala Arg Leu Pro
    130                 135                 140

Gly Gly Val Glu Cys Arg Phe Arg Arg Gly Pro Ala Met Ala Trp Glu
145                 150                 155                 160

Gly Glu Pro Met Arg His Asn Leu Gly Gly Asn Leu Gly Asp Pro Arg
                165                 170                 175

Ala Arg Ala Val Ser Val Pro Leu Gly Gly Arg Val Ala Arg Phe Leu
            180                 185                 190

Gln Cys Arg Phe Leu Phe Ala Gly Pro Trp Leu Leu Phe Ser Glu Ile
```

```
              195                 200                 205
Ser Phe Ile Ser Asp Val Val Asn Asn Ser Ser Pro Ala Leu Gly Gly
    210                 215                 220

Thr Phe Pro Pro Ala Pro Trp Trp Pro Gly Pro Pro Pro Thr Asn
225                 230                 235                 240

Phe Ser Ser Leu Glu Leu Glu Pro Arg Gly Gln Gln Pro Val Ala Lys
                245                 250                 255

Ala Glu Gly Ser Pro Thr Ala Ile Leu Ile Gly Cys Leu Val Ala Ile
                260                 265                 270

Ile Leu Leu Leu Leu Leu Ile Ile Ala Leu Met Leu Trp Arg Leu His
                275                 280                 285

Trp Arg Arg Leu Leu Ser Lys Ala Glu Arg Arg Val Leu Glu Glu Glu
290                 295                 300

Leu Thr Val His Leu Ser Val Pro Gly Asp Thr Ile Leu Ile Asn Asn
305                 310                 315                 320

Arg Pro Gly Pro Arg Glu Pro Pro Pro Tyr Gln Glu Pro Arg Pro Arg
                325                 330                 335

Gly Asn Pro Pro His Ser Ala Pro Cys Val Pro Asn Gly Ser Ala Tyr
                340                 345                 350

Ser Gly Asp Tyr Met Glu Pro Glu Lys Pro Gly Ala Pro Leu Leu Pro
                355                 360                 365

Pro Pro Pro Gln Asn Ser Val Pro His Tyr Ala Glu Ala Asp Ile Val
370                 375                 380

Thr Leu Gln Gly Val Thr Gly Gly Asn Thr Tyr Ala Val Pro Ala Leu
385                 390                 395                 400

Pro Pro Gly Ala Val Gly Asp Gly Pro Pro Arg Val Asp Phe Pro Arg
                405                 410                 415

Ser Arg Leu Arg Phe Lys Glu Lys Leu Gly Glu Gly Gln Phe Gly Glu
                420                 425                 430

Val His Leu Cys Glu Val Asp Ser Pro Gln Asp Leu Val Ser Leu Asp
                435                 440                 445

Phe Pro Leu Asn Val Arg Lys Gly His Pro Leu Leu Val Ala Val Lys
            450                 455                 460

Ile Leu Arg Pro Asp Ala Thr Lys Asn Ala Arg Asn Asp Phe Leu Lys
465                 470                 475                 480

Glu Val Lys Ile Met Ser Arg Leu Lys Asp Pro Asn Ile Ile Arg Leu
                485                 490                 495

Leu Gly Val Cys Val Gln Asp Asp Pro Leu Cys Met Ile Thr Asp Tyr
                500                 505                 510

Met Glu Asn Gly Asp Leu Asn Gln Phe Leu Ser Ala His Gln Leu Glu
                515                 520                 525

Asp Lys Ala Ala Glu Gly Ala Pro Gly Asp Gly Gln Ala Ala Gln Gly
            530                 535                 540

Pro Thr Ile Ser Tyr Pro Met Leu Leu His Val Ala Ala Gln Ile Ala
545                 550                 555                 560

Ser Gly Met Arg Tyr Leu Ala Thr Leu Asn Phe Val His Arg Asp Leu
                565                 570                 575

Ala Thr Arg Asn Cys Leu Val Gly Glu Asn Phe Thr Ile Lys Ile Ala
                580                 585                 590

Asp Phe Gly Met Ser Arg Asn Leu Tyr Ala Gly Asp Tyr Tyr Arg Val
                595                 600                 605

Gln Gly Arg Ala Val Leu Pro Ile Arg Trp Met Ala Trp Glu Cys Ile
                610                 615                 620
```

Leu Met Gly Lys Phe Thr Thr Ala Ser Asp Val Trp Ala Phe Gly Val
625                 630                 635                 640

Thr Leu Trp Glu Val Leu Met Leu Cys Arg Ala Gln Pro Phe Gly Gln
                645                 650                 655

Leu Thr Asp Glu Gln Val Ile Glu Asn Ala Gly Glu Phe Phe Arg Asp
            660                 665                 670

Gln Gly Arg Gln Val Tyr Leu Ser Arg Pro Pro Ala Cys Pro Gln Gly
        675                 680                 685

Leu Tyr Glu Leu Met Leu Arg Cys Trp Ser Arg Glu Ser Glu Gln Arg
690                 695                 700

Pro Pro Phe Ser Gln Leu His Arg Phe Leu Ala Glu Asp Ala Leu Asn
705                 710                 715                 720

Thr Val Asp Tyr Lys Asp Asp Asp Asp Lys
                725                 730

<210> SEQ ID NO 9
<211> LENGTH: 2016
<212> TYPE: DNA
<213> ORGANISM: Artificial Sequence
<220> FEATURE:
<223> OTHER INFORMATION: an artificially synthesized sequence

<400> SEQUENCE: 9

| | | | | |
|---|---|---|---|---|
| atgggaccag | aggccctgtc | atctttactg | ctgctgctct | tggtggcaag | tggagatgct | 60 |
| gacatgaagg | acatttttga | tcctgccaag | tgccgctatg | ccctgggcat | gcaggaccgg | 120 |
| accatcccag | acagtgacat | ctctgcttcc | agctcctggt | cagattccac | tgccgcccgc | 180 |
| cacagcaggt | tggagagcag | tgacggggat | ggggcctggt | gccccgcagg | gtcggtgttt | 240 |
| cccaaggagg | aggagtactt | gcaggtggat | ctacaacgac | tgcacctggt | ggctctggtg | 300 |
| ggcacccagg | gacggcatgc | cggggggcctg | ggcaaggagt | tctcccggag | ctaccggctg | 360 |
| cgttactccc | gggatggtcg | ccgctggatg | gctggaaagg | accgctgggg | tcaggaggtg | 420 |
| atctcaggca | atgaggaccc | tgagggagtg | gtgctgaagg | accttgggcc | ccccatggtt | 480 |
| gcccgactgg | ttcgcttcta | cccccgggct | gaccgggtca | tgagcgtctg | tctgcgggta | 540 |
| gagctctatg | gctgcctctg | gagggatgga | ctcctgtctt | acaccgcccc | tgtggggggg | 600 |
| agcccgaccg | ccatcctcat | cggctgcctg | gtggccatca | tcctgctcct | gctgctcatc | 660 |
| attgccctca | tgctctggcg | gctgcactgg | cgcaggctcc | tcagcaaggc | tgaacggagg | 720 |
| gtgttggaag | aggagctgac | ggttcacctc | tctgtccctg | ggacactat | cctcatcaac | 780 |
| aaccgcccag | gtcctagaga | gccaccccccg | taccaggagc | ccggcctcg | tgggaatccg | 840 |
| ccccactccg | ctccctgtgt | ccccaatggc | tctgcctaca | gtggggacta | tatggagcct | 900 |
| gagaagccag | gcgccccgct | tctgccccca | cctccccaga | cagcgtccc | ccattatgcc | 960 |
| gaggctgaca | ttgttaccct | gcagggcgtc | accgggggca | acacctatgc | tgtgcctgca | 1020 |
| ctgcccccag | gggcagtcgg | ggatgggccc | cccagagtgg | atttccctcg | atctcgactc | 1080 |
| cgcttcaagg | agaagcttgg | cgagggccag | tttgggagg | tgcacctgtg | tgaggtcgac | 1140 |
| agccctcaag | atctgttag | tcttgatttc | ccccttaatg | tgcgtaaggg | acaccctttg | 1200 |
| ctggtagctg | tcaagatctt | acggccagat | gccaccaaga | atgccaggaa | tgatttcctg | 1260 |
| aaagaggtga | agatcatgtc | gaggctcaag | gacccaaaca | tcattcggct | gctgggcgtg | 1320 |
| tgtgtgcagg | acgaccccct | ctgcatgatt | actgactaca | tggagaacgg | cgacctcaac | 1380 |
| cagttcctca | gtgcccacca | gctggaggac | aaggcagccg | aggggccccc | tggggacggg | 1440 |

```
caggctgcgc aggggcccac catcagctac ccaatgctgc tgcatgtggc agcccagatc   1500
gcctccggca tgcgctatct ggccacactc aactttgtac atcgggacct ggccacgcgg   1560
aactgcctag ttggggaaaa tttcaccatc aaaatcgcag actttggcat gagccggaac   1620
ctctatgctg gggactatta ccgtgtgcag ggccgggcag tgctgcccat ccgctggatg   1680
gcctgggagt gcatcctcat ggggaagttc acgactgcga gtgacgtgtg ggcctttggt   1740
gtgaccctgt gggaggtgct gatgctctgt agggcccagc cctttgggca gctcaccgac   1800
gagcaggtca tcgagaacgc ggggggagttc ttccgggacc agggccggca ggtgtacctg   1860
tcccggccgc ctgcctgccc gcagggccta tatgagctga tgcttcggtg ctggagccgg   1920
gagtctgagc agcgaccacc ctttcccag ctgcatcggt tcctggcaga ggatgcactc   1980
aacacggtgg attacaagga tgacgacgat aagtga                              2016
```

<210> SEQ ID NO 10
<211> LENGTH: 671
<212> TYPE: PRT
<213> ORGANISM: Artificial Sequence
<220> FEATURE:
<223> OTHER INFORMATION: an artificially synthesized sequence

<400> SEQUENCE: 10

```
Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gly Ser Pro Thr Ala Ile Leu Ile Gly
        195                 200                 205

Cys Leu Val Ala Ile Ile Leu Leu Leu Leu Ile Ile Ala Leu Met
    210                 215                 220

Leu Trp Arg Leu His Trp Arg Arg Leu Leu Ser Lys Ala Glu Arg Arg
225                 230                 235                 240

Val Leu Glu Glu Glu Leu Thr Val His Leu Ser Val Pro Gly Asp Thr
                245                 250                 255
```

```
Ile Leu Ile Asn Asn Arg Pro Gly Pro Arg Glu Pro Pro Tyr Gln
            260                 265                 270

Glu Pro Arg Pro Arg Gly Asn Pro Pro His Ser Ala Pro Cys Val Pro
                275                 280                 285

Asn Gly Ser Ala Tyr Ser Gly Asp Tyr Met Glu Pro Glu Lys Pro Gly
            290                 295                 300

Ala Pro Leu Leu Pro Pro Pro Gln Asn Ser Val Pro His Tyr Ala
305                 310                 315                 320

Glu Ala Asp Ile Val Thr Leu Gln Gly Val Thr Gly Gly Asn Thr Tyr
                325                 330                 335

Ala Val Pro Ala Leu Pro Pro Gly Ala Val Gly Asp Gly Pro Pro Arg
            340                 345                 350

Val Asp Phe Pro Arg Ser Arg Leu Arg Phe Lys Glu Lys Leu Gly Glu
            355                 360                 365

Gly Gln Phe Gly Glu Val His Leu Cys Glu Val Asp Ser Pro Gln Asp
        370                 375                 380

Leu Val Ser Leu Asp Phe Pro Leu Asn Val Arg Lys Gly His Pro Leu
385                 390                 395                 400

Leu Val Ala Val Lys Ile Leu Arg Pro Asp Ala Thr Lys Asn Ala Arg
                405                 410                 415

Asn Asp Phe Leu Lys Glu Val Lys Ile Met Ser Arg Leu Lys Asp Pro
            420                 425                 430

Asn Ile Ile Arg Leu Leu Gly Val Cys Val Gln Asp Asp Pro Leu Cys
        435                 440                 445

Met Ile Thr Asp Tyr Met Glu Asn Gly Asp Leu Asn Gln Phe Leu Ser
450                 455                 460

Ala His Gln Leu Glu Asp Lys Ala Ala Glu Gly Ala Pro Gly Asp Gly
465                 470                 475                 480

Gln Ala Ala Gln Gly Pro Thr Ile Ser Tyr Pro Met Leu Leu His Val
                485                 490                 495

Ala Ala Gln Ile Ala Ser Gly Met Arg Tyr Leu Ala Thr Leu Asn Phe
            500                 505                 510

Val His Arg Asp Leu Ala Thr Arg Asn Cys Leu Val Gly Glu Asn Phe
        515                 520                 525

Thr Ile Lys Ile Ala Asp Phe Gly Met Ser Arg Asn Leu Tyr Ala Gly
530                 535                 540

Asp Tyr Tyr Arg Val Gln Gly Arg Ala Val Leu Pro Ile Arg Trp Met
545                 550                 555                 560

Ala Trp Glu Cys Ile Leu Met Gly Lys Phe Thr Thr Ala Ser Asp Val
                565                 570                 575

Trp Ala Phe Gly Val Thr Leu Trp Glu Val Leu Met Leu Cys Arg Ala
            580                 585                 590

Gln Pro Phe Gly Gln Leu Thr Asp Glu Gln Val Ile Glu Asn Ala Gly
        595                 600                 605

Glu Phe Phe Arg Asp Gln Gly Arg Gln Val Tyr Leu Ser Arg Pro Pro
            610                 615                 620

Ala Cys Pro Gln Gly Leu Tyr Glu Leu Met Leu Arg Cys Trp Ser Arg
625                 630                 635                 640

Glu Ser Glu Gln Arg Pro Pro Phe Ser Gln Leu His Arg Phe Leu Ala
                645                 650                 655

Glu Asp Ala Leu Asn Thr Val Asp Tyr Lys Asp Asp Asp Lys
            660                 665                 670
```

<210> SEQ ID NO 11
<211> LENGTH: 2760
<212> TYPE: DNA
<213> ORGANISM: Homo sapiens

<400> SEQUENCE: 11

| | | | | | |
|---|---|---|---|---|---|
| atgggaccag | aggccctgtc | atctttactg | ctgctgctct | tggtggcaag | tggagatgct | 60 |
| gacatgaagg | acatttttga | tcctgccaag | tgccgctatg | ccctgggcat | gcaggaccgg | 120 |
| accatcccag | acagtgacat | ctctgcttcc | agctcctggt | cagattccac | tgccgcccgc | 180 |
| cacagcaggt | tggagagcag | tgacggggat | ggggcctggt | gccccgcagg | gtcggtgttt | 240 |
| cccaaggagg | aggagtactt | gcaggtggat | ctacaacgac | tgcacctggt | ggctctggtg | 300 |
| ggcacccagg | gacggcatgc | cggggggcctg | gcaaggagt | tctcccggag | ctaccggctg | 360 |
| cgttactccc | gggatggtcg | ccgctggatg | ggctggaagg | accgctgggg | tcaggaggtg | 420 |
| atctcaggca | atgaggaccc | tgagggagtg | gtgctgaagg | accttgggcc | ccccatggtt | 480 |
| gcccgactgt | ttcgcttcta | ccccccgggct | gaccgggtca | tgagcgtctg | tctgcgggta | 540 |
| gagctctatg | gctgcctctg | gagggatgga | ctcctgtctt | acaccgcccc | tgtggggcag | 600 |
| acaatgtatt | tatctgaggc | cgtgtacctc | aacgactcca | cctatgacgg | acataccgtg | 660 |
| ggcggactgc | agtatggggg | tctgggccag | ctggcagatg | gtgtggtggg | gctggatgac | 720 |
| tttaggaaga | gtcaggagct | gcgggtctgg | ccaggctatg | actatgtggg | atggagcaac | 780 |
| cacagcttct | ccagtggcta | tgtggagatg | gagtttgagt | ttgaccggct | gagggccttc | 840 |
| caggctatgc | aggtccactg | taacaacatg | cacacgctgg | agcccgtctg | cctggcggg | 900 |
| gtggaatgtc | gcttccggcg | tggccctgcc | atggcctggg | aggggagcc | catgcgccac | 960 |
| aacctagggg | gcaacctggg | ggaccccaga | gcccgggctg | tctcagtgcc | ccttggcggc | 1020 |
| cgtgtggctc | gctttctgca | gtgccgcttc | ctctttgcgg | ggccctggtt | actcttcagc | 1080 |
| gaaatctcct | tcatctctga | tgtggtgaac | aattcctctc | cggcactggg | aggcaccttc | 1140 |
| ccgccagccc | cctggtggcc | gcctggccca | cctcccacca | acttcagcag | cttggagctg | 1200 |
| gagcccagag | gccagcagcc | cgtgccaag | gccgagggga | gcccgaccgc | catcctcatc | 1260 |
| ggctgcctgg | tggccatcat | cctgctcctg | ctgctcatca | ttgccctcat | gctctggcgg | 1320 |
| ctgcactggc | gcaggctcct | cagcaaggct | gaacggaggg | tgttggaaga | ggagctgacg | 1380 |
| gttcacctct | ctgtccctgg | ggacactatc | ctcatcaaca | accgcccagg | tcctagagag | 1440 |
| ccacccccgt | accaggagcc | ccggcctcgt | gggaatccgc | cccactccgc | tccctgtgtc | 1500 |
| cccaatggct | ctgcgttgct | gctctccaat | ccagcctacc | gcctccttct | ggccacttac | 1560 |
| gcccgtcccc | ctcgaggccc | gggccccccc | acacccgcct | gggccaaacc | caccaacacc | 1620 |
| caggcctaca | gtgggactac | tatggagcct | gagaagccag | cgccccgct | tctgcccca | 1680 |
| cctcccagac | acagcgtccc | ccattatgcc | gaggctgaca | ttgttaccct | gcagggcgtc | 1740 |
| accggggggca | acacctatgc | tgtgcctgca | ctgccccag | ggcagtcgg | ggatgggccc | 1800 |
| cccagagtgg | atttccctcg | atctcgactc | cgcttcaagg | agaagcttgg | cgagggccag | 1860 |
| tttggggagg | tgcacctgtg | tgaggtcgac | agccctcaag | atctggttag | tcttgatttc | 1920 |
| cccttaatg | tgcgtaaggg | acacccttg | ctggtagctg | tcaagatctt | acggccagat | 1980 |
| gccaccaaga | atgccagctt | ctccttgttc | tccaggaatg | atttcctgaa | agaggtgaag | 2040 |
| atcatgtcga | ggctcaagga | cccaaacatc | attcggctgc | tgggcgtgtg | tgtgcaggac | 2100 |
| gaccccctct | gcatgattac | tgactacatg | gagaacggcg | acctcaacca | gttcctcagt | 2160 |

-continued

```
gcccaccagc tggaggacaa ggcagccgag ggggcccctg ggacgggca ggctgcgcag    2220 gggcccacca tcagctaccc aatgctgctg catgtggcag cccagatcgc ctccggcatg    2280
cgctatctgg ccacactcaa ctttgtacat cgggacctgg ccacgcggaa ctgcctagtt    2340
ggggaaaatt tcaccatcaa aatcgcagac tttggcatga ccggaacct ctatgctggg    2400 gactattacc gtgtgcaggg ccgggcagtg ctgcccatcc gctggatggc ctgggagtgc    2460
atcctcatgg ggaagttcac gactgcgagt gacgtgtggg cctttggtgt gaccctgtgg    2520
gaggtgctga tgctctgtag ggcccagccc tttgggcagc tcaccgacga gcaggtcatc    2580
gagaacgcgg gggagttctt ccgggaccag ggccggcagg tgtacctgtc ccggccgcct    2640
gcctgcccgc agggcctata tgagctgatg cttcggtgct ggagccggga gtctgagcag    2700
cgaccaccct tttcccagct gcatcggttc ctggcagagg atgcactcaa cacggtgtga    2760
```

<210> SEQ ID NO 12
<211> LENGTH: 884
<212> TYPE: PRT
<213> ORGANISM: Homo sapiens

<400> SEQUENCE: 12

```
Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Gly Tyr Val Glu Met Glu Phe
            260                 265                 270
```

-continued

```
Glu Phe Asp Arg Leu Arg Ala Phe Gln Ala Met Gln Val His Cys Asn
            275                 280                 285
Asn Met His Thr Leu Gly Ala Arg Leu Pro Gly Gly Val Glu Cys Arg
        290                 295                 300
Phe Arg Arg Gly Pro Ala Met Ala Trp Glu Gly Glu Pro Met Arg His
305                 310                 315                 320
Asn Leu Gly Gly Asn Leu Gly Asp Pro Arg Ala Arg Ala Val Ser Val
                325                 330                 335
Pro Leu Gly Gly Arg Val Ala Arg Phe Leu Gln Cys Arg Phe Leu Phe
            340                 345                 350
Ala Gly Pro Trp Leu Leu Phe Ser Glu Ile Ser Phe Ile Ser Asp Val
        355                 360                 365
Val Asn Asn Ser Ser Pro Ala Leu Gly Gly Thr Phe Pro Pro Ala Pro
370                 375                 380
Trp Trp Pro Pro Gly Pro Pro Thr Asn Phe Ser Ser Leu Glu Leu
385                 390                 395                 400
Glu Pro Arg Gly Gln Gln Pro Val Ala Lys Ala Glu Gly Ser Pro Thr
                405                 410                 415
Ala Ile Leu Ile Gly Cys Leu Val Ala Ile Ile Leu Leu Leu Leu
            420                 425                 430
Ile Ile Ala Leu Met Leu Trp Arg Leu His Trp Arg Arg Leu Leu Ser
        435                 440                 445
Lys Ala Glu Arg Arg Val Leu Glu Glu Glu Leu Thr Val His Leu Ser
        450                 455                 460
Val Pro Gly Asp Thr Ile Leu Ile Asn Asn Arg Pro Gly Pro Arg Glu
465                 470                 475                 480
Pro Pro Pro Tyr Gln Glu Pro Arg Pro Arg Gly Asn Pro Pro His Ser
                485                 490                 495
Ala Pro Cys Val Pro Asn Gly Ser Ala Tyr Ser Gly Asp Tyr Met Glu
            500                 505                 510
Pro Glu Lys Pro Gly Ala Pro Leu Leu Pro Pro Pro Gln Asn Ser
        515                 520                 525
Val Pro His Tyr Ala Glu Ala Asp Ile Val Thr Leu Gln Gly Val Thr
530                 535                 540
Gly Gly Asn Thr Tyr Ala Val Pro Ala Leu Pro Pro Gly Ala Val Gly
545                 550                 555                 560
Asp Gly Pro Pro Arg Val Asp Phe Pro Arg Ser Arg Leu Arg Phe Lys
                565                 570                 575
Glu Lys Leu Gly Glu Gly Gln Phe Gly Glu Val His Leu Cys Glu Val
            580                 585                 590
Asp Ser Pro Gln Asp Leu Val Ser Leu Asp Phe Pro Leu Asn Val Arg
        595                 600                 605
Lys Gly His Pro Leu Leu Val Ala Val Lys Ile Leu Arg Pro Asp Ala
        610                 615                 620
Thr Lys Asn Ala Arg Asn Asp Phe Leu Lys Glu Val Lys Ile Met Ser
625                 630                 635                 640
Arg Leu Lys Asp Pro Asn Ile Ile Arg Leu Leu Gly Val Cys Val Gln
                645                 650                 655
Asp Asp Pro Leu Cys Met Ile Thr Asp Tyr Met Glu Asn Gly Asp Leu
            660                 665                 670
Asn Gln Phe Leu Ser Ala His Gln Leu Glu Asp Lys Ala Ala Glu Gly
        675                 680                 685
Ala Pro Gly Asp Gly Gln Ala Ala Gln Gly Pro Thr Ile Ser Tyr Pro
```

| | | 690 | | | 695 | | | 700 | | | | |
|---|---|---|---|---|---|---|---|---|---|---|---|---|

Met Leu Leu His Val Ala Ala Gln Ile Ala Ser Gly Met Arg Tyr Leu
705 710 715 720

Ala Thr Leu Asn Phe Val His Arg Asp Leu Ala Thr Arg Asn Cys Leu
725 730 735

Val Gly Glu Asn Phe Thr Ile Lys Ile Ala Asp Phe Gly Met Ser Arg
740 745 750

Asn Leu Tyr Ala Gly Asp Tyr Tyr Arg Val Gln Gly Arg Ala Val Leu
755 760 765

Pro Ile Arg Trp Met Ala Trp Glu Cys Ile Leu Met Gly Lys Phe Thr
770 775 780

Thr Ala Ser Asp Val Trp Ala Phe Gly Val Thr Leu Trp Glu Val Leu
785 790 795 800

Met Leu Cys Arg Ala Gln Pro Phe Gly Gln Leu Thr Asp Glu Gln Val
805 810 815

Ile Glu Asn Ala Gly Glu Phe Phe Arg Asp Gln Gly Arg Gln Val Tyr
820 825 830

Leu Ser Arg Pro Pro Ala Cys Pro Gln Gly Leu Tyr Glu Leu Met Leu
835 840 845

Arg Cys Trp Ser Arg Glu Ser Glu Gln Arg Pro Pro Phe Ser Gln Leu
850 855 860

His Arg Phe Leu Ala Glu Asp Ala Leu Asn Thr Val Asp Tyr Lys Asp
865 870 875 880

Asp Asp Asp Lys

<210> SEQ ID NO 13
<211> LENGTH: 1269
<212> TYPE: DNA
<213> ORGANISM: Homo sapiens

<400> SEQUENCE: 13

| | | | | | |
|---|---|---|---|---|---|
| atgggaccag aggccctgtc atctttactg ctgctgctct tggtggcaag tggagatgct | | | | | 60 |
| gacatgaagg acatttttga tcctgccaag tgccgctatg ccctgggcat gcaggaccgg | | | | | 120 |
| accatcccag acagtgacat ctctgcttcc agctcctggt cagattccac tgccgcccgc | | | | | 180 |
| cacagcaggt tggagagcag tgacggggat ggggcctggt gccccgcagg gtcggtgttt | | | | | 240 |
| cccaaggagg aggagtactt gcaggtggat ctacaacgac tgcacctggt ggctctggtg | | | | | 300 |
| ggcacccagg acggcatgc cggggcctg gcaaggagt ctcccggag ctaccggctg | | | | | 360 |
| cgttactccc gggatggtcg ccgctggatg ggctggaagg accgctgggg tcaggaggtg | | | | | 420 |
| atctcaggca atgaggaccc tgagggagtg gtgctgaagg accttgggcc ccccatggtt | | | | | 480 |
| gcccgactgg ttcgcttcta cccccgggct gaccgggtca tgagcgtctg tctgcgggta | | | | | 540 |
| gagctctatg gctgcctctg gagggatgga ctcctgtctt acaccgcccc tgtggggcag | | | | | 600 |
| acaatgtatt tatctgaggc cgtgtacctc aacgactcca cctatgacgg acataccgtg | | | | | 660 |
| ggcggactgc agtatggggg tctgggccag ctggcagatg gtgtggtggg gctggatgac | | | | | 720 |
| tttaggaaga gtcaggagct gcgggtctgg ccaggctatg actatgtggg atggagcaac | | | | | 780 |
| cacagcttct ccagtggcta tgtggagatg gagtttgagt tgaccggct gagggccttc | | | | | 840 |
| caggctatgc aggtccactg taacaacatg cacacgctgg agcccgtctt gcctggcggg | | | | | 900 |
| gtggaatgtc gcttccggcg tggccctgcc atggcctggg aggggagcc catgcgccac | | | | | 960 |
| aacctagggg gcaacctggg ggaccccaga gcccgggctg tctcagtgcc ccttggcggc | | | | | 1020 |

```
cgtgtggctc gctttctgca gtgccgcttc ctctttgcgg ggccctggtt actcttcagc    1080
gaaatctcct tcatctctga tgtggtgaac aattcctctc cggcactggg aggcaccttc    1140
ccgccagccc cctggtggcc gcctggccca cctccaccaa acttcagcag cttggagctg    1200
gagcccagag ccagcagcc cgtggccaag gccgagggga gcccgaccca tcatcaccat    1260
caccattga                                                            1269
```

<210> SEQ ID NO 14
<211> LENGTH: 422
<212> TYPE: PRT
<213> ORGANISM: Homo sapiens

<400> SEQUENCE: 14

```
Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
```

-continued

```
                325                 330                 335
Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
            355                 360                 365

Val Asn Asn Ser Ser Pro Ala Leu Gly Gly Thr Phe Pro Pro Ala Pro
        370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

His His His His His His
            420

<210> SEQ ID NO 15
<211> LENGTH: 11
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: phosphotyrosine

<400> SEQUENCE: 15

Leu Tyr Ala Gly Asp Tyr Tyr Arg Val Gln Gly
1               5                   10
```

ANTI-DDR1 ANTIBODY HAVING ANTI-TUMOR ACTIVITY

CROSS-REFERENCE TO RELATED APPLICATIONS

This application is the National Stage of International Application Serial No. PCT/JP2012/071332, filed on Aug. 23, 2012, which claims the benefit of Japanese Patent Application Serial No. 2011-181683, filed on Aug. 23, 2011.

TECHNICAL FIELD

The present invention relates to novel DDR1 antibodies having antitumor activity and to agents for treating cancer comprising the antibodies as an active ingredient.

BACKGROUND ART

Discoidin Domain Receptor 1 (also referred to as DDR1, EDDR1, NEP, NTRK1 or CAK; hereinafter referred to as DDR1) is a receptor tyrosine kinase (RTK) having a molecular weight of 105 kDa that was cloned from human placental tissue as a homologous protein of RTK (Non-Patent Document 1). It is known to induce signal transduction to downstream molecules through its autophosphorylation that occurs as a result of binding with collagen, which is the ligand (Non-Patent Document 2). DDR1 is a single-pass transmembrane receptor, and its extracellular domain is composed of a discoidin (DS) domain and stalk domain from the N-terminal; the former is required for binding to collagen, while the latter is required for dimerization of DDR1, and both have been reported to be required for autophosphorylation of DDR1 by collagen (Non-Patent Documents 3 and 4).

Suggested molecular functions of DDR1 are contribution to cellular morphological changes, adhesion, cell migration, infiltration, proliferation, inhibition of apoptosis, and the like. Experimental findings serving as the basis for these presumed functions are based on phenotype analyses of DDR1-overexpressing strains or DDR1 expression-suppressed strains, and phenomena occurring in cells induced by collagen treatment. Experimental findings including adhesion and increased infiltration in macrophages (Non-Patent Document 5), increased infiltration ability and suppression of apoptosis in human prostate cancer cells (Non-Patent Document 6), suppression of apoptosis and increased proliferation in human colorectal cancer cells (Non-Patent Document 7), and increased cell migration ability and increased infiltration ability in human lung cancer cells (Non-Patent Document 8) have been reported thus far, strongly suggesting involvement of the molecular functions of DDR1 in cancer proliferation and metastasis. In addition, high expression and activity levels of DDR1 in cancer tissue have been reported in multiple types of cancer as indicated in the following cases: glioma (Non-Patent Document 9), breast cancer (Non-Patent Document 10), endometrial cancer (Non-Patent Document 11), ovarian cancer (Non-Patent Document 12), lung cancer (Non-Patent Document 13) and bile duct cancer (Non-Patent Document 14). In addition, the correlation between expression of DDR1 and the prognosis and metastasis of cancer has been reported in glioma (Non-Patent Document 15) and lung cancer (Non-Patent Document 8). On the other hand, the existence of a function of DDR1 that is not mediated by collagen binding activity or kinase activity has also been suggested in recent years (Non-Patent Document 16), thus indicating that there are still aspects of the mechanism of action of DDR1 that remain unknown.

With respect to using DDR1 as a target of cancer therapy, an approach has already been disclosed based on the potential for screening cancer therapeutic agents, by using as indicators, DDR1-mediated phenomena (such as phosphorylation) and measuring whether or not they are inhibited, based on experimental results which indicate that DDR1 is highly expressed in cancer cells of breast cancer or the like (Patent Document 1). In addition, polyclonal antibodies to DDR1 have been prepared, which have been reported to neutralize binding between DDR1 and collagen as well as suppress the cell protective action of collagen in cancer cells (Patent Document 2). Moreover, following preparation of monoclonal antibodies to DDR1, it was reported that these monoclonal antibodies bind to an epitope in the DS domain of DDR1, particularly to an epitope which has a tryptophan residue at position 53 at its center, and inhibit collagen-induced phosphorylation of DDR1. Although a remarkable antitumor activity was not demonstrated when said antibodies were used alone in a colorectal cancer xenograft model, antitumor activity was demonstrated when used together with irinotecan, a chemotherapeutic agent (Patent Document 3). However, an example of an anti-DDR1 antibody capable of demonstrating potent antitumor effects in vivo even when used alone remains to be found.

PRIOR ART DOCUMENTS

Patent Documents

[Patent Document 1] WO1995/002187
[Patent Document 2] WO2006/098465
[Patent Document 3] WO2010/019702

Non-Patent Documents

[Non-patent Document 1] Johnson J. D. et al., Proc. Natl. Acad. Sci. USA 1993; 90:5677-81
[Non-patent Document 2] Shintani Y. et al., J. Cell Biol. 2008; 180:1277-89
[Non-patent Document 3] Curat C. A. et al., J. Biol. Chem. 2001; 276:45952-58
[Non-patent Document 4] Abdulhussein R. et al., J. Biol. Chem. 2008; 283:12026-12033
[Non-patent Document 5] Franco C. et al., Circ. Res. 2009; 105:1141-8
[Non-patent Document 6] Shimada K. et al., Cancer Sci. 2008; 99:39-45
[Non-patent Document 7] Kim H. G. et al., J. Biol. Chem. 2011; 286:17672-81
[Non-patent Document 8] Yang S. H. et al., Oncol. Rep. 2010; 24:311-9
[Non-patent Document 9] Ram R. et al., J. Neurooco 1.2006; 76:239-48
[Non-patent Document 10] Kimman M. L. et al., BMC Cancer 2007; 7:1-20
[Non-patent Document 11] Colas E. et al., Int. J. Cancer 2011; 129:
[Non-patent Document 12] Heinzelmann-Schwarz V. A. et al., Clin. Cancer Res. 2004; 10:4427-36
[Non-patent Document 13] Rikova K. et al., Cell 2007; 131:1190-203
[Non-patent Document 14] Gu T. L. et al., PLoS One 2011; 6:e15640

[Non-patent Document 15] Yamanaka R. et al., Oncogene 2006; 25:5994-6002

[Non-patent Document 16] Hidalgo-Carcedo C. et al., Nat. Cell Biol. 2011; 13:49-58

SUMMARY OF THE INVENTION

Problems to be Solved by the Invention

The present invention was made in view of the above circumstances, and an objective of the present invention is to provide novel anti-DDR1 antibodies having antitumor activity. In addition, an object of the present invention is to provide agents for treating or preventing cancer comprising the antibodies as an active ingredient.

Means for Solving the Problems

As a result of producing anti-DDR1 antibodies and conducting extensive research on their antitumor activity, the present inventors discovered for the first time that antibodies that bind to the stalk domain in the amino acid sequence of human DDR1 have a potent antitumor activity even when used alone, compared to using antibodies that bind to other domains. The present inventors also simultaneously found that these antibodies have one or more of activities selected from the group consisting of:
(i) an activity to suppress cell proliferation,
(ii) an activity to inhibit cell migration,
(iii) an activity to inhibit phosphorylation of DDR1 in cells,
(iv) an activity to be internalized into cells,
(v) an activity to decrease the expression level of DDR1 in cells, and
(vi) an activity to decrease the expression level of TGF-β in cells.

The present invention is based on such findings, and more specifically relates to the inventions indicated below.
[1] An antibody that binds to the stalk domain of DDR1.
[2] The antibody according to [1], which suppresses cell proliferation.
[3] The antibody according to [1] or [2], which inhibits cell migration.
[4] The antibody according to any one of [1] to [3], which inhibits phosphorylation of DDR1 in cells.
[5] The antibody according to any one of [1] to [4], which is taken up into cells.
[6] The antibody according to any one of [1] to [5], which decreases the expression level of DDR1 in cells.
[7] The antibody according to any one of [1] to [6], which decreases the expression level of TGF-β in cells.
[8] The antibody according to any one of [2] to [7], wherein the cells are cancer cells.
[9] The antibody according to [8], wherein the cancer is lung cancer, breast cancer, glioma, ovarian cancer, gastric cancer, pancreatic cancer, esophageal cancer, endometrial cancer or bile duct cancer.
[10] An antibody according to any of the following (a) to (c):
(a) an antibody having an amino acid sequence identical to the antibody produced from a hybridoma deposited under Accession No. FERM BP-11399 (#115),
(b) an antibody having an amino acid sequence identical to the antibody produced from a hybridoma deposited under Accession No. FERM BP-11398 (#27), and
(c) an antibody having an amino acid sequence identical to the antibody produced from a hybridoma deposited under Accession No. FERM BP-11397 (#24).
[11] An antibody having a CDR sequence identical to a CDR sequence possessed by any of the antibodies of (a) to (c) according to [10].
[12] An antibody that competitively binds for DDR1 with the antibody according to any one of [1] to [11].
[13] An antibody that binds to the same epitope as that to which the antibody according to any one of [1] to [11] binds.
[14] An antibody in which one or more amino acids in the antibody according to any one of [1] to [13] have been added, deleted, and/or substituted with other amino acids, and has a binding activity to the stalk domain of DDR1 that is equivalent to that of the antibody prior to the addition, deletion, and/or substitution.
[15] The antibody according to any one of [1] to [14] that is a monoclonal antibody.
[16] The antibody according to any one of [1] to [15] that is a chimeric antibody or humanized antibody.
[17] The antibody according to any one of [1] to [16] that is a minibody.
[18] The antibody according to any one of [1] to [17] that is linked with a cytotoxic agent.
[19] A nucleic acid that encodes the antibody according to any one of [1] to [18].
[20] A vector that comprises the nucleic acid according to [19].
[21] A host cell that retains the vector according to [20].
[22] An antibody collected from a culture supernatant obtained by culturing the cell according to [21].
[23] A hybridoma that produces an antibody that binds to the stalk domain of DDR1.
[24] A hybridoma according to any of the following (a) to (c):
(a) a hybridoma deposited under Accession No. FERM BP-11399 (#115),
(b) a hybridoma deposited under Accession No. FERM BP-11398 (#27), and
(c) a hybridoma deposited under Accession No. FERM BP-11397 (#24).
[25] An agent for treating or preventing cancer, comprising the antibody according to any one of [1] to [18] or [22] as an active ingredient.
[26] The agent for treating or preventing cancer according to [25], wherein the cancer is lung cancer, breast cancer, glioma, ovarian cancer, gastric cancer, pancreatic cancer, esophageal cancer, endometrial cancer, or bile duct cancer.
[27] An agent for suppressing cell growth, comprising the antibody according to any one of [1] to [18] or [22] as an active ingredient.
[28] An agent for inhibiting cell migration, comprising the antibody according to any one of [1] to [18] or [22] as an active ingredient.
[29] An agent for inhibiting phosphorylation of DDR1 in a cell, which comprises the antibody according to any one of [1] to [18] or [22] as an active ingredient.
[30] An agent for suppressing expression level of DDR1 in a cell, which comprises the antibody according to any one of [1] to [18] or [22] as an active ingredient.
[31] An agent for suppressing expression level of TGF-β in a cell, which comprises the antibody according to any one of [1] to [18] or [22] as an active ingredient.
[32] The agent according to any one of [25] to [31], further comprising a cytotoxic agent.
[33] A method for treating or preventing cancer, comprising administration of an effective amount of the antibody according to any one of [1] to [18] or [22] to a mammal.

[34] A method for suppressing cell proliferation, comprising administration of an effective amount of the antibody according to any one of [1] to [18] or [22] to a mammal.
[35] A method for inhibiting cell migration, comprising administration of an effective amount of the antibody according to any one of [1] to [18] or [22] to a mammal.
[36] A method for inhibiting phosphorylation in a cell, comprising administration of an effective amount of the antibody according to any one of [1] to [18] or [22] to a mammal.
[37] A method for suppressing expression of DDR1 in a cell, comprising administration of an effective amount of the antibody according to any one of [1] to [18] or [22] to a mammal.
[38] A method for suppressing expression of TGF-β in a cell, comprising administration of an effective amount of the antibody according to any one of [1] to [18] or [22] to a mammal.
[39] The method according to any one of [33] to [38], further comprising administration of a cytotoxic agent.
[40] A method for producing an antibody, comprising a step of culturing the cell according to [21] and collecting the antibody from the culture supernatant.

In addition, the present invention relates to the inventions indicated below.
[41] A method for treating cancer, comprising administration of an effective dose of the antibody of any one of [1] to [18] or [22] to a subject afflicted with cancer.
[42] A method for treating cancer, comprising administration of an effective dose of the antibody of any one of [1] to [18] or [22] to a subject diagnosed as having cancer.
[43] A method for treating cancer, comprising the step of diagnosing whether a subject has cancer, and the step of administering an effective dose of the antibody of any one of [1] to [18] or [22] to a subject diagnosed as having cancer.
[44] The method of [42] or [43], wherein said diagnosis uses as an indicator the expression level of DDR1 in a biological sample obtained from a subject.
[45] The method of [44], wherein said subject is suggested to have cancer based on a rise in the expression level of DDR1 compared to a normal control level in said diagnosis.
[46] The method of any one of [41] to [45], wherein the cancer is a cancer that expresses DDR1.
[47] The method of any one of [41] to [45], wherein the cancer is a cancer that expresses a higher level of DDR1 than normal.
[48] The method of any one of [41] to [45], wherein the cancer is lung cancer, breast cancer, glioma, ovarian cancer, gastric cancer, pancreatic cancer, esophageal cancer, endometrial cancer or bile duct cancer.

Moreover, the present invention also relates to the inventions indicated below.
[a] Use of an antibody of the present invention in the production of an agent for treating or preventing cancer, an agent for suppressing cell proliferation, an agent for inhibiting cell migration, an agent for inhibiting phosphorylation of DDR1 in cells, an agent for suppressing expression level of DDR1 in cells, or an agent for suppressing expression level of TGF-β in cells.
[b] An antibody of the present invention for use in a method of treating or preventing cancer, a method of suppressing cell proliferation, a method of inhibiting cell migration, a method of inhibiting phosphorylation in cells, a method of suppressing expression of DDR1 in cells, or a method of suppressing expression of TGF-β in cells.
[c] A process for producing an agent for treating or preventing cancer, an agent for suppressing cell proliferation, an agent for inhibiting cell migration, an agent for inhibiting phosphorylation of DDR1 in cells, an agent for suppressing expression level of DDR1 in cells, or an agent for suppressing expression level of TGF-β in cells, comprising the step of using an antibody of the present invention.

BRIEF DESCRIPTION OF THE DRAWINGS

FIG. 1 is a table showing the clone numbers, subclasses, and binding activity to DDR1 and DDR2 of anti-DDR1 antibodies. Values in the table represent absorbance at 450 nm in ELISA (OD450) and differences in absorbance between when the secondary antibody was present and absent (Δab OD450). Each antibody was shown to specifically bind to DDR1.

FIG. 2(a) is a schematic diagram depicting full-length DDR1 (Full Length or FL), DDR1 from which the DS domain had been deleted (ΔDS), and DDR1 from which the stalk domain had been deleted (ΔStalk). FIG. 2(b) shows photographs used to evaluate binding of each antibody to FL-DDR1, ΔDS-DDR1 and ΔStalk-DDR1 by IP-western method. Each anti-DDR1 antibody was used for immunoprecipitation (IP), and anti-FLAG antibody was used for western blotting. Anti-DDR1 antibodies #115, #27 and #24 were all shown to bind to the stalk domain of DDR1. On the other hand, 20M102 was shown to bind to the DS domain of DDR1.

In FIG. 4(a), the ligand-dependent cell migration activity of human lung carcinoma cell line NCI-H1993 was measured using the xCELLigence System™. Collagen type 4 was used for the ligand. The degree of cell migration inhibition (%) of each anti-DDR1 antibody is indicated on the vertical axis, taking as 100 the case when the ligand-induced cell migration is completely inhibited. Negative values for the degree of inhibition indicate that cell migration was increased by addition of antibody compared to ligand alone. Inhibition of ligand-dependent cell migration was observed for antibodies #115 and #24. In FIG. 4(b), ligand-dependent cell migration activity of human lung carcinoma cell line NCI-H1993 was measured using the Cultrex assay kit. Collagen type 4 was used for the ligand. The degree of cell migration inhibition (%) of each anti-DDR1 antibody is indicated on the vertical axis, taking as 100 the case when the ligand-induced cell migration is completely inhibited. Inhibition of ligand-dependent cell migration was observed for antibodies #115, #24 and #27.

MODE FOR CARRYING OUT THE INVENTION

Figure 2:
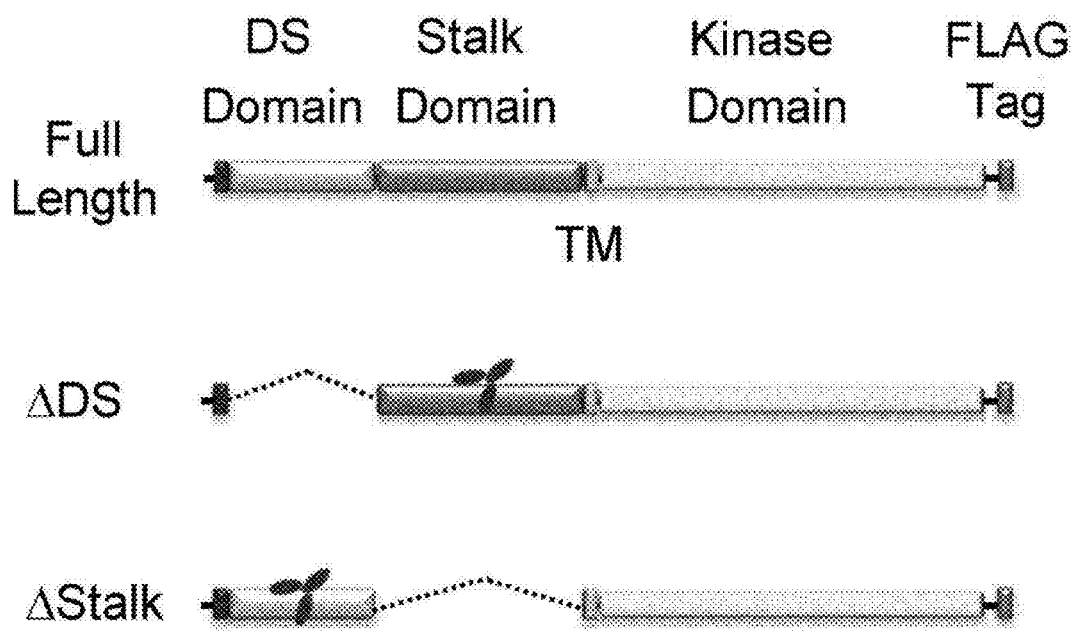
FIG. 2 indicates the domain of DDR1 to which the anti-DDR1 antibody binds.
Figure 2:
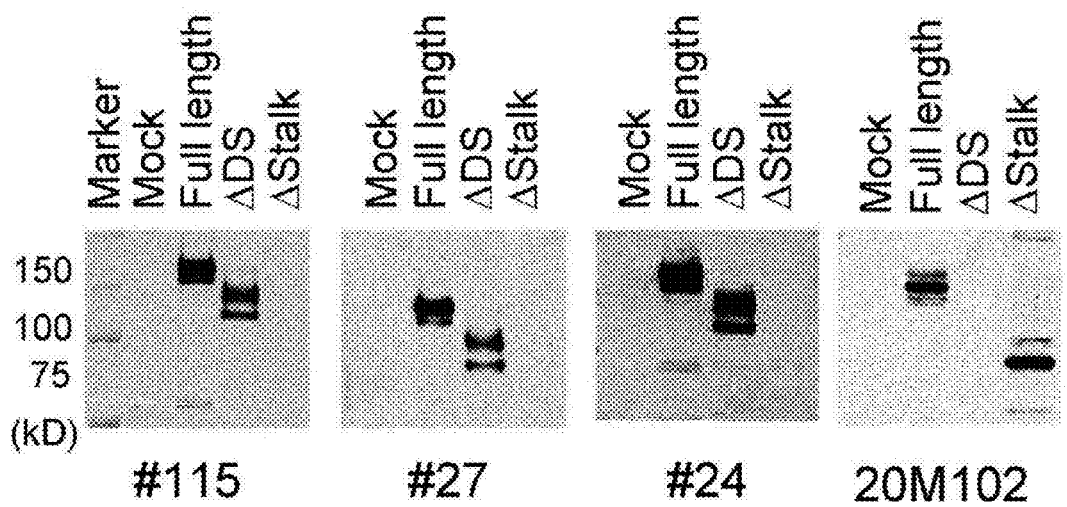

The present invention provides novel anti-DDR1 antibodies that have antitumor activity.

The inventors of the present invention discovered for the first time that antibodies binding to the stalk domain of the extracellular domain of discoidin domain receptor 1 (DDR1) protein have potent antitumor activity even when used alone, compared to antibodies that bind to other discoidin (DS) domains. Namely, the present invention provides antibodies that bind to the stalk domain of DDR1.

The animal species of DDR1 used in the present invention is preferably mammalian and most preferably human. The gene sequence and amino acid sequence of human DDR1 are registered under GenBank Accession No. NM_013993 and NP_054699, respectively. As for species other than humans, the gene sequence and amino acid sequence of mouse DDR1 are registered under GenBank Accession No. NM_007584 and NP_031610, respectively, while the gene sequence and amino acid sequence of rat DDR1 are registered under GenBank Accession No. NM_013137 and NP_037269, respectively. The sequences in other animal species can be determined by those skilled in the art by gene cloning technology and the like using interspecies homology.

DDR1 is a single-pass transmembrane receptor tyrosine kinase (RTK), and is structurally divided into an extracellular domain, transmembrane domain and intracellular domain (kinase domain). The amino acid sequence of human DDR1 is shown in SEQ ID NO: 2 and the nucleotide sequence is shown in SEQ ID NO: 1. Moreover, the extracellular domain contains a discoidin (DS) domain and a stalk domain, and the DS domain is thought to be involved in binding with collagen, which is the ligand. In the present specification, the domain composed of the amino acid sequence from the 32nd amino acid to the 185th amino acid in the amino acid sequence of human DDR1 (SEQ ID NO: 2) is referred to as the DS domain, while the domain composed of the amino acid sequence from the 199th amino acid to the 412th amino acid is referred to as the stalk domain. The amino acid sequence of the DS domain of human DDR1 is shown in SEQ ID NO: 3, while the amino acid sequence of the stalk domain is shown in SEQ ID NO: 4. Domains corresponding to each DDR1 domain in species other than humans can be similarly determined based on sequence homology with human DDR1.

In the present invention, antibody binding activity can be measured using techniques known to those skilled in the art, such as enzyme-linked immunosorbent assay (ELISA), Biacore, western blotting, or FACS. In the present invention, "binding" means that the value of binding activity measured using a method such as one described above is two times or higher than the value of binding activity of a negative control or the background value of the measurement method being used; it is preferably three times or higher, more preferably five times or higher, and most preferably ten times or higher.

An antibody that binds to the stalk domain of DDR1 can be produced by acquiring a plurality of anti-DDR1 antibodies by immunizing an animal such as a mouse with a DDR1 protein, followed by selecting antibodies that bind to the stalk domain by screening as described in Example 1 below. The antibody can also be produced by preliminarily producing a partial protein equivalent to the stalk domain of DDR1 using genetic engineering techniques known to those skilled in the art, and then immunizing an animal such as a mouse with that partial protein.

A preferable embodiment of an anti-DDR1 antibody provided by the present invention is an anti-DDR1 antibody that suppresses cell proliferation.

The cells in the present invention may be primary cultured cells collected from body tissue or a cell line that has been established by immortalizing such cells by some form of method. The cell phenotype is preferably that of cells that highly express DDR1 gene or DDR1 protein compared to ordinary cells. The amount of DDR1 gene expressed in cells can be evaluated using a technique known to those skilled in the art such as RT-PCR or GeneChip analysis using a primer specific to DDR1 gene. The amount of DDR1 protein expressed in cells can be evaluated using a technique known to those skilled in the art such as western blotting or immunohistostaining (IHC) using an antibody specific to DDR1 protein.

In the present invention, "suppression of cell proliferation" refers to a decrease in cell proliferation in cells that have been contacted by anti-DDR1 antibody compared to cells that have not been contacted by the antibody. A decrease in cell proliferation includes a decrease in growth rate while the cells are in a viable state, as well as induction of cell death by apoptosis, necrosis, and the like. Suppression of cell proliferation is preferably induced as a result of anti-DDR1 antibody having bound to DDR1 on the cell surface. Suppression of cell proliferation may be observed in vitro or in vivo. Suppression of cell proliferation in vitro can be measured with an assay system known to those skilled in the art such as [$^3$H]thymidine uptake, MTT, or WST. Suppression of cell proliferation in vivo can be measured with an assay system known to those skilled in the art such as a xenograft model in which human cells are grafted into a mouse.

Proliferation is preferably suppressed by anti-DDR1 antibody by, for example, 30% or more, 40% or more, 50% or more, 60% or more, or 70% or more based on a value of 100% for the case of cell proliferation in the evaluation system being completely suppressed. In contrast to antibody 20M102 disclosed in the prior art (Patent Document 3) that binds to the DS domain of DDR1 suppressing cell proliferation by about 20% in vivo (see FIG. 6 of the aforementioned publication), antibodies #24, #27, and #115 provided by the present invention that bind to the stalk domain of DDR1 were found by the present inventors to suppress cell proliferation in vivo by 48%, 61%, and 71%, respectively (see Example 3 to be subsequently described).

A preferable embodiment of the anti-DDR1 antibody provided by the present invention is anti-DDR1 antibody that inhibits cell migration.

Cell migration is a phenomenon that explains the autonomous movement of cells in the living body and such; antibodies that inhibit cell migration are thought to be useful as having the potential to suppress infiltration and metastasis of cancer cells. In the present invention, "inhibition of cell migration" refers to a decrease in cell migration activity in cells that have been contacted with an anti-DDR1 antibody compared to cells that have not been contacted with the antibody. Inhibition of cell migration can be measured with an assay system that detects migration of cells between chambers as described in, for example, Example 4. Cell migration is known to be stimulated in cells in which DDR1 protein is expressed on the cell surface as a result of a ligand binding to the extracellular domain of DDR1, and is known to be particularly induced as a result of collagen binding to the domain as ligand (Yang, S. H., et al., Oncol. Rep. (2010) 24, 311-319). The collagen is suitably type I collagen or type IV collagen. Inhibition of cell migration is preferably induced as a result of anti-DDR1 antibody having inhibited binding between DDR1 and a ligand.

A preferable embodiment of the anti-DDR1 antibody provided by the present invention is anti-DDR1 antibody that inhibits phosphorylation of DDR1 in cells.

Phosphorylation of DDR1 is preferably phosphorylation of a tyrosine residue contained in DDR1, and particularly preferably phosphorylation of the 796th tyrosine residue in the amino acid sequence of DDR1. Phosphorylation of DDR1 is known to cause transmission of a signal indicating cell viability or cell infiltration or metastasis and the like, and an antibody that inhibits phosphorylation of DDR1 is thought to be useful as having the potential to suppress proliferation of cancer cells or their infiltration or metastasis. In the present invention, "inhibition of phosphorylation of DDR1" refers to a decrease in the proportion of phosphorylated DDR1 in cells that have been contacted with anti-DDR1 antibody compared to cells that have not been contacted with the antibody. Inhibition of phosphorylation of DDR1 can be measured with an assay system known to those skilled in the art such as western blotting using an anti-phosphotyrosine antibody. In cells in which DDR1 protein is expressed on the cell surface, phosphorylation of DDR1 is known to occur as a result of a ligand binding to the extracellular domain of DDR1, and is known to be particularly induced as a result of collagen binding to the domain as the ligand (Vogel, W., et al., Mol. Cell (1997) 1, 13-23). The collagen is suitably type I collagen or type IV collagen. Inhibition of phosphorylation of DDR1 is preferably induced as a result of anti-DDR1 antibody having inhibited binding between DDR1 and a ligand. Phosphorylation of DDR1 may be induced by autophosphorylation of DDR1 or by phosphorylation by another kinase.

Phosphorylation of DDR1 can be measured, for example, by the method indicated below. DDR1-expressing cells (such as A549, NCI-H1993, SK-MES-1, Panc-1, MFE-280, HCT-116, BT474, ZR-75-1, T47D or BxPC3) are stimulated with collagen and DDR1 protein is extracted from the cells. Phosphorylation of a tyrosine residue of the extracted DDR1 protein is confirmed by western blotting using an anti-phosphotyrosine antibody. More specifically, phosphorylation of DDR1 can be measured according to the method described in Example 5. DDR1 is known to be expressed in the aforementioned cells from the following publications (L'HOTE, C. G. M., et al., FASEB J (2002) 16, 234-6; Rikova, K., et al., Cell (2007) 131, 1190-203; and Shintani, Y., et al., J. Cell. Biol. (2008) 180, 1277-1289) and the like, and was also confirmed by the present inventors by GeneChip analysis, western blotting analysis, etc.

A preferable embodiment of the anti-DDR1 antibody provided by the present invention is anti-DDR1 antibody that is taken up into cells.

It is already known that there are phenomena in which substances present on the cell surface are actively taken up into cells via some form of mechanism. The internalization of anti-DDR1 antibody into cells is preferably induced as a result of anti-DDR1 antibody having bound to DDR1 protein expressed on the cell surface. Antibodies taken up into cells is thought to be useful as having the potential to suppress proliferation of cancer cells by conjugating with compounds having cytotoxic activity such as toxins. In the present invention, "internalization into cells" refers to when the amount of antibody taken up into cells that have been contacted with anti-DDR1 antibody is greater than when cells have been contacted with a negative control antibody. Internalization of antibody into cells can be measured as the amount of a toxin taken up into cells by directly labeling the antibody with a toxin or by allowing a secondary antibody labeled with a toxin to bind to the antibody as in Example 6. The cell phenotype is preferably one that expresses DDR1 more than ordinary cells, and such cells can be selected by gene-level analyses such as RT-PCR or GeneChip analysis using a primer specific to DDR1 gene, or by protein-level analyses such as western blotting or immunohistostaining (IHC) using an antibody specific to DDR1 protein.

A preferable embodiment of the anti-DDR1 antibody provided by the present invention is an anti-DDR1 antibody that decreases the expression level of DDR1 in cells.

A decrease in the expression level of DDR1 may be the result of promotion of decomposition of DDR1 protein or the result of suppression of translation of DDR1 protein. In addition, it may also be the result of promotion of decomposition of DDR1 mRNA or the result of suppression of transcription of DDR1 mRNA. Antibodies that decrease the expression level of DDR1 have the potential to suppress phenomena such as cell survival, infiltration, or metastasis involving DDR1 in cancer cells, and are thus thought to be useful. In the present invention, a "decrease in the expression level of DDR1" refers to a decrease in the expression level of DDR1 in cells that have been contacted with an anti-DDR1 antibody compared to cells that have not been contacted with the antibody. A decrease in the expression level of DDR1 is preferably induced as a result of anti-DDR1 antibody having bound to DDR1 on the cell surface. The amount of DDR1 mRNA can be measured with an assay system known to those skilled in the art such as RT-PCR using a primer specific for DDR1 gene. In addition, the amount of DDR1 protein can be measured with an assay system known to those skilled in the art such as western blotting using an antibody specific to DDR1 protein.

The expression level of DDR1 can be measured, for example, by the method indicated below. DDR1 protein is extracted from DDR1-expressing cells (such as A549, NCI-H1993, SK-MES-1, Panc-1, MFE-280, HCT-116, BT474, ZR-75-1, T47D or BxPC3). The extracted DDR1 protein is then detected by western blotting. More specifically, the expression level of DDR1 can be measured according to the method described in Example 7.

A preferable embodiment of the anti-DDR1 antibody provided by the present invention is anti-DDR1 antibody that decreases the expression level of TGF-β in cells.

A decrease in the expression level of TGF-β may be the result of promotion of decomposition of TGF-β protein or the result of suppression of translation of TGF-β protein. In addition, it may also be the result of promotion of decomposition of TGF-β mRNA or the result of suppression of transcription of TGF-β mRNA. TGF-β is a marker molecule the expression of which is known to rise during epithelial-mesenchymal transition (EMT) that has been reported to act to promote tumorigenesis, and an antibody that decreases the expression level of TGF-β is thought to be useful as it has the potential to inhibit tumorigenesis by suppressing epithelial-mesenchymal transition of cells. Namely, one embodiment of the anti-DDR1 antibody in the present invention may include an anti-DDR1 antibody that inhibits epithelial-mesenchymal transition (EMT) of cells. In the present invention, a "decrease in the expression level of TGF-β" refers to a decrease in the expression level of TGF-β in cells that have been contacted with an anti-DDR1 antibody compared to cells that have not been contacted with the antibody. In cells expressing DDR1 protein on the cell surface, the possibility has been suggested that DDR1-mediated expression of TGF-β is induced by collagen (Guerrot, D., et al., Am. J. Pathol. (2011) 179, 83-91). The collagen is suitably type I collagen or type IV collagen. A decrease in the expression level of TGF-β is preferably induced as a result of anti-DDR1 antibody having inhibited binding between DDR1 and collagen. The amount of TGF-β mRNA can be measured with an assay system known to those skilled in the art such as RT-PCR using a primer specific for TGF-β gene. In addition, the amount of TGF-β protein can be measured with an assay system known to those skilled in the art such as western blotting using an antibody specific to TGF-β protein.

The expression level of TGF-β can be measured, for example, by the method indicated below. DDR1-expressing cells (such as A549, NCI-H1993, SK-MES-1, Panc-1, MFE-280, HCT-116, BT474, ZR-75-1, T47D or BxPC3) are stimulated with collagen. Fibroblasts (such as MRC5) may be co-cultured at this time. RNA is then extracted from the cells and after carrying out a reverse transcription reaction to cDNA, the amount of TGF-β mRNA is measured by RT-PCR using a primer specific to TGF-β. More specifically, the expression level of TGF-β can be measured according to the method described in Example 8.

Cells in the present invention are preferably cancer cells, and more preferably cancer cells that express DDR1. The cells are particularly preferably cancer cells that express higher levels of DDR1 than normal cells. Such cells can be selected by gene-level analyses such as RT-PCR or GeneChip analysis using a primer specific to DDR1 gene, or by protein-level analyses such as western blotting or immunohistostaining (IHC) using an antibody specific to DDR1 protein.

The type of cancer of the cancer cells of the present invention is not particularly limited and include, for example, lung cancer (such as small-cell lung cancer or non-small-cell lung cancer), breast cancer, glioma, ovarian cancer, gastric cancer, pancreatic cancer, esophageal cancer, endometrial cancer, bile duct cancer, colorectal cancer, liver cancer, leukemia, lymphoma, renal cancer, prostate cancer, melanoma, thyroid cancer, bladder cancer, and osteosarcoma. Preferable examples include lung cancer (non-small-cell lung cancer), breast cancer, glioma, ovarian cancer, gastric cancer, pancreatic cancer, esophageal cancer, endometrial cancer, and bile duct cancer.

The present invention provides the antibodies described in (a) to (c) below:

(a) an antibody having an amino acid sequence identical to an antibody produced from the hybridoma deposited under Accession No. FERM BP-11399 (#115), (b) an antibody having an amino acid sequence identical to an antibody produced from the hybridoma deposited under Accession No. FERM BP-11398 (#27), and (c) an antibody having an amino acid sequence identical to an antibody produced from the hybridoma deposited under Accession No. FERM BP-11397 (#24).

Each of the aforementioned hybridomas has been deposited in an international depository as indicated below. The following describes the contents specifying the international deposition of each hybridoma. Operations and services of the following depository institution (International Patent Organism Depository, National Institute of Advanced Industrial Science and Technology) were taken over by the National Institute of Technology and Evaluation (NITE) as of Apr. 1, 2012.

(a) #115

(1) Name and address of depository institution:
Name: International Patent Organism Depository, National Institute of Advanced Industrial Science and Technology
Address: Tsukuba Central 6, 1-1-1 Higashi, Tsukuba, Ibaraki, Japan 305-8566
(2) Acceptance date (deposition date): Jul. 22, 2011
(3) Accession no.: FERM BP-11399
(4) Identifying indication made by depositor: DDR1 hybridoma #115 110627

(b) #27

(1) Name and address of depository institution:
Name: International Patent Organism Depository, National Institute of Advanced Industrial Science and Technology
Address: Tsukuba Central 6, 1-1-1 Higashi, Tsukuba, Ibaraki, Japan 305-8566
(2) Acceptance date (deposition date): Jul. 22, 2011
(3) Accession no.: FERM BP-11398
(4) Identifying indication made by depositor: DDR1 hybridoma #27 110629

(c) #24

(1) Name and address of depository institution:
Name: International Patent Organism Depository, National Institute of Advanced Industrial Science and Technology
Address: Tsukuba Central 6, 1-1-1 Higashi, Tsukuba, Ibaraki, Japan 305-8566
(2) Acceptance date (deposition date): Jul. 22, 2011
(3) Accession no.: FERM BP-11397
(4) Identifying indication made by depositor: DDR1 hybridoma #24 110629

As will be subsequently described in the examples, the antibodies described in (a) to (c) above are all antibodies that bind to the stalk domain of DDR1. Those skilled in the art are able to determine the nucleotide sequences and amino acid sequences of antibodies produced from hybridomas using methods described in the subsequent examples, and are able to produce recombinant antibodies using known genetic engineering techniques based on those sequences.

In addition, the present invention provides antibodies having a CDR sequence that is identical to a CDR sequence of the antibodies described in (a) to (c) above. Antibodies contain six CDRs, which are H chain CDR1, CDR2, and CDR3 and L chain CDR1, CDR2, and CDR3, and only one of these CDRs is required to be identical, more preferably the three CDRs of the H chain or the three CDRs of the L chain are identical, and even more preferably all six CDRs are identical. Those skilled in the art are able to produce an antibody having binding activity to the stalk domain of DDR1 that is roughly equivalent to the binding activity of the aforementioned antibodies by transplanting a CDR of any of the antibodies described in (a) to (c) above into another suitable antibody (CDR transplantation antibody); such an antibody is useful in the same manner as the aforementioned antibodies. The locations and numbering system used for antibody CDR domains and FR domains are defined according to, for example, the definitions of Kabat (Kabat, E. A., et al. (1991) Sequences of Proteins of Immunological Interest, Fifth Edition, U.S. Department of Health and Human Services, U.S. Government Printing Office).

The present invention provides antibodies that compete for binding to DDR1 with an antibody of the present invention.

In the present invention, "competing for binding to DDR1" refers to a decrease in DDR1 binding activity of an antibody of the present invention when in the presence of a certain anti-DDR1 antibody in an assay system used to measure antibody binding to DDR1. Since such an antibody is thought to be an antibody that binds to an antigenic determinant (epitope) that is identical to that of the antibody of the present invention or is extremely close in proximity to the epitope of the antibody of the present invention, it is useful similarly to the antibody of the present invention. Here, the full length of DDR1 protein or the extracellular domain of DDR1 protein may be used to measure binding to DDR1. In addition, the stalk domain of DDR1 protein may also be used.

Competition for binding to DDR1 can be measured with an assay system known to those skilled in the art such as a cross-blocking assay. For example, a competitive ELISA assay using an enzyme label is a preferable cross-blocking assay. Competition for binding to DDR1 can be measured, for example, by the method indicated below. After incubating DDR1 protein coated onto the wells of a microtiter plate in the presence or absence of a test antibody, anti-DDR1 antibody is added to the wells of the microtiter plate. If the test antibody and the anti-DDR1 antibody competed for the binding to DDR1, the amount of anti-DDR1 antibody that binds to DDR1 protein in the wells will decrease. The amount of bound antibody can be easily measured by preliminarily labeling the anti-DDR1 antibody. For example, the amount of bound antibody can be measured by labeling the anti-DDR1 antibody with biotin and using an avidin-peroxidase conjugate along with a suitable substrate. Alternatively, the amount of bound antibody can be measured by radioactive labeling or fluorescent labeling of the anti-DDR1 antibody.

Moreover, when the test antibody and anti-DDR1 antibody have constant regions derived from different animal species, the amount of bound antibody can be measured with a labeled antibody that specifically recognizes the constant region of antibody derived from those animal species. Alternatively, in the case of different subclasses even if the antibody is derived from the same animal species, the amount of bound antibody can be measured with a labeled antibody that specifically recognizes each subclass.

The present invention provides antibodies that bind to an epitope same as that to which an antibody of the present invention binds.

Antibody epitopes can be identified by the method of synthesizing a group of peptides (e.g., a peptide array) that cover the amino acid sequence of an antigen by mutual overlapping, and measuring binding activity of antibodies to each of the peptides (Poetz, O., et al., Proteomics (2005) 5, 2402-11). Alternatively, identification can also be made by methods such as antigen-antibody crystal structure analysis (Vyas, N. K., et al., Biochemistry (2004) 41, 13575-86), the method of measuring binding activity of an antibody to various mutants by producing a group of mutant proteins in which amino acids of an antigen amino acid sequence have been substituted with alanine one amino acid at a time (alanine scanning, Cunningham, B. C. and Wells, J. A., Science (1989) 244, 1081-5), and the method of screening for peptide sequences that bind to antibodies in a phage library presenting random peptides and antigen partial peptides (Smith, G. P. and Petrenko, V. A., Chem. Rev. (1997) 97, 391-410). When an epitope identified in this manner is identical to an epitope to which an antibody of the present invention binds or is in extremely close proximity to an epitope to which the antibody of the present invention binds, since an antibody that binds to that epitope is considered to have binding activity equivalent to that of the antibody of the present invention, it is useful similarly to the antibody of the present invention. An "epitope in extremely close proximity" means that the difference in the location of the epitope is preferably within five amino acids, more preferably within four amino acids, even more preferably within three amino acids, particularly preferably within two amino acids, and most preferably one amino acid.

An antibody that binds to an epitope to which an antibody of the present invention binds can be obtained by a method known to those skilled in the art. For example, the antibody can be obtained by a method comprising determining an epitope to which an antibody of the present invention binds using the aforementioned method, and producing an antibody by using a polypeptide having an amino acid sequence contained in that epitope as an immunogen, or by a method comprising determining an epitope of an antibody produced according to ordinary methods and selecting an antibody which binds to the same epitope as an antibody of the present invention does.

The present invention provides antibodies in which one or more amino acids in the antibody of the present invention have been added, deleted and/or substituted with other amino acids, and which have a binding activity to the stalk domain of DDR1, which binding activity is equivalent to that of the antibody prior to the addition, deletion and/or substitution.

In the present invention, "having equivalent binding activity to the stalk domain of DDR1" refers to binding activity to the stalk domain of DDR1 of an antibody in which one or more amino acids have been added, deleted and/or substituted with other amino acids being preferably 70% or more, more preferably 80% or more, even more preferably 90% or more, and most preferably 95% or more compared to that of the antibody prior to the addition, deletion and/or substitution. Since such an antibody is thought to have nearly the same properties as the antibody of the present invention, it is useful in the same manner as an antibody of the present invention.

Addition, deletion and/or substitution of amino acids can be carried out in accordance with techniques known to those skilled in the art, an example of which is site-specific mutagenesis (Hashimoto-Gotoh, T., et al., Gene (1995) 152, 271-275; Zoller, M. J. and Smith, M., Methods Enzymol. (1983) 100, 468-500; Kramer, W., et al., Nucleic Acids Res. (1987) 12, 9441-9456; Kramer W. and Fritz H. J., Methods Enzymol (1987) 154, 350-367; Kunkel, T. A., Proc. Natl. Acad. Sci. USA (1985) 82, 488-492). It is already known that even in a protein in which one or more amino acids were added, deleted and/or substituted compared to a certain protein, the biological activity of the protein is maintained (Mark, D. F., et al., Proc. Natl. Acad. Sci. USA (1984) 81, 5662-5666; Wang, A., et al., Science (1984) 224, 1431-1433).

When carrying out amino acid substitution, an amino acid is preferably substituted with a different amino acid that maintains the properties of an amino acid side chain. Examples of amino acid substitutions that maintain the properties of an amino acid side chain include amino acid substitutions within each of the groups of hydrophobic amino acids (A, I, L, M, F, P, W, Y and V), hydrophilic amino acids (R, D, N, C, E, Q, G, H, K, S and T), amino acids having an aliphatic side chain (G, A, V, L, I and P), amino acids having a hydroxyl group-containing side chain (S, T and Y), amino acids having a sulfur atom-containing side chain (C and M), amino acids having a carboxylic acid and amide-containing side chain (D, N, E and Q), amino acids having a base-containing side chain (R, K and H), and amino acids having an aromatic group-containing side chain (H, F, Y and W).

There are no particular limitations on the amino acid position where addition, deletion, and/or substitution are carried out, and addition, deletion, and/or substitution are preferably carried out on amino acids not involved in antigen binding or maintaining antibody structure. When an antibody is divided into constant regions and variable regions, such a position within the constant regions can be easily specified by those skilled in the art. Moreover, when the variable regions are divided into framework regions and CDR regions, such a position within the framework regions can be specified without excessive burden by those skilled in the art. Such a position can also be specified in CDR regions by those skilled in the art.

The antibody of the present invention may be a polyclonal antibody or a monoclonal antibody, and is preferably a monoclonal antibody. A monoclonal antibody can be acquired using known techniques such as the hybridoma method comprising immunizing an animal with an antigen, or the phage display method comprising screening an antibody library. The monoclonal antibody of the present invention includes not only antibodies obtained from a clone derived from antibody-producing cells such as hybridomas, but also includes humanized antibodies and chimeric antibodies not derived from hybridomas.

There are no particular limitations on the antibody subclass. IgG, IgM, IgA, IgD, or IgE are preferable, and IgG is more preferable.

In the hybridoma method, monoclonal antibody can be acquired, for example, in the manner described below. First, a DDR1 protein serving as antigen is prepared and this is used to immunize an animal in accordance with ordinary immunization methods. Immune cells obtained from the immunized animal are fused with known parent cells in accordance with ordinary cell fusion methods to obtain hybridomas. A hybridoma that produces the target anti-DDR1 antibody is then selected from the resulting hybridomas by ordinary screening methods. More specifically, monoclonal antibody can be acquired according to the method described in Example 1.

A monoclonal antibody is produced, for example, in the following manner. First, DDR1 protein used as sensitizing antigen for acquiring the antibody can be obtained by expressing DDR1 gene. The nucleotide sequence of human DDR1 gene is already known (GenBank Accession No. NM_013993). Namely, after inserting the gene sequence encoding DDR1 into a known expression vector and transforming suitable host cells, the target DDR1 protein can be purified by known methods from the host cells or culture supernatant thereof. In addition, a purified native DDR1 protein can also be used in the same manner. Purified native DDR1 protein can be generated by carrying out purification using several chromatographic procedures, such as ordinary ion chromatography or affinity chromatography, once or multiple times, either alone or in combination. In addition, a fusion protein can be used as an immunogen by fusing a partial polypeptide containing at least a portion of the stalk domain of DDR1 with a different polypeptide. An antibody Fc fragment or peptide tag, or the like, can be used to produce a fusion protein for use as an immunogen. A vector that expresses a fusion protein can be produced by fusing two or more types of desired genes encoding polypeptide fragments in frame and inserting the fused genes into an expression vector, as previously described. Methods of preparing fusion proteins are described in Molecular Cloning, 2nd edition (Sambrook J. et al., Molecular Cloning 2nd ed. (1989)9.47-9.58, Cold Spring Harbor Lab. Press). DDR1 protein purified in this manner can be used as a sensitizing antigen for the immunization of a mammal.

Moreover, a peptide having the sequence of entire stalk domain of DDR1 or containing at least its five consecutive amino acids can be preferably used as a partial peptide. Sequences containing at least five consecutive amino acids refer to those preferably containing six or more and more preferably eight or more consecutive amino acids. In addition, sequences containing at least five or more consecutive amino acids refer to amino acid sequences that are specific to the stalk domain of DDR1 and have antigenicity.

There are no particular limitations on the mammal immunized with the sensitizing antigen. To obtain a monoclonal antibody by cell fusion, it is preferable to select an animal to be immunized after consideration of its compatibility with the parent cells used for the cell fusion. Specifically, mice, rats, hamsters, rabbits, chickens, and monkeys can be used for as the immunized animal. Among them, rodents such as mice, rats, and hamsters are preferable as the immunized animal.

The animal described above can be immunized with a sensitizing antigen using known methods. For example, in a typical method, the mammal is immunized by injecting the sensitizing antigen intraperitoneally or subcutaneously. Specifically, the sensitizing antigen is administered to a mammal several times every four to 21 days. The sensitizing antigen is used for immunization after dilution to a suitable dilution ratio with phosphate-buffered saline (PBS), physiological saline, or the like. The sensitizing antigen can also be administered with an adjuvant. For example, it can be mixed with Freund's complete adjuvant and emulsified for use as the sensitizing antigen. A suitable carrier can also be used when immunizing with the sensitizing antigen. In particular, when a partial peptide with a low molecular weight is used as the sensitizing antigen, it is desirable to bind the sensitizing antigen to a carrier protein, such as albumin, keyhole limpet hemocyanin, and the like, for immunization.

After the mammal has been immunized in this manner and it has been confirmed that the level of the desired antibody in the serum has increased, the immune cells are harvested from the mammal and used for cell fusion. In particular, spleen cells can be used preferably as the immune cells.

Mammalian myeloma cells are used as the cells to be fused with the immune cells. The myeloma cells preferably have a suitable selection marker for screening. A selection marker refers to a trait that allows cells to live (or not) under certain culture conditions. Known selection markers include hypoxanthine-guanine phosphoribosyl transferase deficiency (hereinafter abbreviated to "HGPRT deficiency") and thymidine kinase deficiency (hereinafter abbreviated to "TK deficiency"). Cells deficient in HGPRT or TK are hypoxanthine-aminopterin-thymidine sensitive (hereinafter abbreviated to "HAT sensitivity"). HAT-sensitive cells are unable to synthesize DNA and die in HAT selection medium. However, when fused with normal cells, they can continue to synthesize DNA using the salvage pathway of normal cells and therefore they begin to grow in HAT selection medium.

HGPRT-deficient cells and TK-deficient cells can both be selected with a medium containing 6-thioguanine, 8-azaguanine (hereinafter abbreviated to "8AG") or 5'-bromodeoxyuridine. Although normal cells die as a result of incorporating these pyrimidine analogs into their DNA, cells deficient in these enzymes are unable to incorporate these pyrimidine analogs and can thus survive in the selection medium. A selection marker referred to as G418 resistance also imparts resistance to 2-deoxystreptamine-type antibiotics (gentamycin analogs) because it is a neomycin-resistance gene. Various myeloma cells that are suitable for cell fusion are known, and examples of myeloma cells that can be used include P3 (P3x63Ag8.653) (J. Immunol. (1979)123, 1548-1550), P3x63Ag8U.1 (Current Topics in Microbiology and Immunology (1978)81, 1-7), NS-1 (Kohler G.& Milstein C., Eur. J. Immunol. (1976)6, 511-519), MPC-11 (Margulies D. H. et al., Cell (1976)8, 405-415), SP2/0 (Shulman M. et al., Nature (1978)276, 269-270), FO (de St. Groth S. F. et al., J. Immunol. Methods (1980)35, 1-21), 5194 (Trowbridge I. S. J., Exp. Med. (1978)148, 313-323), and R210 (Galfre G. et al., Nature (1979)277, 131-133).

The fusion of the aforementioned immune cells and myeloma cells can be carried out according to known methods, such as the method of Kohler and Milstein (Kohler G. & Milstein C., Methods Enzymol. (1981)73, 3-46).

More specifically, the aforementioned cell fusion can be carried out in an ordinary nutritive culture medium in the presence of a cell fusion promoter. Examples of cell fusion promoters that can be used include polyethylene glycol (PEG) and Sendai virus (HVJ). An auxiliary agent, such as dimethylsulfoxide, can also be added as desired to further enhance the fusion efficiency.

The ratio in which the immune cells and myeloma cells are used can be set arbitrarily. For example, there are preferably 1-10 times more immune cells than myeloma cells. Examples of culture media that can be used for the cell fusion described above include MEM and RPMI1640 culture medium, preferably used for the growth of the aforementioned myeloma cell lines, as well as ordinary culture medium used for this type of cell culture. A serum supplement, such as fetal calf serum (FCS), can also be added to the culture medium.

Cell fusion is carried out to form target fused cells (hybridomas) by thoroughly mixing predetermined amounts of the immune cells and myeloma cells in the culture medium and then mixing in PEG solution, prewarmed to about 37° C. During cell fusion, PEG, with an average molecular weight of about 1000-6000, for example, can normally be added at a concentration of 30%-60% (w/v). Subsequently, the cell fusion agents and other agents not amenable to hybridoma growth are removed by the repeated sequential addition of a suitable culture medium, as indicated above, centrifugation, and the removal of the supernatant.

The hybridomas thus obtained can be selected with a selective culture medium corresponding to the selection marker possessed by the myeloma used for cell fusion. For example, HGPRT- or TK-deficient cells can be selected by culture in HAT culture medium (culture medium containing hypoxanthine, aminopterin, and thymidine). When HAT-sensitive myeloma cells are used for cell fusion, those cells that have successfully fused with normal cells can be selectively grown in HAT culture medium. Culture in HAT medium is continued for an adequate amount of time for cells other than the target hybridomas (nonfused cells) to die. Specifically, the target hybridomas can generally be selected by culture for several days to several weeks. Next, screening and monocloning for a hybridoma that produces the target antibody can be performed with an ordinary limiting dilution method.

Screening and monocloning for a target antibody is preferably carried out with a known screening method based on an antigen-antibody reaction. For example, an antigen is bound to a carrier, such as polystyrene beads or a commercially available 96-well microtiter plate, and reacted with the culture supernatant of the hybridoma. The carrier is then washed, and reacted with an enzyme-labeled secondary antibody or the like. When an antibody that reacts with the sensitizing antigen is present in the culture supernatant, the secondary antibody binds to the carrier through this antibody. Finally, whether or not the target antibody is present in the culture supernatant can be determined by detecting the secondary antibody bound to the carrier. A hybridoma producing the desired antibody, which can bind to the antigen, can be cloned by a method such as limiting dilution. At this time, the antigen used for immunization or a substantially equivalent DDR1 protein can be used preferentially as the antigen.

In addition to the method for producing a hybridoma by immunizing an animal other than a human with an antigen, a target antibody can also be obtained by sensitizing human lymphocytes with the antigen. Specifically, human lymphocytes are first sensitized with DDR1 protein in vitro. The immunosensitized lymphocytes are then fused to a suitable fusion partner. Myeloma cells of human origin, with the ability to divide continuously, for example, can be used as the fusion partner (see Japanese Patent Application Kokoku Publication No. (JP-B) H1-59878 (examined, approved Japanese patent application published for opposition)). An anti-DDR1 antibody produced with this method is a human antibody with binding activity for DDR1 protein.

An anti-DDR1 human antibody can also be obtained by immunizing DDR1 protein as the antigen to a transgenic animal with the entire repertoire of human antibody genes. Antibody-producing cells of the immunized animal can be immortalized by treatments such as fusion with a suitable fusion partner or infection with Epstein-Barr virus. A human antibody can also be isolated from immortalized cells obtained in this manner (WO 94/25585, WO 93/12227, WO 92/03918, and WO 94/02602). Cells producing antibodies with target reaction specificity can also be cloned by cloning the immortalized cells. When using a transgenic animal as the immunized animal, the immune system of the animal recognizes human DDR1 as foreign. Thus, a human antibody directed against human DDR1 can easily be obtained.

A hybridoma producing a monoclonal antibody prepared in this manner can be subcultured in ordinary culture medium. The hybridoma can also be stored for an extended period of time in liquid nitrogen. The hybridoma can be cultured in accordance with ordinary methods to obtain the target monoclonal antibody from its culture supernatant. Alternatively, the monoclonal antibody can be produced by administering the hybridoma to a mammal compatible with it to allow the hybridoma to grow, using the resulting ascites as the monoclonal antibody. The former method is suitable for obtaining highly pure antibody.

In the present invention, an antibody encoded by antibody genes cloned from antibody-producing cells can also be used. Cloned antibody genes can be expressed as antibody by incorporating them in a suitable vector and introducing the vector into a host. Methods for isolating the antibody genes, introducing them into a vector, and transforming host cells with it have already been established (Vandamme, A. M. et al., Eur. J. Biochem. (1990) 192, 767-775).

For example, a cDNA encoding a variable region (V region) of the anti-DDR1 antibody can be obtained from hybridoma cells producing the anti-DDR1 antibody. To accomplish this, total RNA is usually first extracted from the hybridoma. Examples of methods for extracting total RNA from cells include guanidine ultracentrifugation (Chirgwin, J. M. et al., Biochemistry (1979) 18, 5294-5299) and the AGPC method (Chomczynski, P. et al., Anal. Biochem. (1987) 162, 156-159).

mRNA can be purified from the extracted total RNA using an mRNA Purification Kit (GE Healthcare) and the like. Alternatively, kits such as the QuickPrep mRNA Purification Kit (GE Healthcare) are commercially available for the extraction of mRNAs directly from cells. These kits can be used to obtain mRNAs from a hybridoma. The cDNA encoding an antibody V region can be synthesized from the resulting mRNAs using reverse transcriptase. The cDNA can be synthesized with, for example, the AMV Reverse Transcriptase First-strand cDNA Synthesis Kit (Seikagaku Corp.). The 5'-Ampli FINDER RACE Kit (Clontech) and 5'-RACE method using PCR (Frohman, M. A. et al., Proc. Natl Acad. Sci. U.S.A. (1988) 85, 8998-9002, Belyaysky, A. et al., Nucleic Acids Res. (1989) 17, 2919-2932) can be used to synthesize and amplify the cDNA. Suitable restriction sites, described below, can also be introduced at both ends of the cDNA during the course of cDNA synthesis.

Target cDNA fragments are purified from the resulting PCR product and linked to vector DNA. A recombinant vector is thus prepared, and after its introduction into *Escherichia coli* or the like and the selection of colonies, the desired recombinant vector can be prepared from the *E. coli* that formed colonies. Whether or not the recombinant vector has the nucleotide sequences of the target cDNA can be confirmed by a known method, such as dideoxynucleotide chain termination sequencing.

PCR using a primer that amplifies a variable region gene can also be used to obtain a gene encoding a variable region. First, cDNA is synthesized using the extracted mRNA as the template to construct a cDNA library. It is convenient to use a commercially available kit to synthesize the cDNA library. Because the amount of mRNA obtained from only a small number of cells is extremely small, its direct purification results in a low yield. Thus, mRNA is normally purified after the addition of a carrier RNA that clearly does not contain any antibody gene. Alternatively, when it is possible to extract a certain amount of RNA, RNA from only antibody-producing cells can be efficiently extracted. For example, the addition of carrier RNA may not be necessary for the extraction of RNA from 10 or more, 30 or more, or preferably 50 or more antibody-producing cells.

The antibody gene is then amplified by PCR using the cDNA library thus constructed as the template. Primers for amplifying the antibody genes by PCR are known. For example, primers to amplify human antibody genes can be designed based on, for example, J. Mol. Biol. (1991) 222, 581-597. These primers have nucleotide sequences that differ for each immunoglobulin subclass. Thus, when a cDNA library of an unknown subclass is used as the template, PCR is performed with all possibilities considered.

For example, when a gene encoding human IgG is to be obtained, primers that amplify a gene encoding γ1 to γ5 as heavy chains and κ and λ, chains as light chains can be used. To amplify a variable region gene of IgG, a primer that anneals to a sequence corresponding to the hinge region is typically used for the primer on the 3' side. Conversely, a primer corresponding to each subclass can be used for the primer on the 5' side.

The PCR products amplified with primers that amplify the genes of each subclass of heavy chains and light chains are made into independent libraries. The use of a library synthesized in this manner makes it possible to reconstitute immunoglobulins comprised of combinations of heavy chains and light chains. A target antibody can then be screened for using the binding activity of the reconstituted immunoglobulins to antigens as an indicator.

After a cDNA encoding a V region of the target antibody is obtained, the cDNA is digested with a restriction enzyme that recognizes a restriction site inserted into both ends of the cDNA. A preferred restriction enzyme recognizes and digests a nucleotide sequence that is unlikely to occur in the nucleotide sequence constituting the antibody gene. A restriction enzyme that imparts a cohesive end is preferable when inserting a single copy of the digested fragment into a vector in the proper direction. An antibody expression vector can be generated by inserting the cDNA encoding V regions of the antibody, digested as described above, into a suitable expression vector. At this time, a chimeric antibody can be produced by fusing in frame genes encoding an antibody constant region (C region) and genes encoding the V region described above. Herein, "chimeric antibody" refers to an antibody containing constant and variable regions derived from different organisms. Thus, xenogeneic chimeric antibodies, such as mouse-human antibodies and human-human allogeneic chimeric antibodies, are included in the chimeric antibodies of the present invention. A chimeric antibody expression vector can also be constructed by inserting the V region genes into an expression vector that originally had constant regions.

Specifically, the recognition sequence of a restriction enzyme that digests the V region gene can be arranged on the 5' side of an expression vector retaining a DNA encoding the desired antibody constant region (C region). A chimeric antibody expression vector is constructed by digesting the two with the same combination of restriction enzymes and then fusing them in frame.

Antibody genes can be incorporated into an expression vector for expression under the control of an expression control domain to produce the antibody of the present invention. An expression control domain for expressing antibody can include, for example, an enhancer and a promoter. Recombinant cells expressing DNA encoding the antibody can then be obtained by transforming suitable host cells with this expression vector.

In the expression of antibody genes, DNAs encoding the antibody heavy chain (H chain) and light chain (L chain) can each be incorporated into different expression vectors. Vectors incorporating either the H chain or the L chain can express an antibody molecule with the H chain and L chain after the vectors are simultaneously transformed (cotransfected) into the same host cell. Alternatively, DNAs encoding H chain and L chain can be incorporated in a single expression vector to transform host cells (WO 94/11523).

Many combinations of hosts and expression vectors are known for expressing antibodies. All of these expression systems can be applied to the present invention. Animal cells, plant cells, or fungal cells can be used when eukaryotic cells are used as hosts. Specific examples of animal cells that can be used in the present invention include mammalian cells (such as CHO, COS, 3T3, myeloma, BHK [baby hamster kidney], Hela, C127, HEK293, Bowes melanoma cells, and Vero cells), amphibian cells (such as *Xenopus* oocytes), and insect cells (such as *Drosophila* S2, sf9, sf21, and Tn5 cells).

Known examples of plant cells used in antibody gene expression systems are cells from the genus *Nicotiana*, such as *Nicotiana tabacum*. Callus-cultured cells can be used for plant cell transformation.

Examples of fungal cells that can be used include those of yeast (the genus *Saccharomyces*, such as *Saccharomyces cerevisiae* and *Saccharomyces pombe*, and the methanol-utilizing yeast genus *Pichia*, such as *Pichia pastoris*) and of filamentous fungi (the genus *Aspergillus*, such as *Aspergillus niger*).

Antibody gene expression systems that use prokaryotic cells are also known. For example, cells of bacteria such as *E. coli, Streptococcus, Staphylococcus, Streptomyces*, or *Bacillus subtilis* can be used in the present invention.

When using mammalian cells, an expression vector can be constructed in which a routinely used useful promoter, the antibody genes to be expressed, and a polyA signal at the 3' side downstream from it are operably linked. An example of a promoter/enhancer is human cytomegalovirus immediate early promoter/enhancer.

Other examples of promoter/enhancers that can be used to express an antibody of the present invention include viral promoter/enhancers or mammalian cell promoter/enhancers, such as human elongation factor 1α (HEF1α). Specific examples of viruses whose promoter/enhancers are useful include retroviruses, polyomaviruses, adenoviruses, and simian virus 40 (SV40).

When using an SV40 promoter/enhancer, the method of Mulligan et al. can be used (Nature (1979) 277, 108). An HEF1α promoter/enhancer can also be used to easily express a target gene with the method of Mizushima et al. (Nucleic Acids Res. (1990) 18, 5322).

With *E. coli*, antibody genes can be expressed by operably linking a routinely used useful promoter, an antibody secretion signal sequence, and the antibody genes to be expressed. Examples of promoters include the lacZ promoter and the araB promoter. When using the lacZ promoter, the method of Ward et al. can be used (Nature (1989) 341, 544-546; FASEB J. (1992) 6, 2422-2427). Alternatively, the araB promoter can be used to express target genes according to the method of Better et al. (Science (1988) 240, 1041-1043).

An example of the antibody secretion signal sequence that can be used for the production into the periplasm of *E. coli* is the pelB signal sequence (Lei, S. P. et al., J. Bacteriol. (1987) 169, 4379). The antibody produced in the periplasm is separated and then structurally refolded using a protein denaturant such as a guanidine hydrochloride or urea so that the antibody has the desired binding activity.

Examples of useful replication origins that can be inserted into an expression vector include those originating in SV40, polyomaviruses, adenoviruses, and bovine papillomavirus (BPV). A selection marker can also be inserted into the expression vector to amplify the number of gene copies in a host cell system. Specific examples of selection markers that can be used include the aminoglycoside transferase (APH) gene, the thymidine kinase (TK) gene, the *E. coli* xanthine-guanine phosphoribosyl transferase (Ecogpt) gene, and the dihydrofolate reductase (dhfr) gene.

A target antibody is produced by introducing these expression vectors into host cells and culturing the transformed host cells in vitro or in vivo. Culture of the host cells is carried out in accordance with known methods. Examples of culture media that can be used include DMEM, MEM, RPMI1640, and IMDM, and these can be used in combination with a serum supplement such as FCS. The present invention relates to antibodies produced by culturing host cells that have been transformed in this manner. This includes, for example, an antibody that has been collected from a culture supernatant and the like after having cultured transformed host cells.

In addition, the present invention provides a method for producing an antibody that comprises a step of culturing transformed host cells and collecting antibody. When the antibody of the present invention is secreted into a culture medium or culture supernatant, collection of antibody in this production method comprises collection of the culture medium or culture supernatant. When the antibody of the present invention is produced within cells, the antibody is collected after having first lysed the cells.

In addition, mammals or insects can also be used to produce a recombinant antibody in addition to the aforementioned host cells. Examples of mammals that can be used include goats, pigs, sheep, mice, and cows (Vicki Glaser, SPECTRUM Biotechnology Applications (1993)). In addition, when using a mammal, transgenic animals can be used. Namely, the antibody can be acquired from an animal inserted with a gene that encodes a target antibody. For example, an antibody gene can be constructed in the form of a fused gene by in-frame insertion into a gene that encodes a protein inherently produced in milk. Goat β-casein, for example, can be used as protein secreted into milk. A DNA fragment containing the fused gene inserted with the antibody gene is injected into a goat embryo and the injected embryo is introduced into a female goat. The desired antibody can be acquired in the form of a fusion protein with milk protein from milk produced by the transgenic goat (or offspring thereof) born from the goat that received the embryo. In addition, hormones can be suitably used in the transgenic goat to increase the amount of milk containing the desired antibody produced by the transgenic goat (Ebert, K. M., et al., Bio/Technology (1994) 12, 699-702).

In addition, a silkworm, for example, can be used as an insect for producing the antibody of the present invention. When using a silkworm, the target antibody can be obtained from the body fluid of the silkworm by infecting the silkworm with Baculovirus inserted with a nucleic acid encoding the target antibody (Susumu, et al., Nature (1985) 315, 592-4).

Moreover, a tobacco plant, for example, can be used when using a plant to produce the antibody of the present invention. In the case of using a tobacco plant, a nucleic acid encoding the target antibody is inserted into a plant expression vector such as pMON530, and this vector is inserted into bacteria such as *Agrobacterium tumefaciens*. The desired antibody can be obtained from the leaves of the tobacco plant by infecting a tobacco plant such as *Nicotiana tabacum* with the bacteria (Ma, et al., Eur. J. Immunol. (1994) 24, 131-8).

The antibody expressed and produced as previously described can be isolated from within host cells or outside host cells (such as in a culture medium or milk) and then purified in the form of a substantially pure, homogeneous antibody. Antibody separation and purification can be carried out by using known methods ordinarily used to purify protein, either alone or in suitable combinations. For example, the antibody can be separated and purified by suitably selecting and combining methods such as ammonium sulfate or ethanol precipitation, acid extraction, chromatographic column, filter, ultrafiltration, salting out, solvent precipitation, solvent extraction, distillation, immunoprecipitation, SDS-polyacrylamide gel electrophoresis, isoelectric focusing electrophoresis, dialysis, or recrystallization (Harlow, E. and Lane, D., Antibodies: A Laboratory Manual (1988), Cold Spring Harbor Laboratory).

Examples of chromatography include affinity chromatography, ion exchange chromatography such as anion or cation exchange chromatography, phosphocellulose chromatography, hydrophobic (interaction) chromatography, gel filtration, reverse phase chromatography, adsorption chromatography, hydroxyapatite chromatography, and lectin chromatography (Strategies for Protein Purification and Characterization: A Laboratory Course Manual, ed. Daniel R. Marshak, et al. (1996), Cold Spring Harbor Laboratory Press). These chromatography procedures can be carried out using liquid phase chromatography such as HPLC or FPLC. Examples of columns used in affinity chromatography include a protein A column and protein G column. Examples of protein A columns include Hyper D, POROS, and Sepharose F.F. (manufactured by Pharmacia).

An antibody can be arbitrarily modified or partially removed of peptide by allowing a suitable protein-modifying enzyme to act thereon either before or after purification, as necessary. Examples of protein-modifying enzymes include trypsin, chymotrypsin, lysyl endopeptidase, protein kinase, and glucosidase.

A C region originating in an animal antibody can be used for the C region of a recombinant antibody of the present invention. Examples of useful mouse antibody H chain C regions include Cγ1, Cγ2a, Cγ2b, Cγ3, Cμ, Cδ, Cα1, Cα2, and Cε, and examples of L chain C regions include Cκ and Cλ. Examples of useful animal antibodies other than mouse antibodies include rat, rabbit, goat, sheep, camel, and monkey antibodies. The sequences of these antibodies are known. The C region can also be modified to improve the stability of the antibody or its production. In the present invention, when administering the antibody to a human, an artificially modified recombinant antibody can be made in order to, for example, lower its antigenicity in humans. Examples of recombinant antibodies include chimeric antibodies and humanized antibodies.

These modified antibodies can be produced using known methods. Chimeric antibodies refer to antibodies in which variable regions and constant regions of different origins are linked. For example, an antibody with heavy chain and light chain variable regions of a mouse antibody and heavy chain and light chain constant regions of a human antibody is a mouse-human xenogeneic chimeric antibody. A recombinant vector expressing a chimeric antibody can be prepared by linking inframe DNA encoding variable regions of a mouse antibody with a DNA encoding a constant region of a human antibody and then incorporating it into an expression vector. Recombinant cells transformed with the vector are cultured and the incorporated DNAs are expressed to obtain the chimeric antibody produced in a culture. C regions of a human antibody may be used as the C regions of chimeric antibodies and humanized antibodies. For example, Cγ1, Cγ2, Cγ3, Cγ4, Cμ, Cδ, Cα1, Cα2, and Cε can be used for the C region in H chains. Cκ and Cλ can be used for the C region in L chains. The amino acid sequences of these C regions and the nucleotide sequences that encode them are known. A human antibody C region can also be modified to improve the stability of the antibody itself or the antibody production.

In general, chimeric antibodies are composed of V regions originating from antibodies of an animal other than a human and C regions originating from human antibodies. In contrast, humanized antibodies are composed of complementarity determining regions (CDRs) originating from antibodies of animals other than humans, framework regions (FRs) originating from human antibodies, and C regions originating from human antibodies. Because humanized antibodies have reduced immunogenicity in the human body, they are useful as an active ingredient of a therapeutic agent of the present invention.

Antibody variable regions are normally composed of three complementarity determining regions (CDRs) flanked by four framework regions (FRs). A CDR is substantially a region that determines the binding specificity of an antibody. The amino acid sequences of CDRs are rich in diversity. Conversely, the amino acid sequences that constitute FRs often demonstrate high homology, even among antibodies with different binding specificities. Consequently, it is generally considered that the binding specificity of a certain antibody can be grafted onto another antibody by grafting the CDRs.

A humanized antibody is also referred to as a "reshaped" human antibody. Specifically, humanized antibodies in which the antibody CDRs of an animal other than a human, such as a mouse, have been grafted onto human antibodies, are known. General genetic recombination techniques for producing humanized antibodies are also known.

A specific example of a known method of grafting the CDRs of a mouse antibody to human FRs is overlap extension PCR. In the overlap extension PCR, a nucleotide sequence encoding a CDR of the mouse antibody to be grafted is added to primers used to synthesize a human antibody FR. Primers are prepared for each of the four FRs. In general, it is considered to be advantageous in terms of maintaining the CDR function to select a human FR with high homology to the mouse FR when grafting a mouse CDR onto a human FR. That is, it is generally preferable to use a human FR with an amino acid sequence with high homology to the amino acid sequence of the FR adjacent to the mouse CDR to be grafted.

The nucleotide sequences to be linked are designed so that they are mutually connected in frame. Human FRs are individually synthesized by specific primer sets. As a result, products are obtained in which a DNA that encodes a mouse CDR has been added to each FR. The nucleotide sequences encoding mouse CDRs of the products are designed to overlap one another. A complementary-strand synthesis reaction is then carried out by annealing the overlapping CDR portions of the above-mentioned products. As a result of this reaction, human FRs are linked through the mouse CDR sequence.

Finally, the full length of a V region gene in which three CDRs and four FRs have been linked is amplified by primers that anneal to its 5' and 3' ends and which have suitable restriction enzyme recognition sequences added. A vector for expressing the humanized antibody can then be prepared by inserting the DNA obtained in the manner described above and DNA encoding a human antibody C region into an expression vector so that they are fused in frame. The humanized antibody is then produced in a culture of cultured cells by introducing the expression vector into a host to establish recombinant cells, followed by culturing the recombinant cells and expressing the DNA encoding the humanized antibody (EP 239400 and WO 96/02576).

FRs of a human antibody can be preferentially selected so that the CDRs form a favorable antigen-binding site when linked through the CDRs, by qualitatively or quantitatively measuring and evaluating its binding activity to the antigen of the humanized antibody prepared in the manner described above. Amino acid residues of the FRs can also be substituted as necessary, so that the CDRs of the reshaped human antibody form a suitable antigen-binding site. For example, an amino acid sequence mutation can be introduced into FRs by applying PCR used to graft the mouse CDRs to the human FRs. Specifically, a mutation of a partial nucleotide sequence can be introduced into a primer that anneals to the FR. A mutated nucleotide sequence is introduced into the FR synthesized with such a primer. A mutant FR sequence with a desired property can be selected by measuring and evaluating the binding activity of the amino-acid-substituted mutant antibody to the antigen, using the method described above (Sato, K. et al., Cancer Res. (1993) 53, 851-856).

Methods for acquiring human antibodies are also known. For example, human lymphocytes are sensitized with the desired antigen or cells expressing the desired antigen in vitro. Next, the desired human antibody with binding activity for the antigen can be acquired by fusing the sensitized lymphocytes to human myeloma cells (JP-B H1-59878). U266 cells, for example, can be used as the human myeloma cells, to serve as the fusion partner.

A desired human antibody can also be acquired by immunizing with the desired antigen a transgenic animal with the repertoire of human antibody genes (WO 93/12227, WO 92/03918, WO 94/02602, WO 94/25585, WO 96/34096, and WO 96/33735). Moreover, technologies by which human antibodies can be acquired by panning, using a human antibody library, are also known. For example, the V region of a human antibody can be expressed on the surface of a phage in the form of a single-chain antibody (scFv) using the phage display method, thus allowing the selection of a phage that binds to an antigen. By analyzing the genes of the selected phage, it is possible to determine the DNA sequence encoding the V region of the human antibody that binds to the antigen. After determining the DNA sequence of the scFv that binds to the antigen, the V region sequence is fused in frame to the sequence of the C region of the desired human antibody, and is then inserted into a suitable expression vector to prepare an expression vector. The human antibody can be acquired by introducing the expression vector into the preferred expression cells, as described above, and expressing the gene encoding the human antibody. These methods are already known (WO 92/01047, WO 92/20791, WO 93/06213, WO 93/11236, WO 93/19172, WO 95/01438, and WO 95/15388).

The antibodies of the present invention include not only bivalent antibodies as represented by IgG, but also monovalent antibodies or polyvalent antibodies as represented by IgM, as long as they bind to the stalk domain of DDR1. The polyvalent antibodies of the present invention include those with the same antigen-binding sites, and those in which some or all of the antigen-binding sites are different.

Moreover, the antibody of the present invention may be a bispecific antibody provided it binds to the stalk domain of DDR1. A bispecific antibody refers to an antibody having variable regions that recognize different epitopes within the same antibody molecule, and the epitopes may be present in different molecules or may be present in the same molecule. Namely, in the present invention, a bispecific antibody can also have antigen-binding sites that recognize different epitopes of the stalk domain of DDR1. In addition, the bispecific antibody can also be that in which one of the recognition sites recognizes the stalk domain of DDR1 while the other recognition site recognizes an antigen other than DDR1. An antigen other than DDR1 may be, for example, an antigen that is specifically expressed on the cell surface of target cancer cells in the same manner as DDR1, or a cytotoxic substance or a surface antigen of immune cells such as T cells. In the present invention, "antibody" includes these antibodies as well.

Methods for producing a bispecific antibody are known. For example, a bispecific antibody can be produced by binding two types of antibodies having different recognized antigens. The bound antibodies may respectively be one-half of a molecule of antibody having an H chain and L chain, or may be one-fourth of antibody composed of H chain only. Alternatively, bispecific antibody-producing fused cells can be produced by fusing hybridomas that produce different monoclonal antibodies. Moreover, bispecific antibody can also be produced using genetic engineering techniques.

Moreover, the antibody of the present invention may be a conjugated antibody bound to various types of molecules such as polymeric substances for example polyethylene glycol (PEG) or hyaluronic acid, fluorescent substances, luminescent substances, or enzymes. This type of conjugated antibody can be obtained by chemically modifying an antibody. The antibody modification methods have already been established in this field.

The present invention provides an antibody obtained by lowering the molecular weight of the antibody of the present invention.

Minibodies (low molecular weight antibodies) include antibody fragments in which a portion of the whole antibody (such as whole IgG) is deleted. Partial deficiencies in antibody molecules are permitted as long as it binds to the stalk domain of DDR1. The antibody fragment of the present invention preferably comprises one or both of the heavy chain variable regions (VH) and light chain variable regions (VL). The amino acid sequences of VH or VL can comprise additions, deletions and/or substitutions. Moreover, a portion of one or both of VH and VL can be deleted as long as it binds to the stalk domain of DDR1. The antibody fragments may also be chimerized or humanized. Specific examples of antibody fragments include, for example, Fab, Fab', F(ab')2, and Fv. Specific examples of minibodies include Fab, Fab', F(ab')2, Fv, scFV (single-chain Fv), diabody, sc(Fv)2 (single-chain (Fv)2), etc. Polymers of these antibodies (such as dimers, trimers, tetramers, or polymers) are also included in the minibodies of the present invention.

Antibody fragments can be produced by digesting an antibody with an enzyme. Known examples of enzymes used to produce antibody fragments include papain, pepsin, plasmin, etc. Alternatively, DNAs encoding these antibody fragments can be constructed, introduced into an expression vector, and then expressed in suitable host cells (see, for example, Co M. S. et al., J. Immunol. (1994)152, 2968-

2976, Better M. & Horwitz A. H., Methods in Enzymology (1989)178, 476-496, Pluckthun A. & Skerra A., Methods in Enzymology (1989)178, 497-515, Lamoyi E., Methods in Enzymology (1986)121, 652-663, Rousseaux J. et al., Methods in Enzymology (1986)121, 663-669, Bird R. E. & Walker B. W., Trends Biotechnol. (1991)9, 132-137).

Digestive enzymes cleave a specific position of an antibody to yield an antibody fragment with a specific structure, as indicated below. Meanwhile, an arbitrary portion of an antibody can be deleted by applying genetic engineering techniques.

Papain digestion: Fab
Pepsin digestion: F(ab')2 or F(ab')
Plasmin digestion: Facb An scFv is obtained by linking the VH and VL of an antibody. In an scFv, the VH and VL are linked through a linker, preferably a peptide linker (Huston, J. S. et al., Proc. Natl Acad. Sci. U.S.A. (1988) 85, 5879-5883). The VH and VL in an scFv may be derived from any antibody described as an antibody herein. There is no particular limitation on the peptide linkers that link the V regions. For example, any arbitrary single-chain peptide comprising about three to 25 residues can be used as a linker.

The V regions can be linked by, for example, the PCR method described above. To link the V regions using the PCR method, a DNA encoding the entire or desired partial amino acid sequence of the DNA sequence encoding the H chain or the H chain V region of an antibody, and a DNA sequence encoding the L chain or the L chain V region of an antibody, are used as templates. DNA encoding the V regions of the H chain and that encoding L chain are both amplified by the PCR method using primers with sequences corresponding to the sequences at both ends of the DNA to be amplified. Next, DNA encoding the peptide linker portion is prepared. The DNA encoding the peptide linker can also be synthesized by PCR. Nucleotide sequences that can link the amplification products of each separately synthesized V region are added to the 5' side of the primers used at this time. Next, a PCR reaction is carried out using the "VH DNA", the "peptide linker DNA", and the "VL DNA" together with the primers for the assembly PCR. The primers for the assembly PCR consist of a combination of a primer that anneals to the 5' side of the "VH DNA" and a primer that anneals to the 3' side of the "VL DNA". Therefore, the primers for the assembly PCR consist of a primer set that can amplify the DNA encoding the entire sequence of the scFv to be synthesized. Conversely, nucleotide sequences that can link to each V region DNA are added to the "peptide linker DNA". As a result, these DNAs are linked together and the full length of scFv is finally produced as an amplification product of the primers used for the assembly PCR. Once a DNA encoding an scFv is prepared, an expression vector comprising the DNA and recombinant cells transformed with the expression vector can be acquired with ordinary methods. The scFv can also be acquired by expressing the DNA encoding the scFv in cultures of the resulting recombinant cells.

Diabodies refer to bivalent minibodies constructed by gene fusion (Holliger, P., et al., Proc. Natl. Acad. Sci. USA (1993) 90, 6444-6448; EP404097; WO93/11161). Diabodies are dimers composed of two polypeptide chains. Normally, in each of the polypeptide chains that compose dimers, VL and VH are bound by a linker in the same chain. Linkers of the polypeptide chains in diabodies are typically sufficiently short to prevent mutual binding between VL and VH within the same chain. More specifically, the amino acid residues that compose the linkers are preferably 2 to 12 residues, more preferably 3 to 10 residues, and particularly preferably about 5 residues. Consequently, the VL and VH encoded on the same polypeptide chain are unable to form scFv and dimerize so as to form two Fv between different polypeptide chains. As a result, diabodies have two antigen-binding sites.

sc(Fv)2 are minibodies in which two VH and two VL are bound with a linker and the like to make it single-stranded (Hudson, P. J. and Kortt, A. A., J. Immunol. Methods (1999) 231, 177-189). sc(Fv)2 can be produced by, for example, connecting two scFv with a linker. Alternatively, they can also be produced by connecting two VH and two VL via linkers, using the N-terminal side of a single-stranded polypeptide as a starting point, in the order of [VH]-[linker]-[VL]-[linker]-[VH]-[linker]-[VL]. The order of the two VH and two VL is not particularly limited to the order indicated above, and they may be arranged in any order. Examples of those arrangements are indicated below.

[VL]-[linker]-[VH]-[linker]-[VH]-[linker]-[VL]
[VH]-[linker]-[VL]-[linker]-[VL]-[linker]-[VH]
[VH]-[linker]-[VH]-[linker]-[VL]-[linker]-[VL]
[VL]-[linker]-[VL]-[linker]-[VH]-[linker]-[VH]
[VL]-[linker]-[VH]-[linker]-[VL]-[linker]-[VH]

The multiple linkers may be of the same type or of different types.

Any arbitrary peptide linker that can be introduced by genetic engineering, a synthetic compound linker (for example, those disclosed in Protein Engineering, (1996) 9, 299-305) or such, can be used as the linker to link antibody variable regions. Peptide linkers are preferred in the present invention. There is no particular limitation on the length of the peptide linkers, and the length can be suitably selected by those skilled in the art according to the purpose of use. Normally, the number of amino acid residues constituting a peptide linker ranges from one to 100 amino acids, preferably from three to 50 amino acids, more preferably from five to 30 amino acids, and particularly preferably from 12 to 18 amino acids (for example, 15 amino acids). The amino acid sequence constituting a peptide linker can be any arbitrary sequence as long as it does not inhibit the binding function of the scFv.

Alternatively, V regions can be linked using a synthetic chemical linker (chemical cross-linking agent). Cross-linking agents ordinarily used to cross-link peptide compounds and such can be used in the present invention. Examples of cross-linking agents that can be used include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES).

In addition, the present invention provides antibodies in which a cytotoxic agent is linked to the antibody of the present invention.

In the present invention, a cytotoxic agent refers to a substance that suppresses cell proliferation or induces cell death by inhibiting cell function. Examples of cytotoxic agents include chemotherapeutic agents, toxins, cytokines, enzymes, and radioisotopes. Enzymes include those that do not have cytotoxic activity, but can be used for the purpose of demonstrating cytotoxicity such as by activating a prodrug, for antibody-directed enzyme prodrug therapy (ADEPT). Cytotoxic agents can be linked to the antibody of the present invention through a covalent bond by using a chemical modification technique. Methods for chemically modifying antibodies have already been established in this field (as in, for example, U.S. Pat. No. 5,057,313 and U.S. Pat. No. 5,156,840). In addition, in the case the cytotoxic agent is a protein, it can be linked with the antibody of the present invention in the form of a fusion protein. Production of fusion protein can be carried out using a technique known to persons skilled in the art by linking a polynucleotide encoding the antibody of the present invention with a polynucleotide encoding a cytotoxic agent in frame, inserting into an expression vector, and expressing in a host. The antibody of the present invention and a cytotoxic agent may be linked directly or may be linked through a peptide linker as previously described.

In addition, the present invention provides a nucleic acid that encodes the antibody of the present invention.

In addition, the present invention provides a vector containing a nucleic acid encoding the antibody of the present invention. There are no particular limitations on the vector that can be used as long as it is able to stably retain an inserted nucleic acid, and various commercially available vectors can be used. Examples of vectors used for gene cloning include M13 vectors and pUC vectors. When using a vector for the purpose of producing the antibody of the present invention, an expression vector is particularly useful. There are no particular limitations on the expression vector as long as it is a vector that expresses polypeptide in vitro, in *Escherichia coli*, in cultured cells, or in a biological body. Examples of vectors for in vitro expression include pBEST vector (Promega Inc.), examples of vectors for expression in *Escherichia coli* include pGEX, pET, and pBluescript vectors (Stratagene Corp.), examples of vectors for expression in cultured cells include pME18S-FL3 vector (GenBank Accession No. AB009864), examples of vectors for expression in animal cells include pcDNA, and examples of vectors for expression in a biological body include pME18S vector (Mol. Cell. Biol. 8:466-472 (1988)). Insertion of the nucleic acid of the present invention into a vector can be carried out using, for example, the In-Fusion Advantage PCR Cloning Kit (Clontech Laboratories, Inc.).

Moreover, the present invention provides host cells that retain the aforementioned vector. There are no particular restrictions on the host cells, and various host cells can be suitably used corresponding to the particular purpose, examples of which include *Escherichia coli* (such as JM109, DH5α or BL21 (DE3)) and various animal cells (such as CHO or COS). For example, the host cells can be used as a production system for producing or expressing the antibody of the present invention. The production system includes in vitro and in vivo production systems.

A technique known to those skilled in the art can be used to insert a vector into host cells, examples of which include the calcium chloride method, calcium phosphate method, DEAE dextran method, methods using cationic liposome DOTAP (Boehringer Mannheim), electroporation, lipofection, methods using lipofectamine (Gibco-BRL Inc.), and micro-injection. In addition, the entire process from gene insertion to polypeptide expression can be carried out using the Free Style 293 Expression System (Invitrogen Corp.).

In addition, the present invention provides a hybridoma that produces antibody that binds to the stalk domain of DDR1.

More specifically, the present invention provides the hybridoma described in any of (a) to (c) below:
(a) a hybridoma deposited under Accession No. FERM BP-11399 (#115),
(b) a hybridoma deposited under Accession No. FERM BP-11398 (#27), and
(c) a hybridoma deposited under Accession No. FERM BP-11397 (#24).

The hybridomas of (a) to (c) above all produce an antibody that binds with the stalk domain of DDR1. In addition, the hybridomas of (a) to (c) above produce an antibody that suppresses cell proliferation, antibody that inhibits cell migration, antibody that inhibits phosphorylation of DDR1 in cells, antibody that is taken up into cells, antibody that decreases the expression level of DDR1 in cells, and/or antibody that decreases the expression level of TGF-β in cells.

In addition, the present invention provides an agent for treating or preventing cancer that contains the antibody of the present invention as an active ingredient.

In the present specification, "treating" refers to obtaining a pharmacological and/or physiological effect. The effect can be preventive in terms of completely or partially preventing proliferation and metastasis of cancer cells or symptoms attributable to cancer, and can be also therapeutic in terms of completely or partially treating cancer symptoms. In the present specification, "treating" includes all cancer therapy performed in mammals and particularly in humans. Moreover, it also includes prevention of the onset of cancer in subjects in whom cancer factors are present but have not yet been diagnosed with cancer, suppression of the progression and symptoms of cancer, and alleviation of the progression and symptoms of cancer.

The antibody of the present invention can be developed as an active ingredient of a cancer therapeutic or preventive agent since it has useful characteristics for suppressing proliferation, infiltration, and metastasis of cancer cells, such as activity that suppresses cell proliferation, activity that inhibits cell migration, activity that inhibits phosphorylation of DDR1 in cells, activity that is taken up into cells, activity that decreases the expression level of DDR1 in cells, and/or activity that decreases the expression level of TGF-β in cells.

In addition, the antibody of the present invention can be used in a method for treating cancer by administering to a subject that has been diagnosed with cancer. The diagnosis preferably uses as an indicator the expression level of DDR1 in a biological sample obtained from the subject, and an increase in the expression level compared to the normal control level of DDR1 suggests onset of cancer in the subject.

There are no particular limitations on the type of cancer targeted by the pharmaceutical agent of the present invention, and it is preferably a cancer that expresses DDR1 and more preferably a cancer that expresses DDR1 at a higher level than normal. Such a cancer can be selected by gene-level analyses such as RT-PCR or GeneChip analysis using a primer specific to DDR1 gene, or by protein-level analyses such as western blotting or immunohistostaining (IHC) using an antibody specific to DDR1 protein.

There are no particular limitations on the type of cancer targeted by the pharmaceutical agent of the present invention, and examples include lung cancer (such as small-cell lung cancer or non-small-cell lung cancer), breast cancer, glioma, ovarian cancer, gastric cancer, pancreatic cancer, esophageal cancer, endometrial cancer, bile duct cancer, colorectal cancer, liver cancer, leukemia, lymphoma, renal cancer, prostate cancer, melanoma, thyroid cancer, bladder cancer, and osteosarcoma. Preferable examples include lung cancer (non-small-cell lung cancer), breast cancer, glioma, ovarian cancer, gastric cancer, pancreatic cancer, esophageal cancer, endometrial cancer, and bile duct cancer.

In addition, the present invention relates to an agent for suppressing cell proliferation, an agent for inhibiting cell migration, an agent for inhibiting phosphorylation of DDR1 in cells, an agent for suppressing expression level of DDR1 in cells, or an agent for suppressing expression level of TGF-β in cells, which contains an antibody of the present invention as an active ingredient. The pharmaceutical agent of the present invention can further contain a cytotoxic agent.

In addition, the pharmaceutical agent containing an antibody of the present invention as an active ingredient can also be expressed as a method for treating or preventing cancer, a method for suppressing cell proliferation, a method for inhibiting cell migration, a method for inhibiting phosphorylation in cells, a method for suppressing expression of DDR1 in cells, or a method for suppressing expression of TGF-β in cells, by using the antibody of the present invention. Namely, the present invention relates to a method for treating or preventing cancer, a method for suppressing cell proliferation, a method for inhibiting cell migration, a method for inhibiting phosphorylation in cells, a method for suppressing expression of DDR1 in cells, or a method for suppressing expression of TGF-β in cells, comprising administering an effective amount of the antibody of the present invention to a target animal. Here, the target animal is preferably a mammal, and most preferably a human.

In addition, a cytotoxic agent can further be administered in these methods of the present invention.

In addition, the use of the antibody of the present invention to produce the pharmaceutical agent of the present invention can also be expressed as the antibody of the present invention used in the treatment or prevention of cancer, suppression of cell proliferation, inhibition of cell migration, inhibition of phosphorylation in cells, suppression of expression of DDR1 in cells, or suppression of expression of TGF-β in cells.

The agent for treating or preventing cancer of the present invention can also be administered by formulating in accordance with known pharmaceutical methods in addition to administering directly to a subject (such as a patient) (see, for example, Remington's Pharmaceutical Science, latest edition, Mark Publishing Company, Easton, USA). The pharmaceutical agent of the present invention can be formulated by combining the antibody of the present invention with other pharmaceutical ingredients as necessary. For example, pharmaceutically acceptable carriers or additives may be contained together.

In addition, the pharmaceutical agent of the present invention can be used parenterally in the form of an injection preparation of a sterile solution or suspension with water or other pharmaceutically acceptable liquid. Drug forms for oral administration or parenteral administration, and production methods thereof, are well known to persons skilled in the art, and can be produced in accordance with ordinary methods by mixing a pharmaceutically acceptable carrier and the like with the pharmaceutical agent of the present invention. In the present invention, examples of carriers include, but are not limited to, sterilized water, physiological saline, vegetable oils, emulsifiers, surfactants, excipients, vehicles, colorants, fragrances, preservatives, antiseptics, stabilizers, buffers, suspension agents, isotonic agents, binders, disintegration agents, lubricants, fluidity promoters, flavoring agents, and correctives, and other routinely used carriers can also be suitably used. Specific examples include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium-chain fatty acid triglycerides, polyoxyethylene hydrogenated castor oil 60, saccharose, carboxymethyl cellulose, cornstarch, and inorganic salts. The pharmaceutical agent of the present invention may be formulated by suitably combining and mixing these ingredients in the form of unit doses required for carrying out commonly recognized drug development. The amount of active ingredient in these preparations is set so as to obtain a suitable volume within an instructed range.

The pharmaceutical agent of the present invention can be administered orally or parenterally, and it is preferably administered parenterally, and specific examples include injection administration, transnasal administration, transpulmonary administration, and transcutaneous administration. Examples of injection administration include intravenous administration, intramuscular administration, intraperitoneal administration, and subcutaneous administration. The dosage can be suitably selected, for example, within the range of 0.0001 mg to 1,000 mg per kilogram of body weight of the patient, or within the range of 0.001 mg to 10,000 mg per patient, although not limited thereto. The administered subject is a mammal and preferably a human.

In addition, the present invention provides a kit containing the antibody or pharmaceutical agent of the present invention, and a kit for use in the various methods of the present invention. The kit of the present invention contains the antibody or pharmaceutical agent of the present invention. The kit of the present invention can further contain instructions and the like describing the method of use in the form of a package.

All prior art reference cited herein are incorporated by reference in their entirety.

EXAMPLES

Although the present invention will be explained in more detail by the following Examples, the present invention is not limited by these Examples.

Example 1

1-1 Preparation of Antigen

Hamster ovary cells (CHO (dhfr⁻) cells) were transfected with the expression vector for a fusion protein (hDDR1-ECD-mIgG2aFc), in which the extracellular domain of human DDR1 and an Fc domain of mouse IgG2a were fused, and CHO cell lines that produce hDDR1-ECD-mIgG2aFc protein were cloned with G418 selection. The nucleotide sequence and amino acid sequence of hDDR1-ECD-mIgG2aFc are indicated as SEQ ID NOs: 5 and 6, respectively. The culture supernatant of the hDDR1-ECD-mIgG2aFc protein-producing CHO cell lines collected using serum-free medium (CHO-S-SFM II; Gibco) was added to a Protein G Column (HiTrap Protein G HP, GE Healthcare) equilibrated with a binding buffer (20 mM phosphate buffer, pH 7.0). After the unbound proteins were washed with the binding buffer, fractions of hDDR1-ECD-mIgG2aFc protein were collected with an elution buffer (100 mM glycine-HCl, pH 2.7) into tubes containing neutralizing buffer (1 M Tris-HCl, pH 9.0). Then the buffer of the purified protein was replaced with phosphate-buffered physiological saline (pH 7.35-7.65; Takara Bio) and the purified protein was concentrated using an ultrafiltration kit for a molecular weight fraction of 10 kDa (Centricon™, Millipore). The concentration of the purified protein was calculated from the absorbance at 280 nm using a molar absorption coefficient calculated according to the calculation formula of the document (Pace C. N. et al., Protein Sci. (1995) 4:2411-2423).

1-2 Preparation of Anti-DDR1-Antibody-Producing Hybridoma

Two BALB/c mice (male, six weeks old at the start of immunization, Charles River Laboratories Japan) and five MRL/lpr mice (male, six weeks old at the start of immunization, Charles River Laboratories Japan) were immunized as described below with the antigen prepared in the previous section (hDDR1-ECD-mIgG2aFc protein). Antigen emulsified with Freund's complete adjuvant (H37 Ra, Difco Laboratories) was administered subcutaneously at 100 µg/head as the initial immunization. Two weeks later, antigen emulsified with Freund's incomplete adjuvant (FIA; Difco Laboratories) was administered subcutaneously at 50 µg/head. The animals were subsequently immunized three times more at one week intervals. Increases in the serum antibody titer in response to the antigen were confirmed by Enzyme Linked Immunosorbent Assay (ELISA) as indicated in the sections 1-4, followed by a final immunization of intravenous administration of antigen diluted with phosphate-buffered physiological saline (phosphate-buffered saline without calcium ions or magnesium ions, PBS(-); Nissui Pharmaceutical) at 10 µg/head. Three days after the final immunization, mouse spleen cells and mouse myeloma cells P3X63Ag8U.1 (referred to as P3U1, ATCC CRL-1597) were fused according to ordinary methods using PEG 1500 (Roche Diagnostics). The fused cells were cultured in RPMI1640 medium (Invitrogen) containing 10% FBS (Invitrogen) (hereafter referred to as 10% FBS/RPMI1640). On the day after fusion, the fused cells were suspended in semifluid medium (StemCells) followed by the selective culture and colonization of the hybridomas. Hybridoma colonies were picked from the medium on the ninth or tenth day after fusion and seeded into a 96-well plate containing HAT selective medium (10% FBS/DMEM, 2 vol % HAT 50× concentrate [Dainippon Pharmaceutical] and 5 vol % BM-Condimed H1 [Roche Diagnostics]) at one colony per well. After culturing for 3 to 4 days, the supernatant was collected from each well and hybridomas having binding activity to the extracellular domain of human DDR1 were selected by measuring their binding activity to the aforementioned antigen and to a control protein fused with the Fc domain of mouse IgG2a by ELISA as indicated in Section 1-4.

1-3 Purification of Antibody from Hybridoma Culture Supernatant

The resulting hybridomas described above were cultured in HAT selective medium using low-IgG FBS (Invitrogen) for the FBS. Protein G beads (Pharmacia), in which the solvent was replaced with wash buffer (20 mM sodium acetate buffer, pH 5.0), were added to 20 mL to 50 mL of the culture supernatant at 50 µL per 10 mL of culture supernatant, followed by mixing by inversion overnight at 4° C. After the Protein G beads had been collected and washed with wash buffer, the antibody was eluted with elution buffer (50 mM sodium acetate buffer, pH 3.3), and was immediately neutralized with neutralizing buffer (Tris-HCl buffer, pH 7.8). The buffer was replaced with phosphate-buffered physiological saline (pH 7.35-7.65; Nissui Pharmaceutical Co., Ltd.) and the purified antibody was concentrated using an ultrafiltration kit for a molecular weight fraction of 10 kDa (Amicon™, Millipore), followed by sterilization with a 0.22 µm sterilization filter (Millipore GV, Millipore).

1-4 Binding Activity to Human DDR1

Binding activity of anti-DDR1 antibody was measured by ELISA indicated below. Antigen (hDDR1-ECD-mIgG2aFc protein) diluted to 1 µg/mL with coating buffer (100 mM sodium bicarbonate, pH 9.6, 0.02% sodium azide) or control protein fused with the Fc domain of mouse IgG2a was dispensed into a 96-well plate (Nunc-Immuno™ 96 MicroWell™ MaxiSorp™ plate; Nalge Nunc International) at 80 µL/well, followed by incubating at least overnight at 4° C. After washing three times with phosphate-buffered physiological saline containing 0.05 vol % Tween 20 (tPBSH), the plate was blocked at least overnight at 4° C. with diluent buffer (1/5 dilution of BlockingOne; Nacalai Tesque Inc.). After removing the buffer, mouse antiserum or hybridoma culture supernatant diluted with diluent buffer was added to the plate at 80 µg/well, followed by incubating for one hour at room temperature. After the plate had been washed three times with tPBS(-), HRP-labeled anti-mouse IgG antibody (Stressgen), diluted 1/5000 with diluent buffer, was added at 80 µL/well, followed by incubating for one hour at room temperature. After the plate had been washed five times with tPBS(-), a chromogenic substrate Peroxidase Substrate (Kirkegaad & Perry Laboratories) was added at 80 µL/well, followed by incubating for 20 minutes at room temperature. After the addition of Peroxidase Stop Solution (Kirkegaad & Perry Laboratories) at 80 µL/well, the absorbance at 405 nm was measured with a Microplate Reader Model 3550 (Bio-Rad Laboratories). The binding activity of each antibody is shown in FIG. 1. Although each antibody strongly bound to DDR1, they hardly bound at all to DDR2, which indicated that the antibodies are antibodies that specifically bind to DDR1.

Example 2

Binding Activity to Human ΔDS-DDR1, ΔStalk-DDR1, and FL-DDR1

A test was conducted to determine the region of DDR1 where anti-DDR1 monoclonal antibody binds. An immunoprecipitation experiment was conducted using anti-DDR1 monoclonal antibody by transiently expressing mutants respectively missing the DS domain and stalk domain of DDR1 in Chinese hamster ovary cell line CHO.

2-1 Production of Expression Vectors

In order to express ΔDS-DDR1 protein, in which the 32nd to 185th amino acids of human DDR1 are lacking, the corresponding cDNA domain was removed by PCR and a cDNA sequence was inserted into an expression vector pCXND3 so as to fuse the 31st and 186th amino acids in-frame. At this time, a FLAG tag was fused to the carboxyl terminal of human DDR1. This expression vector is hereinafter referred to as pCXND3-ΔDS-DDR1-FLAG. pCXND3 is an expression vector having a cytomegalovirus enhancer and fowl β-actin-rabbit globin promoter. The amino acid sequence of ΔDS-DDR1 is shown in SEQ ID NO: 8 and the nucleotide sequence is shown in SEQ ID NO: 7.

In order to express ΔStalk-DDR1 protein, in which the 199th to 412th amino acids of human DDR1 are lacking, the corresponding cDNA domain was removed by PCR and a cDNA sequence was inserted into an expression vector pCXND3 so as to fuse the 198th and 413th amino acids in-frame. At this time, a FLAG tag was fused to the carboxyl terminal of human DDR1. This expression vector is hereinafter referred to as pCXND3-ΔStalk-DDR1-FLAG. The amino acid sequence of ΔStalk-DDR1 is shown in SEQ ID NO: 10 and the nucleotide sequence is shown in SEQ ID NO: 9.

In order to express the human full-length DDR1 (FL-DDR1) protein, the corresponding cDNA sequence was inserted into expression vector pCXND3. At this time, a FLAG tag was fused to the carboxyl terminal of human DDR1. This expression vector is hereinafter referred to as pCXND3-DDR1-FLAG. The amino acid sequence of FL-DDR1 is shown in SEQ ID NO: 12 and the nucleotide sequence is shown in SEQ ID NO: 11.

Schematic diagrams of ΔDS-DDR1, ΔStalk-DDR1, and FL-DDR1 are shown in FIG. 2(a).

2-2 Expression of Recombinant Protein $2\times10^6$ CHO cells were seeded into a 10 cm dish and cultured overnight. On the following day, 24 μg each of 3 types of expression vectors, pCXND3-DDR1-FLAG, pCXND3-ΔDS-DDR1-FLAG, and pCXND3-ΔStalk-DDR1-FLAG were transiently transfected into CHO cells using Lipofectamine 2000 (Invitrogen).

2-3 Evaluation of Binding Activity of Anti-DDR1 Antibody to ΔDS-DDR1, ΔStalk-DDR1 and FL-DDR1 by Immunoprecipitation Following transfection, the CHO cells were washed with PBS after having cultured for 3 days at 37° C. and 5% $CO_2$, followed by lysing with cell lysis buffer (100 mM Tris-HCl (pH 7.5), 150 mM NaCl, 5 mM EDTA, 10% glycerol, 1% Triton X-100, PhosSTOP (Roche) and Complete Mini EDTA-Free (Roche)). The cell-solution mixture was disrupted with an ultrasonic disrupter (Tomy Seiko Co., Ltd.) followed by centrifuging for 15 minutes at 4° C. After adding 1.2 μg of anti-DDR1 antibody to the supernatant and incubating overnight on ice, 30 μL of Protein G Sepharose (GE Healthcare) were added followed by shake culturing for 1 hour at 4° C. The immunoprecipitate was washed three times with cell lysis buffer by centrifuging for 5 minutes at 4° C. followed by suspending in SDS sample buffer and heating for 10 minutes at 95° C. After electrophoresing the immunoprecipitate using NuPAGE (Invitrogen), the gel was transferred to a nitrocellulose filter using iBlot™ (Invitrogen) and iBlot™ gel transfer stacks, nitrocellulose, regular (Invitrogen). After incubating the filter with Odyssey Blocking Buffer (Li-COR), rabbit anti-FLAG antibody (diluted 1:1000 with TBS-T/3% BSA, Sigma) was added followed by incubating overnight at 4° C. After washing the filter three times for 10 minutes each with TBS-T, Alexa 680-labeled anti-rabbit IgG (Invitrogen) diluted 1:24000 with TBS-T/3% BSA was added followed by incubating for 2 hours at room temperature. After washing three times for 10 minutes each with TBS-T and further washing once for 5 minutes with TBS, the filter was scanned using the Odyssey Infrared Imaging System (Li-COR).

Although anti-DDR1 antibodies #115, #27 and #24 all caused immunoprecipitation of ΔDS-DDR1, ΔStalk-DDR1 did not immunoprecipitate. Based on the above, the aforementioned anti-DDR1 antibodies were all clearly determined to recognize the Stalk domain of DDR1. Conversely, although 20M102 caused immunoprecipitation of ΔStalk-DDR1, since it did not cause immunoprecipitation of ΔDS-DDR1, it was determined to clearly recognize the DS domain of DDR1 (FIG. 2(b)).

Example 3

Measurement of Antitumor Effects of Anti-DDR1 Antibody in Mouse Model Grafted with Human Lung Cancer 3-1 Preparation of Mouse Model Grafted with Human Lung Cancer Human lung carcinoma cell line NCI-H1993 acquired from ATCC was suspended in HBSS at $5\times10^7$ cells/mL. 200 μL of the aforementioned cell suspension ($1\times10^7$ cells/mouse) were subcutaneously grafted into CAnN.Cg-Foxn1<nu>/Crlcrlj nu/nu (BALB-nu/nu) mice purchased from Charles River Laboratories Japan Inc. The mice were grouped and used in the experiment when the tumor volume reached an average of about 150 $mm^3$ (n=4).

3-2 Antibody Preparation and Administration

Anti-DDR1 antibody was prepared to 2 mg/mL with PBS and administered into the peritoneal cavity of the mice grafted with human lung cancer twice a week for two weeks at 40 mg/kg. PBS was administered in the same manner for use as a negative control.

3-3 Evaluation of Antitumor Effects

Antitumor effects in a mouse model grafted with human lung cancer were calculated using the following equation based on the amount of tumor growth from the start of administration of anti-DDR1 antibody (25th day after grafting tumor) to four days after final administration of anti-DDR1 antibody (39th day after grafting tumor) (Δ$mm^3$, average of n=4). Tumor growth suppressive effect (%)=(1−amount of tumor growth of antibody-treated group/amount of tumor growth of control group)×100

3-4 Statistical Processing

Tumor volume was expressed as the mean±standard deviation. Statistical analysis consisted of a comparison between the control group and the treated group by the LSD method using the SAS Preclinical Package Ver. 5.0. In addition, reliability of 95% (*: $p<0.05$) was determined to constitute significance.

3-5 Results

Figure 3:
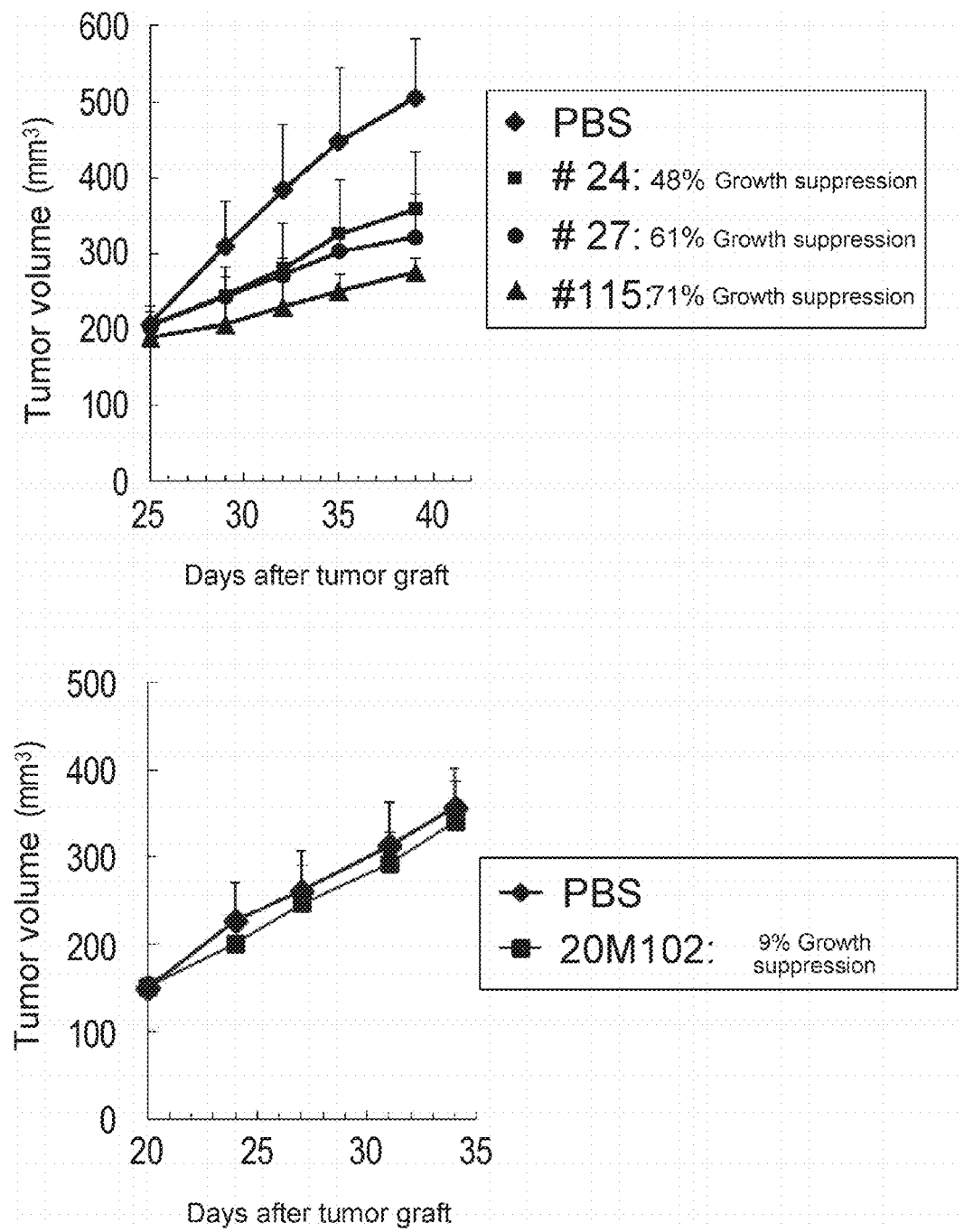
FIG. 3 is a graph indicating antitumor activity of anti-DDR1 antibody in a mouse model grafted with human lung cancer. PBS (negative control) or anti-DDR1 antibody was administered intraperitoneally to mice grafted with human lung carcinoma cell line NCI-H1993, followed by measuring changes in tumor volume over time. Tumor growth suppressive effects were observed with antibodies #115, #24 and #27. In particular, antibody #115 demonstrated the most potent tumor growth suppressive effect. On the other hand, 20M102 did not demonstrate tumor growth suppressive effects.

Anti-DDR1 antibody #115 demonstrated the most potent tumor growth suppressive effect of 71%. Anti-DDR1 antibodies #24 and #27 were observed to demonstrate potent tumor growth suppressive effects of 48% and 61%, respectively. On the other hand, 20M102 did not demonstrate tumor growth suppressive effects (FIG. 3).

Example 4

Assay of Ligand-Dependent Cell Migration by Anti-DDR1 Antibody 4-1 Cell Migration Assay Using RT-CIM System The inhibitory activity of anti-DDR1 antibody on collagen-dependent cell migration in human lung carcinoma cell line NCI-H1993 was evaluated using the xCELLigence System (Roche Applied Science). The experimental procedure was carried out in accordance with protocol provided with the system. The aforementioned cells were collected in Cell Dissociation Buffer (Gibco) followed by centrifuging for 5 minutes at 12000 rpm and 4° C. After further washing with PBS (Nacalai Tesque Inc.), the cells were suspended in serum-free medium, and for antibody-treated cells, antibody solution was added so as to be 10 µg/mL of anti-DDR1 antibody followed by culturing for 30 minutes. Culture solution for the lower chamber was prepared with serum-free medium to be 10 µg/mL of anti-DDR1 antibody and 100 µg/mL of collagen type 4 (Cellmatrix). Each membrane of the upper chamber of a CIM-plate composed of an upper chamber and lower chamber was coated at 40 µL/well with fibronectin solution (Sigma) adjusted to 5 µg/mL with PBS. Antibody-collagen solution was added to the lower chamber at 160 µL/well and the upper chamber was combined. Next, after adding the antibody-treated cells to each well of the upper chamber at 5×10⁴ cells/well, the number of cells that migrated to the back side of the membrane of the upper chamber was measured on the basis of electrical resistance values with the xCELLigence System placed in an incubator at 37° C. (migration time: 10 hours). A group to which only ligand (collagen) was added without adding anti-DDR1 antibody was used as a negative control.

The number of cells that migrated in the absence of addition of collagen was used as a background value, and the values obtained by subtracting the background value from the measured value of each group were defined as the amount of cell migration of each group. Cell migration inhibitory activity of anti-DDR1 antibody was calculated according to the equation indicated below.

Migration inhibitory activity (%)=(1−number of migrated cells of antibody-treated group/number of migrated cells of control group)×100

Figure 4:
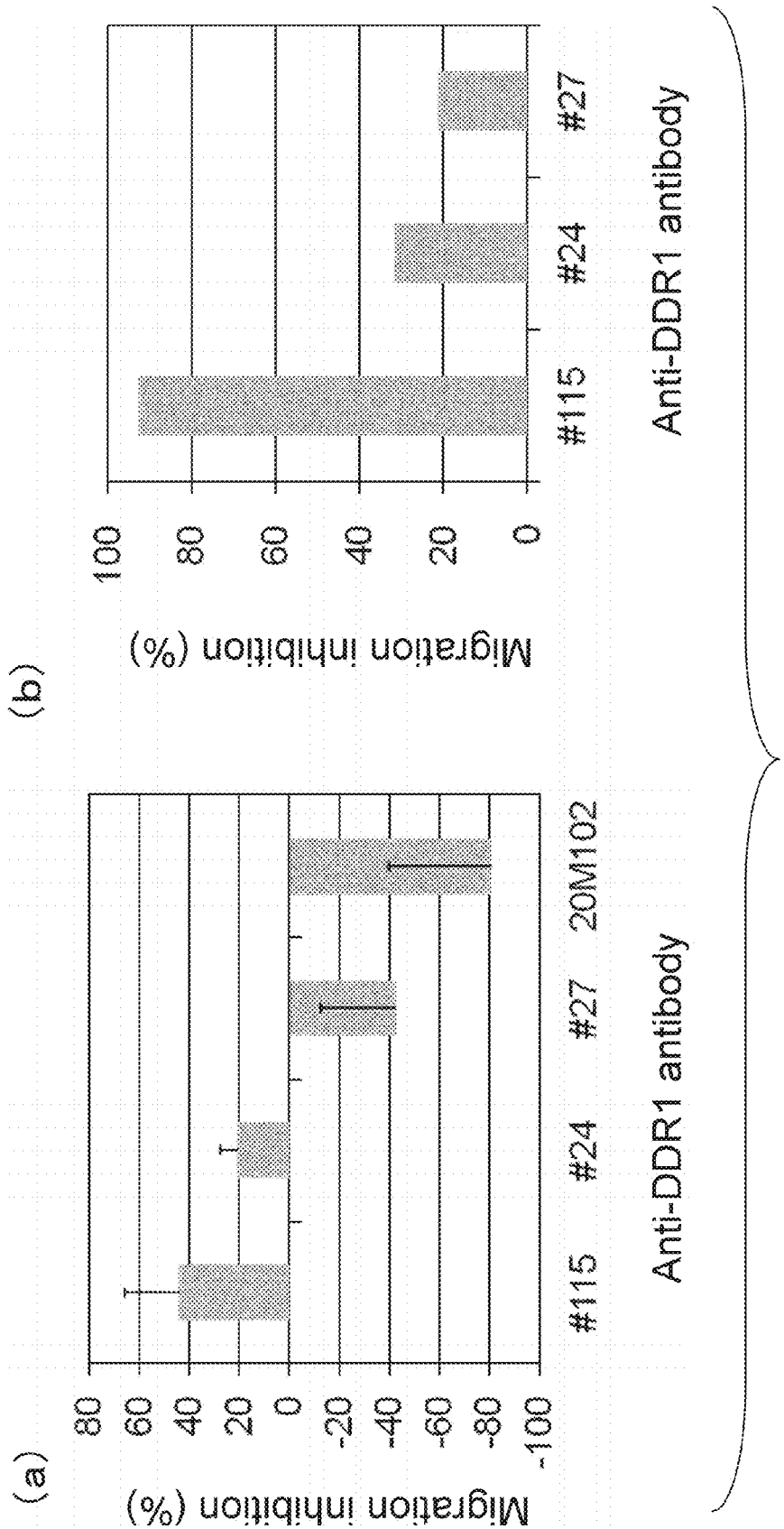
FIG. 4 is a graph indicating the ligand-dependent cell migration-inhibiting activity of anti-DDR1 antibodies.

As a result, inhibition of collagen-dependent cell migration was observed for antibodies #115 and #24 (FIG. 4(a)).

4-2 Assay of Cell Migration Using Cultrex

The inhibitory activity of anti-DDR1 antibody on collagen-dependent cell migration in human lung carcinoma cell line NCI-H1993 was evaluated using the Cultrex Cell Migration Assay Kit (Trevingen). The experimental procedure was carried out in accordance with protocol provided with the kit. The aforementioned cells were collected in Cell Dissociation Buffer (Gibco) followed by centrifuging for 5 minutes at 12000 rpm and 4° C. After further washing with PBS (Nacalai Tesque Inc.), the cells were suspended in serum-free medium. For antibody-treated cells, an antibody solution was added thereto so as to be 10 µg/mL of anti-DDR1 antibody followed by culturing for 30 minutes. A culture solution for the lower chamber was prepared with serum-free medium to be 10 µg/mL of anti-DDR1 antibody and 100 µg/mL of collagen type 4 (Cellmatrix). Each membrane on the bottom of the upper chamber of the Cultrex kit composed of an upper chamber and lower chamber was coated at 40 µL/well with fibronectin solution (Sigma) adjusted to 5 µg/mL with PBS. Antibody-collagen solution was added to the lower chamber at 150 µL/well and the upper chamber was combined. Next, the antibody-treated cells were allowed to migrate for 19 hours at 37° C. after adding the cells to each well of the upper chamber at 1×10⁴ cells/well. Subsequently, after washing the membrane of the upper chamber with wash buffer provided with it, the membrane was immersed in dissociation buffer containing Calcein-AM, and the number of cells that migrated by penetrating through the membrane was measured at fluorescence wavelengths of 485 nm and 520 nm. A group to which only ligand (collagen) was added without adding anti-DDR1 antibody was used as a negative control.

The number of cells that migrated in the absence of addition of collagen was used as a background value, and the values obtained by subtracting the background value from the measured value of each group were defined as the amount of cell migration of each group. Cell migration inhibitory activity of anti-DDR1 antibody was calculated according to the equation indicated below.

Migration inhibitory activity (%)=(1−number of migrated cells of antibody-treated group/number of migrated cells of control group)×100

As a result, inhibition of collagen-dependent cell migration was observed for antibodies #115, #24, and #27 (FIG. 4(b)).

Example 5

Assay of Inhibition of Ligand-Dependent Phosphorylation by Anti-DDR1 Antibody 5-1 Electrophoresis Human breast cancer cell line T47D cells were washed with PBS(−) followed by lysing with cell lysis buffer (Lysis buffer (CST)), 1/100×Phosphatase Inhibitor Cocktails 2, 3 (Sigma), 1/100×Aprotinin (Sigma) and 1/100×PMSF (Sigma)) and freezing at −80° C. Subsequently, the cell solution was disrupted with an ultrasonic disrupter (Tomy Seiko Co., Ltd.) followed by centrifuging for 10 minutes at 4° C. (20,000×g). The resultant was then suspended in NuPAGE-LDS sample buffer (Invitrogen) and heated for 10 minutes at 70° C. The prepared protein solution was electrophoresed for 1 hour at 20 mA using SuperSep™ Ace 7.5% (Wako Pure Chemical Industries Ltd.).

5-2 Western Blotting and Tyrosine Phosphorylation Assay

The protein electrophoresed with SuperSep™ Ace 7.5% was electrophoretically transferred to a 0.45 µm polyvinylidene difluoride filter (Immobilon-FL, Millipore) with a transfer buffer (Bio-Rad) over the course of 3 hours at 70 V. Blocking was carried out by washing the filter with TBS (50 mM Tris-HCl (pH 7.6), 150 mM NaCl) and incubating overnight in Blocking One-P/Blocking One (Nacalai Tesque Inc.). The filter was then washed four times for 5 minutes each with TBST (TBS containing 0.05 vol % Tween 20), and incubated for 2 hours at room temperature with anti-DDR1 antibody (Santa Cruz, diluted 1:3000 with Can Get Signal Solution 1 (Toyobo Co., Ltd.)) and anti-pY796DDR1 antibody (rabbit polyclonal antibody to LYAGD<u>Y</u>YRVQG peptide (where <u>Y</u> represents phosphorylated tyrosine) (SEQ ID NO: 15), produced by MBL) (diluted 1:3000 with Can Get Signal Solution 1 (Toyobo Co., Ltd.)). The filter was then washed 4 times for 5 minutes each with TBST, and incubated for 1 hour with HRP-labeled anti-rabbit secondary antibody (CST) diluted 1:10,000 with Can Get Signal Solution 2 (Toyobo Co., Ltd.). After washing three times for 5 minutes each with TBST and further washing once for 5 minutes with TBS, the filter was scanned using LAS4000 (Fuji Film Corp.).

5-3 Assay of Inhibition of Ligand-Dependent Phosphorylation by Antibody

Figure 5:
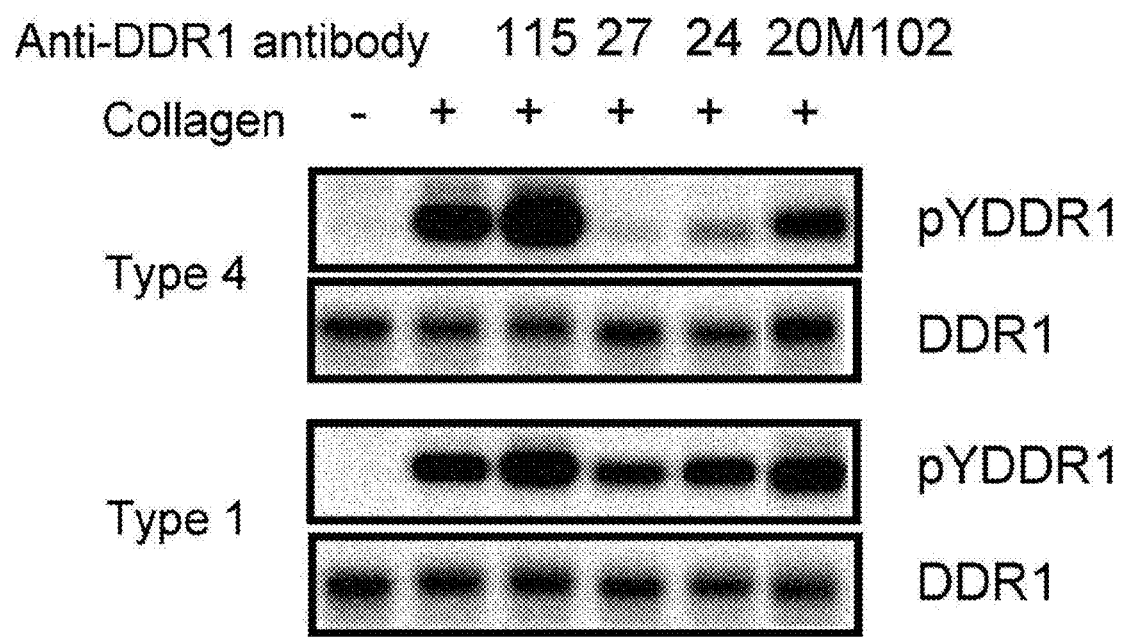
FIG. 5 shows photographs representing the inhibitory activity of anti-DDR1 antibody on ligand-dependent DDR1 phosphorylation. Ligand-dependent DDR1 phosphorylation in human breast cancer cell line T47D was detected by western blotting using polyclonal antibody that specifically recognizes DDR1 in which the 796th tyrosine has been phosphorylated (pYDDR1). Collagen type 1 or collagen type 4 was used for the ligand. Inhibition of ligand-dependent DDR1 phosphorylation was observed for antibodies #27 and #24.

The ability of anti-DDR1 antibody to inhibit ligand-dependent phosphorylation within cancer cells was tested. Human breast cancer cell line T47D cells were seeded into six-well plates at a density of $1\times10^6$ cells/well and 24 hours later, the medium was replaced with serum-free medium, and the cells were cultured for 3 hours. Next, after adding anti-DDR1 antibody to be 10 µg/mL and incubating for 30 minutes at 37° C., collagen type I (Cellmatrix) and collagen type 4 (Cellmatrix) were added to be 100 µg/mL followed by incubating for 2 hours at 37° C. Next, the cells were washed with PBS(−) and protein was extracted from the cells with cell lysis buffer. The resultants were separated on SuperSep™ Ace 7.5% (Wako Pure Chemical Industries Ltd.), and immunoblotted by the western blotting and tyrosine phosphorylation assay of Section 5-2. As a result, the blot of the phosphotyrosine antibody was weakened by antibodies #27 and #24 (FIG. 5). This strongly supports the finding that these anti-DDR1 antibodies can have a function that inhibits the phosphorylation induction action of collagen, which is the DDR1 ligand. Details of the pathway by which DDR1 signals are transmitted by collagen will be able to be further investigated in the future using a phenomenon by which autophosphorylation of DDR1 is controlled with the anti-DDR1 antibodies.

Example 6

Assay of Internalization of DDR1 on Cell Surface by Anti-DDR1 Antibody

Human breast cancer cell line T47D cells were seeded at $5\times10^3$ cells/well and cultured for 24 hours at 37° C. Anti-DDR1 antibody and MabZAP (saporin-labeled anti-mouse IgG antibody, Advanced Targeting Systems) were respectively added to reach a final concentration of 5 µg/mL followed by culturing for 3 days at 37° C. Subsequently, 10 µg/mL of cell proliferation measurement reagent WST-8 (Cell Counting Kit-8, DOJINDO LABORATORIES) were added followed by culturing for 1 hour at 37° C. and measuring absorbance at 460 nm with a microplate reader.

Figure 6:
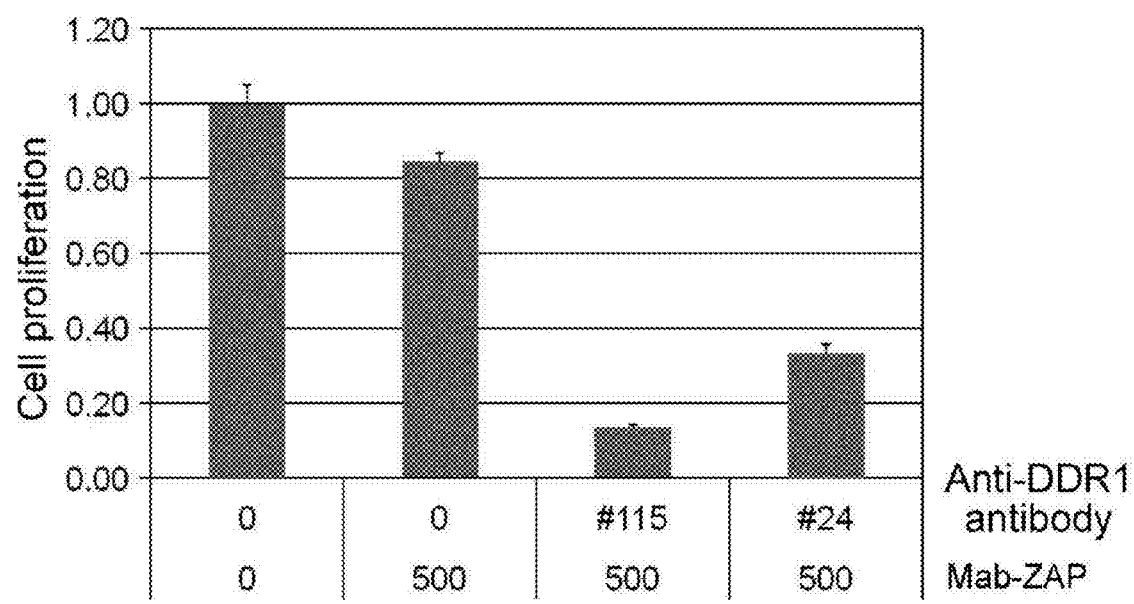
FIG. 6 is a graph indicating internalization of anti-DDR1 antibody into cells. Internalization of an anti-DDR1 antibody into cells was evaluated by adding the anti-DDR1 antibody and MabZAP (saporin-labeled anti-mouse IgG antibody) to human breast cancer cell line T47D, and investigating whether or not cell proliferation is inhibited. The ratio of cell proliferation when anti-DDR1 antibody and MabZAP were added is indicated on the vertical axis, taking as 1 cell proliferation in the absence of both anti-DDR1 antibody and MabZAP. Internalization into cells was observed for antibodies #115 and #24.

In this assay system, since cell proliferation is inhibited by the toxicity of saporin when anti-DDR1 antibody and the MabZAP bound thereto are taken up into cells, internalization of anti-DDR1 antibody into cells can be evaluated by measuring cell proliferation. Internalization of anti-DDR1 antibody into cells was measured by calculating the ratio of cell proliferation in the case of the addition of anti-DDR1 antibody and MabZAP based on a value of 1 for cell proliferation in case of not adding anti-DDR1 antibody and MabZAP. As a result, inhibition of cell proliferation was detected for antibodies #115 and #24, and antibodies #115 and #24 were confirmed to be taken up into cells by binding to DDR1 on the cell surface (FIG. 6).

Example 7

Decrease in Expression Level of DDR1 Caused by Anti-DDR1 Antibody

The ability of anti-DDR1 antibody to decrease the expression level of DDR1 in cells was tested. Human breast cancer cell line T47D cells were seeded into 6-well plates at a density of $5\times10^5$ cells/well and cultured for 24 hours. Anti-DDR1 antibody was added to be 10 µg/mL followed by incubating for 24 hours at 37° C. Next, the cells were washed with PBS(−) and protein was extracted from the cells with the cell lysis buffer of Section 5-1. The resultants were separated on SuperSep™ Ace 7.5% (Wako Pure Chemical Industries Ltd.), and immunoblotted in accordance with the western blotting of Section 5-2.

Figure 7:
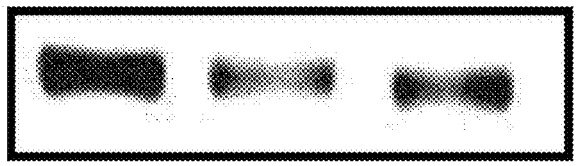
FIG. 7 shows photographs representing decreases in expression levels of DDR1 caused by anti-DDR1 antibodies. Expression levels of DDR1 in cells were detected by western blotting by adding PBS (negative control) or an anti-DDR1 antibody to human breast cancer cell line T47D. Actin was used as an internal control. Decreases in expression levels of DDR1 were observed for antibodies #115 and #24.
Figure 7:
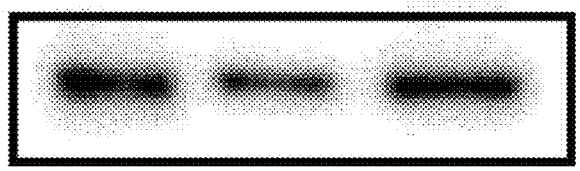

Anti-DDR1 antibody (SantaCruz, diluted 1:3000 with Can Get Signal 1) and anti-actin antibody (SantaCruz, diluted 1:3000 with Can Get Signal 1) were used for the detection antibodies, and incubation with each antibody was carried out for 2 hours at room temperature. The filter was washed four times for 5 minutes each with TBST followed by incubating for 1 hour with HRP-labeled anti-rabbit secondary antibody (CST) and HRP-labeled anti-sheep secondary antibody (Invitrogen) diluted 1:10000 with Can Get Signal 2. After washing three times for 5 minutes each with TBST and further washing once for 5 minutes with TBS, the filter was scanned using LAS4000 (Fuji Film Corp.). As a result, antibodies #115 and #24 were observed to decrease the expression level of DDR1 (FIG. 7).

Example 8

Figure 8:
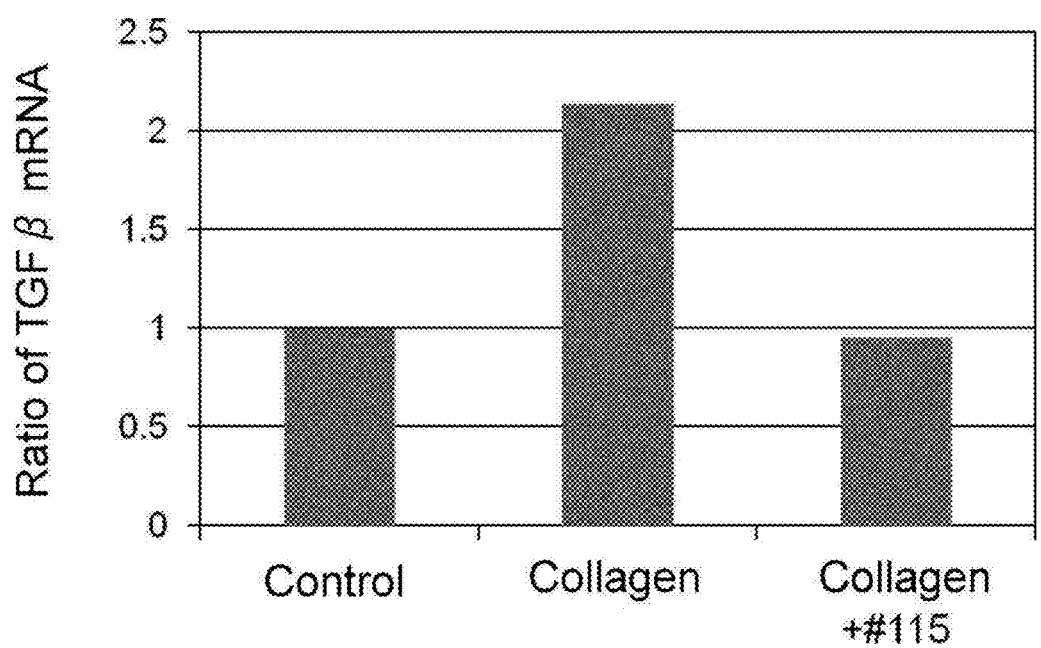
FIG. 8 is a graph indicating inhibitory activity of anti-DDR1 antibodies on ligand-dependent expression of TGF-β. Ligand-dependent expression levels of TGF-β mRNA in a co-culturing system containing human lung carcinoma cell line NCI-H1993 and mouse fibroblasts MRC5 were measured by quantitative RT-PCR (qRT-PCR). Collagen type 1 was used for the ligand. The ratio of the amount of TGF-β mRNA is indicated on the vertical axis, taking as 1 the case when not adding ligand or antibody (control). Suppression of ligand-dependent expression of TGF-β was observed for antibody #115.

In Vitro Analysis of Fluctuations in TGF-β mRNA Caused by Anti-DDR1 Antibody The inhibitory activity of anti-DDR1 antibody on expression of cancer cell TGF-β mRNA was measured in a co-culture system of cancer cells and fibroblasts. 10,000 cells each of human lung carcinoma cell line NCI-H1993 and mouse fibroblast line MRC5 were seeded into Nano Culture Plates (SCIVAX) at 3,333 cells/well followed by the addition of collagen type I (Cellmatrix) to make a final concentration of 100 µg/mL and culturing for 24 hours at 37° C. RNA was extracted using the RNAeasy 96-Well Kit (Qiagen) and a reverse transcription reaction was carried out using the Transcriptor First Strand cDNA Synthesis Kit (Roche). Moreover, Taqman qRT-PCR was carried out with the LightCycler 480 (Roche) using the Human TGF-β Probe/Primer Mix (Applied Biosystems) and the Human Actin Probe/Primer Mix (Applied Biosystems). Here, only TGF-β mRNA derived from human cancer cells can be detected without detecting TGF-β mRNA derived from mouse fibroblasts by using a primer specific to human TGF-β. Measured values were used to calculate relative mRNA expression levels from qRT-PCR Cp values based on a value of 1 for samples not treated with collagen or antibody. As a result, a phenomenon was observed in which rising expression levels of TGF-β mRNA induced by collagen in cancer cells are inhibited by antibody #115 (FIG. 8). TGF-β is a marker molecule for which expression is known to rise during epithelial-mesenchymal transition (EMT) that has been reported to act to promote tumorigenesis, and this result suggests the potential for antibody #115 to inhibit EMT induced by collagen via DDR1.

Example 9

Determination of Sequence of Antibody Variable Region

Total RNA was extracted from hybridoma cells producing anti-DDR1 antibody using the RNAeasy Mini Kit (QIAGEN), and cDNA was synthesized with the SuperScriptIII Cells Direct cDNA Synthesis System (Invitrogen). Primers for amplifying the mouse antibody variable region were synthesized based on non-patent documents (Larrick, J. W. et al., Biochem. Biophys. Res. Commun. (1989) 160, 1250-1256; Jones, S. T. and Bendig, M. M., Biotechnology (1991) 9, 579), and PCR was carried out with PrimeSTAR HS DNA Polymerase (Takara Bio Inc.) to isolate the antibody variable region gene.

The nucleotide sequence of each isolated DNA fragment was determined with the DNA Sequencer ABI PRISM 3730x1 DNA Analyzer (Applied Biosystems) in accordance with the procedure described in the manual provided, using the BigDye Terminator Cycle Sequencing Kit (Applied Biosystems).

Example 10

Preparation of Anti-DDR1 Antibody 20M102

10-1 Preparation of Expression Vectors cDNA sequences encoding the heavy chain and light chain of anti-DDR1 antibody 20M102 described in SEQ ID NOs: 16 to 19 of WO2010/01972 (Patent Document 3) were synthesized and respectively inserted into expression vectors pCXND3 and pCXZD1 using restriction enzyme sites. These are hereinafter referred to as pCXND3-20M102 Heavy Chain and pCXZD1-20M102 Light Chain. pCXND3 and pCXZD1 are both expression vectors having a cytomegalovirus enhancer and fowl β-actin-rabbit β-globin promoter. Neomycin-resistance gene was inserted into pCXND3 and zeocin-resistance gene was inserted into pCXZD1 as marker genes.

10-2 Acquisition of Stable Expression Clones

5 μg each of pCXND3-20M102 Heavy Chain and pCXZD1-20M102 Light Chain fragmented by restriction enzyme treatment were mixed and then transfected into $7.5 \times 10^6$ Chinese hamster ovary cell line CHO cells by electroporation (GenePulser, Bio-Rad). On the following day, neomycin and zeocin were added followed by culturing for about 3 weeks and selecting drug-resistant clones. The culture liquid of each clone was collected and a clone highly expressing 20M102 was selected by ELISA in which human DDR1-ECD-His as indicated in Section 10-3 was immobilized. The nucleotide sequence of human DDR1-ECD-His is shown in SEQ ID NO: 13 and the amino acid sequence is shown in SEQ ID NO: 14.

10-3 Binding Activity to Human DDR1

Antigen (human DDR1-ECD-His) diluted to 2 μg/mL with coating buffer (100 mM sodium bicarbonate, pH 9.6) was dispensed into a 96-well plate (Nunc-Immuno™ 96 MicroWell™ MaxiSorp™ plate; Nalge Nunc International) at 60 μL/well, followed by incubating at least overnight at 4° C. After washing three times with TBS-T, the plate was blocked for 2 hours or more at room temperature with diluent buffer (1/5 dilution of BlockingOne; Nacalai Tesque Inc.). After removing the diluent buffer, 100 μL of the culture liquid of the drug-resistant clone of Section 10-2 was added to the plate followed by incubating for 2 hours at room temperature. After the plate had been washed three times with TBS-T, alkaline phosphatase-labeled goat anti-human IgG antibody (Biosource), diluted 1/5000 with diluent buffer, was added at 100 μL/well followed by incubating for one hour at room temperature. After the plate had been washed three times with TBS-T, a chromogenic reagent BluePhos (KPL) was added at 60 μL/well, followed by measuring absorbance at 600 nm with a microplate reader (WALLAC ARVO SX, PerkinElmer Inc.). As a result, 20M102 expressed in CHO cells were confirmed to have binding activity to DDR1 as described in Patent Document 3.

10-4 Measurement of Antitumor Effects Using Mouse Model Grafted with Human Lung Cancer Human lung carcinoma cell line NCI-H1993 acquired from ATCC was suspended in HBSS at $5 \times 10^7$ cells/mL. 200 μL of the aforementioned cell suspension ($1 \times 10^7$ cells/mouse) were subcutaneously grafted into CAnN.Cg-Foxn1<nu>/Crlcrlj nu/nu (BALB-nu/nu) mice purchased from Charles River Laboratories Japan Inc. The mice were grouped and used in the experiment when the tumor volume reached an average of about 150 mm$^3$ (n=5).

10-5 Antibody Preparation and Administration

Anti-DDR1 antibody was prepared to 2 mg/mL with PBS and administered into the peritoneal cavity of the mice grafted with human lung cancer twice a week for two weeks at 40 mg/kg. PBS was administered in the same manner for use as a negative control.

10-6 Evaluation of Antitumor Effects

Antitumor effects in a mouse model grafted with human lung cancer were calculated using the following equation based on the amount of tumor growth from the start of administration of anti-DDR1 antibody (20th day after grafting tumor) to four days after final administration of anti-DDR1 antibody (34th day after grafting tumor) (Δmm$^3$, average of n=4). Tumor growth suppressive effect (%)=(1−amount of tumor growth of antibody-treated group/amount of tumor growth of control group)×100

10-7 Statistical Processing

Tumor volume was expressed as the mean±standard deviation. Statistical analysis consisted of a comparison between the control group and the treated group by the LSD method using the SAS Preclinical Package Ver. 5.0. In addition, reliability of 95% (*: $p<0.05$) was determined to constitute significance.

10-8 Results

Anti-DDR1 antibody 20M102 was not observed to demonstrate prominent antitumor effects in the NCI-H1993 model (FIG. 3).

INDUSTRIAL APPLICABILITY

The present invention made it possible to obtain anti-DDR1 antibodies which could demonstrate potent antitumor effects in vivo even when used alone. Thus the present invention enables treatment of tumors such as cancer without using a chemotherapeutic agent, and thus is considered to be beneficial for patients.

The invention claimed is:

1. An antibody that binds to the stalk domain of Discoidin Domain Receptor 1 (DDR1) (SEQ ID NO:4) and not to the discoidin domain of DDR1 (SEQ ID NO:3).

2. The antibody according to claim 1 that is a chimeric antibody or humanized antibody.

3. The antibody according to claim 1 that is a minibody.

4. The antibody according to claim 1 that is linked with a cytotoxic agent.

5. A monoclonal antibody produced by a hybridoma deposited under any one of Accession Nos. FERM BP-11399, FERM BP-11398, and FERM BP-11397.

6. A humanized antibody, wherein the antibody is a humanized version of a monoclonal antibody produced by a hybridoma deposited under any one of Accession Nos. FERM BP-11399, FERM BP-11398, and FERM BP-11397.

7. An antibody that binds to the stalk domain of DDR1 (SEQ ID NO:4), wherein the antibody comprises six CDRs identical to heavy chain CDR1, CDR2, and CDR3 and light chain CDR1, CDR2, and CDR3, respectively, of a monoclonal antibody produced by a hybridoma deposited under any one of Accession Nos. FERM BP-11399, FERM BP-11398, and FERM BP-11397.

8. The antibody of claim 1, wherein the antibody has the same epitope specificity as a monoclonal antibody produced by a hybridoma deposited under any one of Accession Nos. FERM BP-11399, FERM BP-11398, and FERM BP-11397.

9. An antibody that binds to the stalk domain of DDR1 (SEQ ID NO:4) and is produced by a host cell expressing cDNAs encoding antibody heavy and light chains identical to heavy and light chains of a monoclonal antibody produced by a hybridoma deposited under any one of Accession Nos. FERM BP-11399, FERM BP-11398, and FERM BP-11397.

10. An antibody that binds to the stalk domain of DDR1 (SEQ ID NO: 4), said antibody comprising light and heavy chain variable domain amino acid sequences identical to those of a monoclonal antibody produced by a hybridoma deposited under any one of Accession Nos. FERM BP-11399, FERM BP-11398, and FERM BP-11397.

11. An antibody that binds to the stalk domain of DDR1 (SEQ ID NO: 4), said antibody comprising light and heavy chains identical to the light and heavy chains of a monoclonal antibody produced by a hybridoma deposited under any one of Accession Nos. FERM BP-11399, FERM BP-11398, and FERM BP-11397.

* * * * *